(12) United States Patent
Sulikowski et al.

(10) Patent No.: US 12,398,115 B2
(45) Date of Patent: Aug. 26, 2025

(54) CHRYSOPHAENTIN ANALOGS AND USE THEREOF

(71) Applicant: Vanderbilt University, Nashville, TN (US)

(72) Inventors: Gary A. Sulikowski, Nashville, TN (US); Christopher Fullenkamp, Nashville, TN (US); Kwangho Kim, Nashville, TN (US); Somnath Jana, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 849 days.

(21) Appl. No.: 17/602,133

(22) PCT Filed: Apr. 9, 2020

(86) PCT No.: PCT/US2020/027536
§ 371 (c)(1),
(2) Date: Oct. 7, 2021

(87) PCT Pub. No.: WO2020/210539
PCT Pub. Date: Oct. 15, 2020

(65) Prior Publication Data
US 2022/0144794 A1   May 12, 2022

Related U.S. Application Data

(60) Provisional application No. 62/831,610, filed on Apr. 9, 2019.

(51) Int. Cl.
*C07D 321/00* (2006.01)
*A61P 31/04* (2006.01)

(52) U.S. Cl.
CPC .......... *C07D 321/00* (2013.01); *A61P 31/04* (2018.01)

(58) Field of Classification Search
None
See application file for complete search history.

(56) References Cited

U.S. PATENT DOCUMENTS 8,399,689 B2 *   3/2013   Bewley ............... C07D 321/00
                                                         549/348

OTHER PUBLICATIONS

Brown, N. (2012). Bioisosteres in Medicinal Chemistry. John Wiley & Sons (Year: 2012).*
Anderson et al., "Comparison of Small Molecule Inhibitors of the Bacterial Cell Division Protein FtsZ and Identification of a Reliable Cross-Species Inhibitor", ACS Chem. Biol., 2012, vol. 7, pp. 1918-1928.

(Continued)

*Primary Examiner* — Jeffrey S Lundgren
*Assistant Examiner* — Anthony Joseph Seitz
(74) *Attorney, Agent, or Firm* — Michael Best & Friedrich LLP

(57) ABSTRACT

Provided are 9-dechlorochrysophaentin analog compounds and the synthesis process thereof. The disclosed compound have remarkable antimicrobial activities that are comparable to, or even more potent than, the natural product chrysophaentin A. Also provided are method of inhibiting bacterial growth or treating bacterial infection by administering an effective amount of the disclosed compounds.

20 Claims, 9 Drawing Sheets

(56) References Cited

OTHER PUBLICATIONS

Brockway, "Synthesis of the diaryl ether cores common to chrysophaentins A, E, and F", Tett. Lett., 2015, vol. 56, No. 23, pp. 3396-3401.
Bisson et al., "Treadmilling by FtsZ filaments drives peptidoglycan synthesis and bacterial cell division", Science, 2017, vol. 355, pp. 739-743.
Boger et al., "Synthesis of the vancomycin CD and DE ring systems", J. Org. Chem., 1997, vol. 62, pp. 4721-4736.
Chao et al., "The first examples of ring-closing olefin metathesis of vinyl chlorides", Org. Lett. 2003, vol. 5, pp. 2505-2507.
Davison et al., "Antimicrobial Chrysophaentin Analogs Identified from Laboratory Cultures of the Marine Microalga Chrysophaeum taylorii", J. Nat. Prod., 2019, vol. 82, pp. 148-153.
Du et al., "At the Heart of Bacterial Cytokinesis: The Z Ring", Trends Microbiol., 2019, vol. 27, pp. 781-791.
Gadebusch et al., "The Discovery of Cell-Wall Active Antibacterial Antibiotics", Crit. Rev. in Biotechnol. 1992, vol. 12, pp. 225-243.
Haranahalli et al., "Recent advances in the discovery and development of antibacterial agents targeting the cell-division protein FtsZ", Bioorg. Med. Chem., 2016, vol. 24, pp. 6354-6369.
Haydon et al., "An inhibitor of FtsZ with potent and selective anti-staphylococcal activity", Science, 2008, vol. 321, pp. 1673-1675.
Herbert et al., "Z-Selective Cross Metathesis with Ruthenium Catalysts: Synthetic Applications and Mechanistic Implications", Angew. Chemie., Int. Ed. 2015, vol. 54, pp. 5018-5024.
Holden, "Probing the mechanistic principles of bacterial cell division with super-resolution microscopy", Curr. Opin. Microbiol., 2018, vol. 43, pp. 84-91.
Hsu et al., "D-Amino Acid Derivatives as in Situ Probes for Visualizing Bacterial Peptidoglycan Biosynthesis", Acc. Chem. Res., 2019, vol. 52, pp. 2713-2722.
Hsu et al., "Full color palette of fluorescent D-amino acids for in situ labeling of bacterial cell walls", Chem. Sci., 2017, vol. 8, pp. 6313-6321.
International Preliminary Report on Patentability for Application No. PCT/US20/27536 dated Sep. 28, 2021 (6 bages).
International Search Report and Written Opinion for Application No. PCT/US20/27536 dated Aug. 3, 2020 (12 pages).
Keffer et al., "Chrysophaentins are competitive inhibitors of FtsZ and inhibit Z-ring formation in live bacteria", Bioorg. Med. Chem., 2013, vol. 21, pp. 5673-5678.
Keffer et al., "Geographic Variability and Anti-Staphylococcal Activity of the Chrysophaentins and Their Synthetic Fragments", Mar. Drugs, 2012, vol. 10, pp. 1103-1125.
Keitz et al., "Improved Ruthenium Catalysts for Z-Selective Olefin Metathesis", J. Am. Chem. Soc, 2012, vol. 135, pp. 693-699.
Kuru et al., "In Situ Probing of Newly Synthesized Peptidoglycan in Live Bacteria with Fluorescent D-Amino Acids", Angew. Chemie., Int. Ed., 2012, vol. 51, pp. 12519-12523.
Lawson et al., "Template-constrained macrocyclic peptides prepared from native, unprotected precursors", Proc. Natl. Acad. Sci. U.S.A., 2013, vol. 110, pp. E3753-E3760.
Lawson et al., "Template-induced macrocycle diversity through large ring-forming alkylations of tryptophan", Tetrahedron, 2013, vol. 69, pp. 7683-7691.
Lutkenhaus et al., "Bacterial cytokinesis: From Z ring to divisome", Cytoskeleton, 2012, vol. 69, pp. 778-790.
Madec et al., "Reactivity of (E)-1-(tert-butyldimethyl)silyloxy-3,3-bis(tributylstannyl)-propene: Syn selective S-E' addition to aldehydes", Tetrahedron Lett., 1997, vol. 38, pp. 6661-6664.
Margalit et al., "Targeting cell division: Small-molecule inhibitors of FtsZ GTPase perturb cytokinetic ring assembly and induce bacterial lethality", Proc. Natl. Acad. Sci. U.S.A., 2004, vol. 101, pp. 11821-11826.
Muller et al., "Targeting a cell wall biosynthesis hot spot", Nat. Prod. Rep., 2017, vol. 34, pp. 909-932.
Piers et al., "Stereoselective Conjugate Addition of Lithium (Phenylthio)(Trimethylstannyl) Cuprate to Alpha, Beta-Acetylenic Esters—Preparation of (E)-4-Lithio-1,3-Pentadienes and (Z)-4-Lithio-1,3-Pentadienes and Their Reaction with Electrophiles", J. Org. Chem., 1980, vol. 45, pp. 4263-4264.
Plaza, et al., "Chrysophaentins A-H, Antibacterial Bisdiarylbutene Macrocycles That Inhibit the Bacterial Cell Division Protein FtsZ", J. Am. Chem. Soc., 2010, vol. 132, pp. 9069-9077.
Ramirez-Diaz et al., "Treadmilling analysis reveals new insights into dynamic FtsZ ring architecture", PLOS Biol., 2018, vol. 16, No. 5.
Rose et al., "Large ring-forming alkylations provide facile access to composite macrocycles", Chem. Sci., 2015, vol. 6, pp. 2219-2223.
Rossiter et al., "Natural Products as Platforms To Overcome Antibiotic Resistance", Chem. Rev., 2017, vol. 117, pp. 12415-12474.
Sarkar et al., "A review on cell wall synthesis inhibitors with an emphasis on glycopeptide antibiotics", Medchemcomm, 2017, vol. 8, pp. 516-533.
Sashuk et al., "Olefin cross-metathesis with vinyl halides", Chem. Commun., 2008, pp. 2468-2470.
Schaffner-Barbero et al., "Targeting the Assembly of Bacterial Cell Division Protein FtsZ with Small Molecules", ACS Chem. Biol., 2012, vol. 7, pp. 268-276.
Scheepstra et al., "A Natural-Product Switch for a Dynamic Protein Interface", Angew. Chemie., Int. Ed., 2014, vol. 53, pp. 6443-6448.
Takeda et al., "The Friedel-Crafts Reaction of 1-(Phenylthio)Vinyl Chlorides", Tetrahedron Lett., 1991, vol. 32, pp. 6563-6566.
Vendeville et al., "A Synthetic Approach to Chrysophaentin F", Chem. Commun., 2019, vol. 55, pp. 4837-4840.
Von Nussbaum et al., "Antibacterial natural products in medicinal chemistry—Exodus or revival?", Angew. Chemie. Int. Ed. 2006, vol. 45, pp. 5072-5129.
Williams et al., "Studies of neodolastanes—Synthesis of the tricyclic core of the trichoaurantianolides", Can. J. hem., 2013, vol. 91, pp. 21-37.
Zhao et al., "Don't let sleeping dogmas lie: new views of peptidoglycan synthesis and its regulation", Molecular Microbiol., 2017, vol. 106, pp. 847-860.

* cited by examiner 9-dechlorochrysophaentin A: Y = Cl; Z = H
iso-9-dechlorochrysophaentin A: Y = H; Z = Cl

PC190723

*S. aureus* amd *B. subtilis*
MIC < 1 mg/mL
Inhibits FtsZ GTPase $IC_{50}$ 55 ng/mL

|  | MIC$_{90}$ (μg/mL) | | | | |
| --- | --- | --- | --- | --- | --- |
|  | S. aureus | MRSA | E. faecalis | VRE | E. coli |
| Chrysophaentin A | 2 | 2 | 2 | 2 | n/a |
| VU0849855 | 2.5 | 2.5 | 2.5 | 5 | n/a |
| VU0848355 | 4.2 | 4.2 | 4.2 | 8.4 | n/a |
| VU0849838 | 1.1 | 1.1 | 0.3 | 2.2 | n/a |
| VU0848354 | 2.1 | 2.1 | 4.2 | 4.2 | n/a |
| Hemichrysophaentin | 10 | 10 | 5.0 | 10 | n/a |
| PC190723 | 0.4 | 0.4 | n/a | n/a | n/a |

FIG. 5B

|  | Inhibition GTPase IC$_{50}$ (μM) | |
| --- | --- | --- |
|  | S. aureus FtsZ | E. coli FtsZ |
| Chrysophaentin A | 9-67 | 9-67 |
| VU0849855 | 10 | 9.5 |
| VU0848355 | 30 | 50 |
| VU0849838 | 10 | 6.5 |
| VU0848354 | 25 | 45 |
| Hemichrysophaentin | 40 | 18 |
| PC190723 | n/a | n/a |

FIG. 5C

CHRYSOPHAENTIN ANALOGS AND USE THEREOF

CROSS-REFERENCE TO RELATED APPLICATION

This patent application is the U.S. national stage entry, under 35 U.S.C. § 371, of International Application Number PCT/US2020/027536, filed Apr. 9, 2020, which claims the benefit of and priority to U.S. Provisional Application No. 62/831,610, filed Apr. 9, 2019, the entire contents of each of which are hereby incorporated by reference.

TECHNICAL FIELD

The present disclosure relates to chrysophaentin analogs and their use as antimicrobial agents.

BACKGROUND

Chrysophaentin A-H were originally isolated from the marine chrysophyte alga *Chrysophaeum taylori* from St. John, U.S. Virgin Islands. Chrysophaentin A, a marine antimicrobial natural product, was found to inhibit the growth of clinically relevant Gram-positive bacteria including *S. aureus*, methicillin-resistant *S. aureus* (MRSA) and vancomycinresistant *E. faecium* (VREF). Chrysophaentin A is the most potent chrysophaentin with a $MIC_{50}$ of 1-4 µM, against gram-positive bacteria, such as MRSA. Further study of chrysophaentin A has been severely hampered due to a lack of supply resulting from variable production from its natural source (with small and irreproducible quantity) and failed production attempts from a microbial fermentation process. Therefore, there remains a need to develop chrysophaentin analogs for use as an antimicrobial agent and methods for making the chrysophaentin analogs.

SUMMARY

In one aspect, the present disclosure provides a compound of formula (I), or a pharmaceutically acceptable salt thereof,

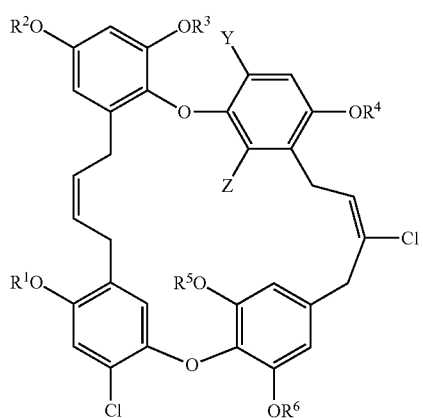

(I)

wherein
$R^1$, $R^2$, $R^3$, $R^4$, $R^5$, and $R^6$ are independently H, $C_{1-4}$alkyl, $C_{3-6}$cycloalkyl, —$CH_2C_{3-6}$cyclalkyl, —C(O) H, —C(O)$C_{1-4}$alkyl, —C(O)$C_{3-6}$cycloalkyl, or —C(O) $CH_2C_{3-6}$cyclalkyl; and
Y is halogen and Z is H; or Y is H and Z is halogen.

The present disclosure also provides a synthesis process for preparing the compounds of formula (I). Also provided is a pharmaceutical composition comprising a compound of formula (I), or a pharmaceutically acceptable salt thereof, and a pharmaceutically acceptable carrier.

In another aspect, the present disclosure provides method of inhibiting the growth of a bacterium, comprising contacting the bacterium with an effective amount of a compound of formula (I), or a pharmaceutically acceptable salt thereof.

In another aspect, the present disclosure provides method of treating a bacterial infection in a subject in need thereof, comprising administering to the subject an effective amount of of a compound of formula (I), or a pharmaceutically acceptable salt thereof.

BRIEF DESCRIPTION OF THE DRAWINGS

FIG. 3A shows the structure and activity of the FtsZ inhibitor PC190723. FIG. 3B shows that chrysophaentins VU084838 and VU0849855 lead to dislocation of FtsZ.

FIG. 4A shows antimcrobial activity against B. *Subtilis*. FIG. 4B shows that chrysophaentin A leads to dispersion of FtsZ.

FIGS. 5A-5C show antimicrobial and FtsZ inhibition of chrysophaentin congeners and PC190723. FIG. 5A shows the chemical structures of chrysophaentin A, 9-dechloro-chrysophaentin A (VU0849855), VU0848355, VU0849838, VU0849854, hemi-chrysophaentin and PC 190723. FIG. 5B shows antimcrobial activities. Bacterial strains were obtained from the ATCC and have the following identifiers: *S. aureus* 25913; MRSA, methicillin-resistant *S. aureus* 43300; *Enterococcus faecalis* 29212; VRE, vancomycin-resistant-*E. faecalis* 51299; *Escherichia coli* 25922. FIG. 5C shows inhibitory activities of *S. aureus* and *E. coli* FtsZ using biochemical GTPase assays.

FIG. 6A shows the agar diffusion assay against *S. aureus*; minimum inhibition concentration ($IC_{50}$) against *S. aureus*. FIG. 6B shows biochemical GTPase-SA-FtsZ inhibition. FIG. 6C shows the MIC and GTPase-SA-FtsZ data for chrysophaentin A.

FIG. 7A shows the FtsZ inhibitor PC190723 produces the expected cell lengthening phenotype, but not VU0848355 or VU0848354.

FIGS. 7B and 7C show that Ampicillin, VU0848355, and VU0848354 inhibit peptidoglycan synthesis, FtsZ inhibitor PC190723 does not. FIG. 7D shows that VU0848355 and VU0848354 displace FtsZ/A and penicillin binding protein PBP2B, a novel phenotype.

DETAILED DESCRIPTION

Figure 1:
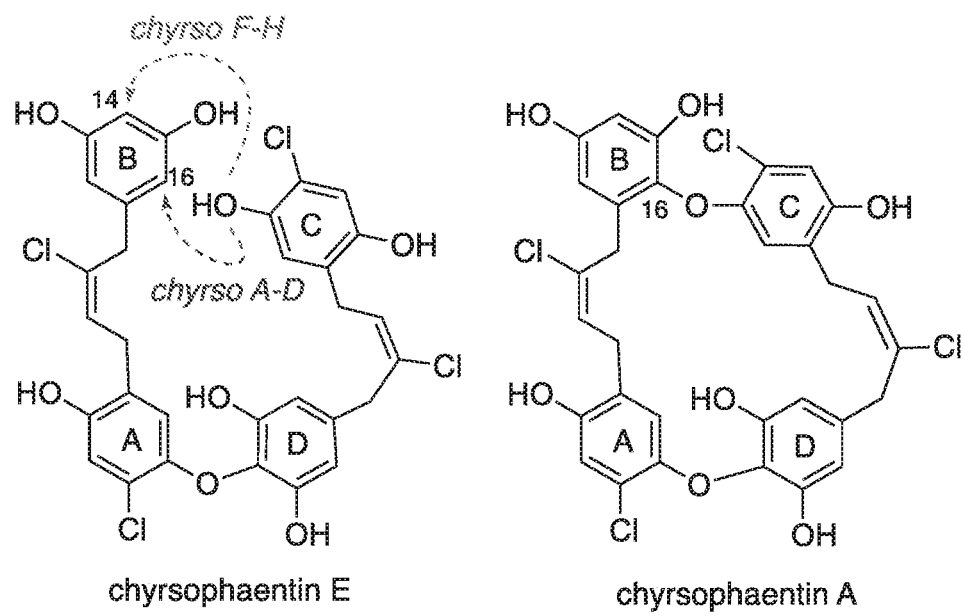
FIG. 1 shows the biosynthetic pathway leading to chrysophaentins A-H and the struction of chrysophaentin A.

The present disclosure relates to synthesis of chrysophaentin analogs, in particular, the synthsis of iso- and 9-dechlorochrysophaentin A compounds. The compounds disclosed herein may inhibit bacterial cell wall biosynthesis by a mechanism involving disassembly of the divisome protein complexes. Accordingly, the compounds disclosed herein may be used as antimicrobial agents. In particular, the compounds disclosed herein may be used for treating bacterial infection.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl" as used herein, means a straight or branched, saturated hydrocarbon chain containing from 1 to 20 carbon atoms. The term "lower alkyl" or "$C_{1-6}$alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "cycloalkyl" as used herein, means a monovalent group derived from an all-carbon ring system containing zero heteroatoms as ring atoms, and zero double bonds. The all-carbon ring system can be a monocyclic, bicylic, or tricyclic ring system, and can be a fused ring system, a bridged ring system, or a spiro ring system, or combinations thereof. Examples of cycloalkyls include, but are not limited to, cyclopropyl, cyclobutyl, cyclopentyl, cyclohexyl, cycloheptyl, and cyclooctyl. The cycloalkyl groups described herein can be appended to the parent molecular moiety through any substitutable carbon atom.

The term "halogen" as used herein, means Cl, Br, I, or F.

In some instances, the number of carbon atoms in a hydrocarbyl substituent (e.g., alkyl or cycloalkyl) is indicated by the prefix "$C_{x-y}$" or "$C_x$-$C_y$-", wherein x is the minimum and y is the maximum number of carbon atoms in the substituent. Thus, for example, "$C_{1-4}$alkyl" or "$C_1$-$C_4$-alkyl" refers to an alkyl substituent containing from 1 to 4 carbon atoms.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an ""effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "subject" or "patient" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating," or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

The isolation, structure elucidation, and antimicrobial activity of chrysophaentins A-H have been reported (FIG. 1). Isolated from the marine alga *Chrysophaeum taylori*, the structures of chrysophaentins A-D and F-H were determined to consist of common halogenated macrocyclic biaryl ethers, while chrysophaentin E was assigned an open-chain structure. Chrysophaentins A-D and F-H may be derived from chrysophaentin E by oxidative cyclization of the C ring phenol at B ring carbons C16 and C14, respectively. Structurally, chrysophaentin A features a macrocyclic biaryl ether core incorporating two trisubstituted chloroalkenes at its periphery (FIG. 1, rings A-D). Studies of chrysophaentin A have been hindered due to unreliable supply from the producing marine alga (*C. taylori*) with small and irreproducible quantity, as well as failed attempts to produce chrysophaentins by in-lab culturing of *C. taylori*. To date, synthetic studies have yielded only chrysophaentin fragments devoid of the macrocyclic core.

In one aspect, the present disclosure provides a compound of formula (I), or a pharmaceutically acceptable salt thereof,

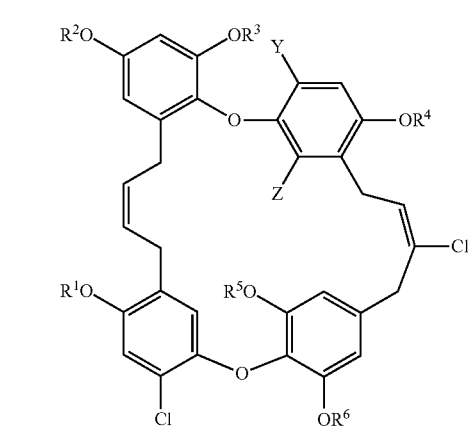

(I)

wherein
$R^1$, $R^2$, $R^3$, $R^4$, $R^5$, and $R^6$ are independently H, $C_{1-4}$alkyl, $C_{3-6}$cycloalkyl, —$CH_2C_{3-6}$cyclalkyl, —C(O) H, —C(O)$C_{1-4}$alkyl, —C(O)$C_{3-6}$cycloalkyl, or —C(O) $CH_2C_{3-6}$cyclalkyl; and
Y is halogen and Z is H; or Y is H and Z is halogen.

In some embodiments, the compounds of formula (I) exists as stereoisomers, such as atropisomers which result from hindered rotation of a single bond. For example, a compound of formula (I) may have a structure of formula (I-a).

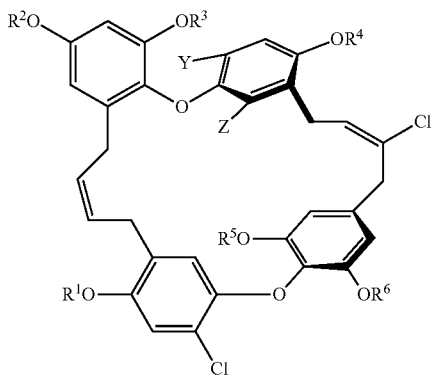

(I-a)

wherein $R^1$, $R^2$, $R^3$, $R^4$, $R^5$, $R^6$, Y and Z are as defined in formula (I).

In some embodiments, Y is halogen and Z is H. In some embodiments, Y is H and Z is halogen.

In some embodiments, $R^1$, $R^2$, $R^3$, $R^4$, $R^5$, and $R^6$ are independently H or $C_{1-4}$alkyl. In some embodiments, $R^1$, $R^2$, $R^3$, $R^4$, $R^5$, and $R^6$ are independently H, methyl, or isopropyl.

In some embodiments, $R^1$, $R^2$, and $R^3$ are H; and $R^4$, $R^5$, and $R^6$ are independently H, methyl, or isopropyl.

In some embodiments, $R^1$, $R^2$, $R^3$ and $R^4$ are H; and $R^5$ and $R^6$ are independently H, methyl, or isopropyl.

In some embodiments, the compound of formula (I) have a structure in which
$R^1$, $R^2$, $R^3$ $R^4$, $R^5$, and $R^6$ are H, Y is halogen, Z is H; $R^1$, $R^2$, $R^3$ $R^4$, $R^5$, and $R^6$ are H, Y is H, Z is halogen; $R^1$, $R^2$, $R^3$ and $R^4$ are H; $R^5$ and $R^6$ are methyl, Y is halogen, Z is H; or $R^1$, $R^2$, $R^3$ and $R^4$ are H; $R^5$ and $R^6$ are methyl, Y is H, Z is halogen.

In some embodiments, the compound of formula (I) has a structure in which $R^1$, $R^2$, $R^3$ $R^4$, $R^5$, and $R^6$ are H, Y is Cl, and Z is H. This is compound is referred to herein as VU0849855.

VU0849855

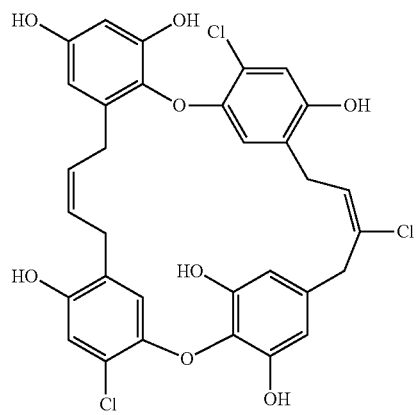

In some embodiments, the compound of formula (I) has a structure in which $R^1$, $R^2$, $R^3$ $R^4$, $R^5$, and $R^6$ are H, Y is H, and Z is Cl. This is compound is referred to herein as VU0849838.

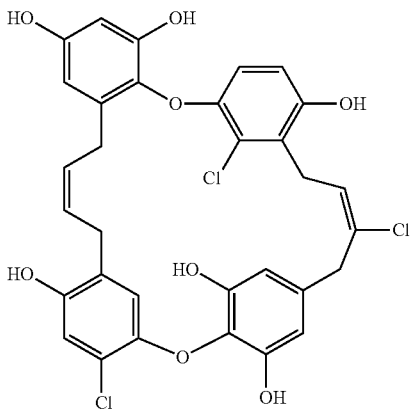

VU0849838

In some embodiments, the compound of formula (I) has a structure in which $R^1$, $R^2$, $R^3$ and $R^4$ are H; $R^5$ and $R^6$ are methyl, Y is Cl, and Z is H. This is compound is referred to herein as VU0848355.

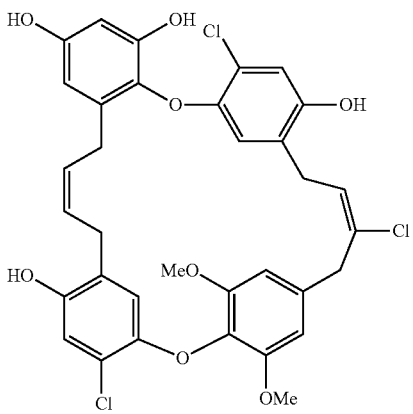

VU0848355

In some embodiments, the compound of formula (I) has a structure in which $R^1$, $R^2$, $R^3$ and $R^4$ are H; $R^5$ and $R^6$ are methyl, Y is H, and Z is Cl. This is compound is referred to herein as VU0848354.

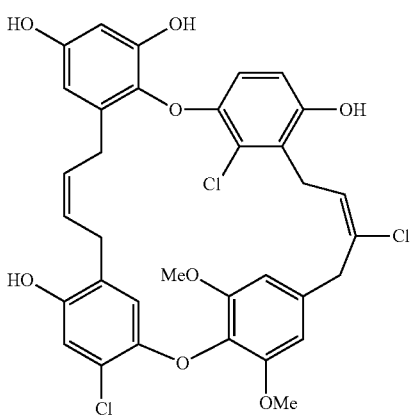

VU0848354

Compound names can be assigned by CHEMDRAW®. The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45:13-30. The disclosure contemplates various stereoisomers and mixtures thereof and these are specifically included within the scope of this disclosure. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns or (3) fractional recrystallization methods. It should be understood that the compound may possess tautomeric forms, as well as geometric isomers, and that these also constitute an aspect of the present disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the disclosure are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positronemitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, Nmethylpiperidine, N-methylmorpholine, dicyclohexylamine, procaine, dibenzylamine, N,Ndibenzylphenethylamine, 1-ephenamine and N,N'-dibenzylethylenediamine, ethylenediamine, ethanolamine, diethanolamine, piperidine, piperazine, and the like.

3. Synthesis

The present disclosure provides a method for preparing a compound of formula (I), or a pharmaceutically acceptable salt thereof, the method comprises converting a compound of formula (II) to the compound of formula (I).

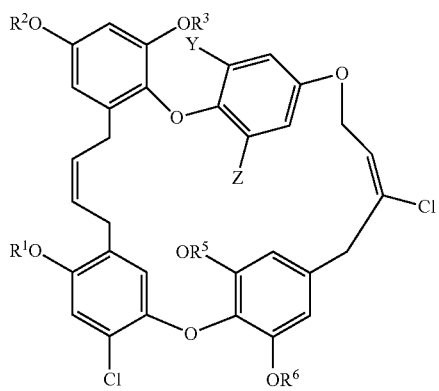

(II)

The conversion may be mediated by a Lewis acid, such as $BF_3 \cdot OEt_2$ and results in O to C alkyl migration.

In some embodiments, the preparation method further comprises reacting a compound of of formula (III)

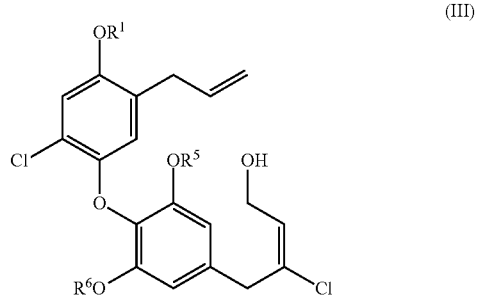

(III)

with a compound of formula (IV)

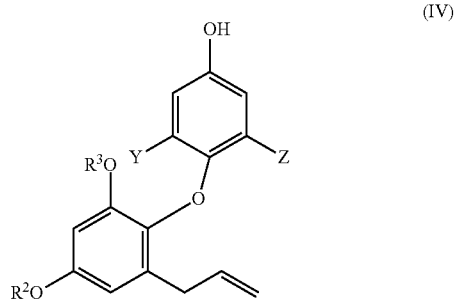

(IV)

to produce the compound of formula (II). This sequence involves a Mitsunobu reaction followed by ring-closing metathesis.

For formula (II), (III), and (IV), $R^1$, $R^2$, $R^3$, $R^5$, $R^6$, Y and Z are as defined in formula (I). In some embodiments, $R^1$, $R^2$, $R^3$, $R^5$, $R^6$, are independently $C_1$-4alkyl. In some embodiments, $R^1$, $R^2$, and $R^3$ are isopropyl. In some embodiments, $R^5$ and $R^6$ are methyl or isopropyl. In some embodiments, $R^1$, $R^2$, $R^3$, $R^5$, and $R^6$ are isopropyl. In some embodiments, $R^5$ and $R^6$ are methyl and $R^1$, $R^2$, and $R^3$ are isopropyl.

In some embodiments, Y is Cl and Z is H. In some embodiments, Y is H and Z is Cl.

In the synthetic methods of the invention, compounds of formula (I), wherein $R^1$, $R^2$, $R^3$, $R^5$, and $R^6$ are $C_{1-4}$alkyl may be converted to compounds of formula (I), wherein $R^1$, $R^2$, $R^3$, $R^5$, and $R^6$ are hydrogen by standard conditions to remove an alkyl protecting group from a phenol (e.g., $BCl_3$, $BBr_3$). Using different alkyl protecting groups, compounds of formula (I) may be prepared where some of $R^1$, $R^2$, $R^3$, $R^5$, and $R^6$ retain the alkyl group following removal of the alkyl group from one or more other positions. For example, methyl may be retained at $R^5$ and $R^6$ following removal of isopropyl at $R^1$, $R^2$, and $R^3$.

In some embodiments, the preparation methods comprises converting a compound of formula (II), in which $R^1$, $R^2$, and $R^3$ are isopropyl and $R^5$ and $R^6$ are methyl or isopropyl to a compound of formula (I).

In some embodiments, the preparation method further comprises reacting a compound of of formula (III), in which $R^1$ is isopropyl and $R^5$ and $R^6$ are methyl or isopropyl, with a compound of formula (IV), in which $R^2$ and $R^3$ are isopropyl, to form a compound of formula (II).

In particular embodiments, the preparation method comprises reacting a compound of of formula (III), in which $R^1$ is isopropyl and $R^5$ and $R^6$ are methyl or isopropyl, with a compound of formula (IV), in which $R^2$ and $R^3$ are isopropyl, Y is H, and Z is Cl, to form a compound of formula (II); and subsequently converting the compound of formula (II) to a compound of formula (I).

Compounds of formula (III) and (IV) may be prepared as described in General Schemes 1 and 2 and the Examples below (Schemes 1 and 2).

General Scheme 1

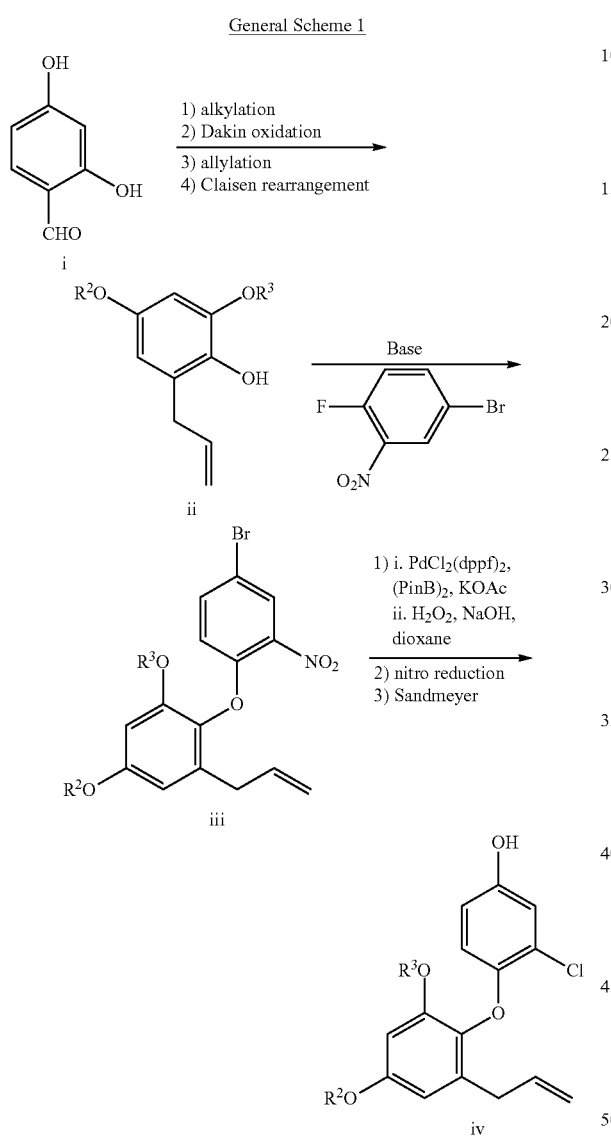

General Scheme 2

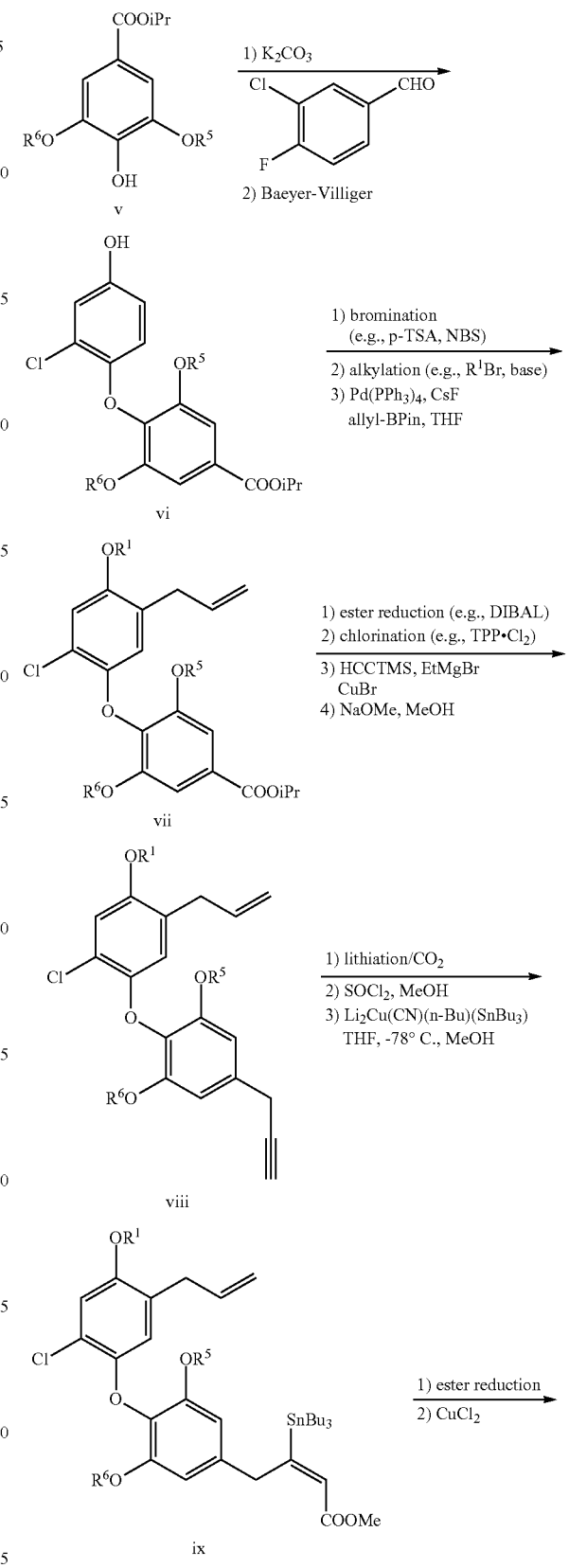

General Scheme 1 shows a process for synthesizing compounds of formula iv.

Starting from resorcinol i, the phenol groups may be protected by base-mediated alkylation (e.g., alkyl bromide, mesylate, tosylate) to form alkyl ethers, followed by Dakin oxidation to generate a new phenol group, which may be allylated under standard conditions (e.g., allyl bromide, base) and subjected to Claisen rearrangement at elevated temperature to provide compounds ii. Nucleophilic aromatic substitution of ii with 5-bromo-2-fluoronitrobenzene may provide compounds iii, which may in turn be converted to iv by diborane cross-coupling with an oxidative workup to provide the phenol, followed by reduction of the nitro group (e.g., Fe, NH$_4$Cl) and Sandmeyer reaction to transform the intermediate diazonium species to a chloro.

-continued

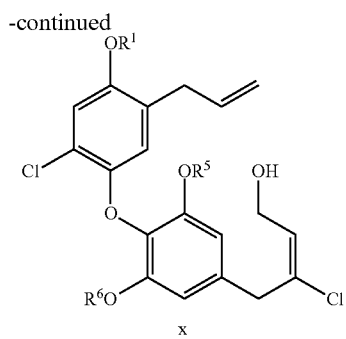

x

General Scheme 2 shows a process for synthesizing compounds of formula x. Nucleophilic aromatic substitution of v ($R^5$ and $R^6$=$C_{1-4}$alkyl) with 3-chloro-4-fluorobenzaldehyde, followed by Baeyer-Villiger oxidation of the aldehyde may provide the phenol vi. Bromination of phenol vi, followed by phenol alkylation and allyl cross-coupling may provide compounds vii. Reduction of the ester of vii, followed by conversion of an intermediate alcohol to the chloro, copper-mediated coupling of the benzyl chloride with trimethylsilylacetylide, and removal of the trimethylsilyl group may provide compounds viii. Lithiation of the terminal alkylne of viii, quenching with $CO_2$, conversion of the acid to an ester and stannyl cupration may provide compounds ix. Reduction of the ester (e.g., DIBAL) to the allylic alcohol and tin-chloride exchange provides x.

Figure 2:
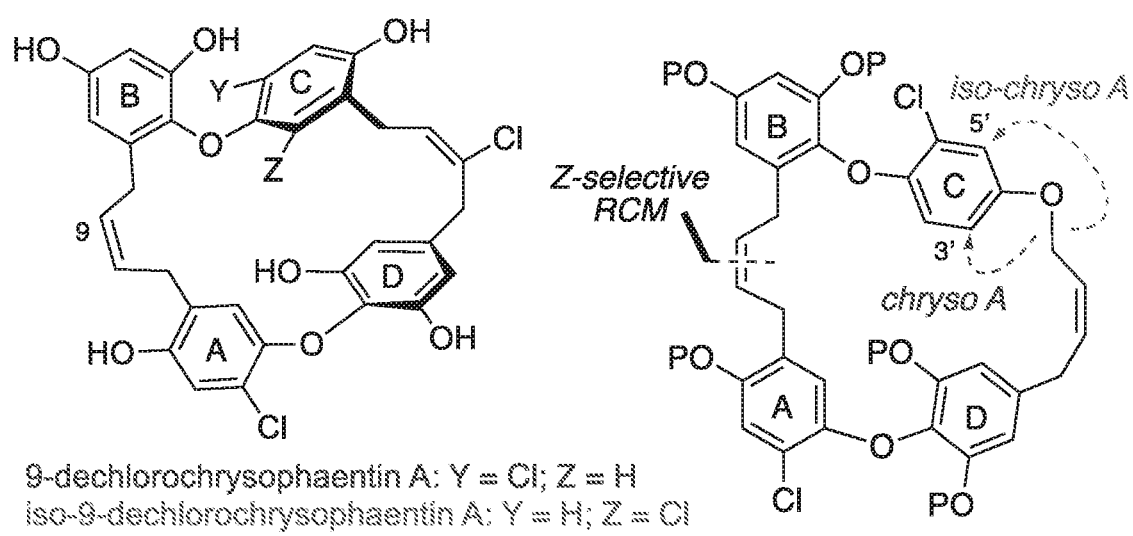
FIG. 2 shows a synthetic strategy leading to 9-dechloro-chyrsophaentins.

A convergent synthesis may be completed starting with a Mitsunobu reaction between a phenol compound of formula (IV) and an allyl alcohol biaryl ether compound of formula (III). The coupled product may undergo cyclization to form a macrocycle compound of formula (II) upon treatment with the Grubbs Z-selective catalyst. The core macrocyclic structure common to the chrysophaentins may be completed by way of a Lewis acid (e.g., $BF_3 \cdot OEt_2$) mediated O to C migration. Removal of the alkyl (e.g., isopropyl) protecting groups (e.g., by treatment with boron trichloride at low temperature) may afford iso- and 9-dechlorochrysophaentin A compounds of formula (I). The O to C rearrangement may occur non-selectively or selectively between carbons C3' and C5' (FIG. 2).

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4th ed.), John Wiley & Sons, NY (2006), which is incorporated herein by reference in its entirety. Synthesis of the compounds of the invention can be accomplished by methods analogous to those described in the synthetic schemes and in the specific examples.

4. Method

Chrysophaentin A displays antimicrobial activity against *S. aureus*, methicillin resistant *S. aureus* (MRSA), *E. faecium* and vancomycin resistant *E. faecium* (VREF). Based on its structural similarity to zantrin Z1, a reported inhibitor of the bacterial cytoskeletal protein FtsZ, the mechanism of action of chrysophaentin A was hypothesized to operate by the same mechanism. Chrysophaentin A was shown to inhibit *S. aureus* and *E. coli* FtsZ GTPase activity and polymerization. The compounds disclosed herein, as dechlorochrysophaentin analogs, show antimicrobial activities that are comparable to, or even more potent than, those of the natural chrysophaentin A.

The antimicrobial activity of the present compounds may result from a novel mechanism of bacterial cell wall biosynthesis inhibition. For example, the present compounds may function as peptidoglycan synthesis inhibitors. In particular, the present compounds may target three classes of proteins: 1) cytoskeletal proteins, such as FtsZ and MreB; 2) peptidoglycan synthases, also known as penicillin-binding proteins (PBPs); and 3) other cell wall synthesis protein components, such as FtsW/RodA or the Min systems. Since chrysophaentins show a strong peptidoglycan synthesis inhibition effect, they may also inhibit the PG synthesis activity of the PBPs.

In one aspect, the present disclosure provides a inhibiting the growth of a bacterium, comprising contacting the bacterium with an effective amount of a compound disclosed herein, or a pharmaceutically acceptable salt thereof.

In some embodiments, the bacterium is a Gram-positive bacterium or a Gram-negative bacterium.

In some embodiments, the bacterium is a Gram-positive bacterium. The bacterium may be a Gram-positive bacterial agent selected from, but not limited to, *Staphylococcus* spp, *Streptococcus* spp, *Enterococcus* spp, *Leuconostoc* spp, *Corynebacterium* spp, *Arcanobacteria* spp, *Trueperella* spp, *Rhodococcus* spp, *Bacillus* spp, *Anaerobic cocci*, Anaerobic Gram-Positive Nonsporulating Bacilli, *Actinomyces* spp,

*Clostridium* spp, *Nocardia* spp, *Erysipelothrix* spp, *Listeria* spp, *Kytococcus* spp, *Mycoplasma* spp, *Ureaplasma* spp, and *Mycobacterium* spp.

In some embodiments, the bacterium is *S. aureus* or *E. faecium*.

In some embodiments, the bacterium is a Gram-negative bacterium. The bacterium may be a Gram-negative bacterial agent selected from, but not limited to, Acetobacteraceae, Aeromonadaceae, Alcaligenaceae, Anaplasmataceae, Armatimonadaceae, Bacteroidaceae, Bartonellaceae, Bdellovibrionaceae, Brachyspiraceae, Brucellaceae, Burkholderiaceae, Campylobacteraceae, Candidatus, Cardiobactenaceae, Chlamydiaceae, Chthonomonadaceae, Comamonadaceae, Coxiellaceae, Cytophagaceae, Desulfovibrionaceae, Enterobacteriaceae, Fimbriimonadaceae, Flavobacteriaceae, Francisellaceae, Fusobacteriaceae, Helicobacteraceae, Legionelaceae, Leptospiraceae, Leptotrichiaceae, Methylobacteriaceae, Moraxellaceae, Moritellaceae, Neisseriacae, Nitrosomonadaceae, Pasteurellaceae, Piscirickettsiaceae, Plesiomonadaceae, Polyangiaceae, Porphyromonadaceae, Prevotellaceae, Pseudomonadaceae, Rhizobiaceae, Rickettsiaceae, Shewanellaceae, Sphingomonadaceae, Spirillaceae, Spirochaetaceae, Succinivibrionaceae, Sutterellaoeae, Thermaceae, Thermotogaceae, Veillonellaceae, Vibrionaceae, Wolbachieae, and Xanthomonadaceae.

In some embodiments, the bacterium is an antibiotic-resistant bacterium. In general, an antibiotic-resistant bacterium as used herein refers to a bacterium that causes an infection and is resistant to conventional antibiotic treatments. For example, the bacteria may be resistant to a compound selected from the group comprising: one or more of aminoglycosides; aminocyclitols; anti-MRSA cephalosporins; antipseudomonal penicillins+β-lactamase inhibitors; carbapenems; non-extended spectrum cephalosporins; 1st and 2nd generation cephalosporins; extended-spectrum cephalosporins; 3rd and 4th generation cephalosporins; cephamycins; fluoroquinolones; folate pathway inhibitors; fusidanes, glycylcyclines; lincosamides; macrolides and ketolides; monobactams; oxazolidinones; penicillins; penicillins+β-lactamase; phenicols; phosphonic acids; pleuromutilins; polymyxins; rifamycins; streptogramins; sulphonamides; tetracyclines. In some embodiments, the bacterium is a multidrug resistant bacterium. As used herein, the term "multidrug resistant" (MDR) means a microbe's (e.g. a bacterium's) ability to be resistant to the treatment of at least one agent in two or more antimicrobial categories, including but not limited to the above antibiotics.

In some embodiments, the bacterium is methicillin resistant *S. aureus* (MRSA) or vancomycin resistant *E. faecium* (VREF).

In another aspect, the present disclosure provides a method of treating a bacterial infection in a subject in need thereof, comprising administering to the subject an effective amount of a compound disclosed herein, or a pharmaceutically acceptable salt thereof.

Ther term bacterial infection refer to an infection on or inside the body of a subject caused by the growth of a population of bacteria. For example, the infection may be caused by a Gram-positive bacterium, a Gram-negative bacterium, or a combination thereof. In some embodiments, the infection is caused by *S. aureus, E. faecium, S. aureus* (MRSA), vancomycin resistant *E. faecium* (VREF), or a combination thereof.

In some embodiments, the subject is a human, such as an adult and an infant. In some embodiments, the infection is on the skin of the subject. In some embodiments, the infection is in the lung, stomach, intestine, blood stream, or internal organs of the subject.

In another aspect, the present disclosure provides compounds, or pharmaceutically acceptable salts thereof, as disclosed herein for use in inhibiting the growth of a bacterium.

In another aspect, the present disclosure provides compounds, or pharmaceutically acceptable salts thereof, as disclosed herein for use in treating a bacterial infection in a subject.

In another aspect, the present disclosure provides use of compounds, or pharmaceutically acceptable salts thereof, as disclosed herein for manufacturing a medicament for treating a bacterial infection in a subject.

Administration

The present compounds or compositions may be administered to a subjects by a variety of known routes, including without limitation oral, inhalation, intravenous, intramuscular, topical, subcutaneous, systemic, and/or intraperitoneal administration.

The amount of the present compounds, or a pharmaceutically acceptable salts thereof, for use in treatment may vary with the particular compound or salt selected, the route of administration, the disease or condition being treated, and the age and condition of the subject being treated. In cases of administration of a pharmaceutically acceptable salt, dosages may be calculated as the free base. In certain situations the disclosed compounds may be administered in amounts that exceed the dosage ranges described herein in order to effectively and aggressively treat particularly aggressive diseases or conditions.

In some embodiments, the compounds, or pharmaceutically acceptable salts thereof, or pharmaceutical compositions as disclosed herein may be administered by inhalation, oral administration, or intravenous administration. In general, however, a suitable dose will often be in the range of from about 0.01 mg/kg to about 100 mg/kg, such as from about 0.05 mg/kg to about 10 mg/kg. For example, a suitable dose may be in the range from about 0.10 mg/kg to about 7.5 mg/kg of body weight per day, such as about 0.10 mg/kg to about 0.50 mg/kg of body weight of the recipient per day, about 0.10 mg/kg to about 1.0 mg/kg of body weight of the recipient per day, about 0.15 mg/kg to about 5.0 mg/kg of body weight of the recipient per day, about 0.2 mg/kg to 4.0 mg/kg of body weight of the recipient per day. The compound may be administered in unit dosage form; for example, containing 1 to 100 mg, 10 to 100 mg or 5 to 50 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Suitable in vivo dosage to be administered and the particular mode of administration may vary depending upon the age, weight, the severity of the affliction, and mammalian species treated, the particular compounds employed, and the specific use for which these compounds are employed. The determination of effective dosage levels to achieve the desired result may be accomplished by known methods, for example, human clinical trials, in vivo studies and in vitro studies. For example, the effective dosages of compounds disclosed herein, or pharmaceutically acceptable salts thereof, may be determined by comparing their in vitro activity, and in vivo activity in animal models. Such comparison may be done by comparison against an established drug.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, FIPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds, salts, and compositions disclosed herein may be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

The compositions described herein may be administered with additional compositions to prolong stability, delivery, and/or activity of the compositions, or combined with additional therapeutic agents, or provided before or after the administration of additional therapeutic agents. Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation.

5. Pharmaceutical Compositions

In another aspect, the present disclosure provides a pharmaceutical composition comprising a compound as disclosed herein, or a pharmaceutically acceptable salt there, and a pharmaceutically acceptable carrier.

The present pharmaceutical compositions may be manufactured by processes known in the art, e.g., by means of conventional mixing, dissolving, granulating, dragee-making, levigating, emulsifying, encapsulating, entrapping or lyophilizing processes.

As described herein, the pharmaceutically acceptable carrier includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Various carriers used in formulating pharmaceutically acceptable compositions and techniques for the preparation thereof are known in the art (e.g., Remington's Pharmaceutical Sciences, Sixteenth Edition, E.W. Martin (Mack Publishing Co., Easton, Pa., 1980)).

Some examples of materials which can serve as pharmaceutically acceptable carriers include, but are not limited to, ion exchangers, alumina, aluminum stearate, lecithin, serum proteins (such as human serum albumin), buffer substances (such as phosphates), glycine, sorbic acid, or potassium sorbate, partial glyceride mixtures of saturated vegetable fatty acids, water, salts or electrolytes (such as protamine sulfate, disodium hydrogen phosphate, potassium hydrogen phosphate, sodium chloride, zinc salts), colloidal silica, magnesium trisilicate, polyvinyl pyrrolidone, polyacrylates, waxes, polyethylenepolyoxypropylene-block polymers, wool fat, sugars (such as lactose, glucose, and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil, soybean oil), glycols (such a propylene glycol or polyethylene glycol), esters (such as ethyl oleate and ethyl laurate), agar, non-toxic compatible lubricants (such as sodium lauryl sulfate and magnesium stearate), coloring agents, releasing agents, coating agents, emulsifying agents, sweetening, flavorant, perfuming agents, preservatives, antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. Solid dosage forms for oral administration include, but are not limited to, capsules, tablets, pills, powders, cement, putty, and granules. Dosage forms for topical or transdermal administration of the present compounds include, but are not limited to, ointments, pastes, creams, lotions, gels, powders, solutions, sprays, inhalants or patches.

6. Examples

General Procedure

All non-aqueous reactions were performed in flame-dried or oven dried round-bottomed flasks under an atmosphere of argon. Stainless steel syringes or cannula were used to transfer air- and moisture-sensitive liquids. Reaction temperatures were controlled using a thermocouple thermometer and analog hotplate stirrer and monitored using liquid-in-glass thermometers. Reactions were conducted at room temperature (approximately 21-23° C.) unless otherwise noted. Flash column chromatography was conducted using silica gel 230-400 mesh. Reactions were monitored by analytical thin-layer chromatography, using EMD Silica Gel 60 F254 glass-backed pre-coated silica gel plates. The plates were visualized with UV light (254 nm) and stained with potassium permanganate or p-anisaldehyde-sulfuric acid followed by charring. Yields were reported as isolated, spectroscopically pure compounds.

Materials

Solvents and chemicals were purchased from Sigma-Aldrich, Acros Organics, TCI and/or Alfa Aesar and used without further purification. Solvents were purchased from Fisher Scientific. Dry dichloromethane ($CH_2Cl_2$) was collected from an MBraun MB-SPS solvent system. Dichloroethane (DCE) was distilled from calcium hydride and stored over 4 Å molecular sieves. Triethylamine, N,N-dimethylformamide (DMF) and dimethyl sulfoxide (DMSO) were used as received in a bottle with a Sure/Seal. N,N-diisopropylethylamine was distilled from calcium hydride and stored over KOH. $BF_3 \cdot Et_2O$ was distilled prior to use from calcium hydride. Deuterated solvents were purchased from Cambridge Isotope Laboratories.

Instrumentation

Preparative reverse phase HPLC (Gilson) was performed using a Phenomenex Gemini column (5 micron, 110 Å, 50×21.20 mm, flow rate 30 mL/min) with UV/Vis detection. Infrared spectra were obtained as thin films on NaCl plates using a Thermo Electron IR100 series instrument and are reported in terms of frequency of absorbance ($cm^{-1}$). $^1H$ NMR spectra were recorded on Bruker 400 or 600 MHz spectrometers and are reported relative to internal chloroform ($^1H$, δ 7.26), methanol ($^1H$, δ 3.31), and DMSO ($^1H$, δ 2.50). Data for $^1H$ NMR spectra are reported as follows: chemical shift (δ ppm), multiplicity (s=singlet, d=doublet, t=triplet, dd=doublet of doublet, ddd=doublet of doublet of doublet, m=multiplet, br-broad), coupling constants (Hz), and integration. $^{13}C$ NMR were recorded on Bruker 100 or 150 MHz spectrometers and are reported relative to internal chloroform ($^{13}C$, δ 77.1), methanol ($^{13}C$, δ 49.2), and DMSO ($^{13}C$, δ 40.3). Low-resolution mass spectra were acquired on an Agilent Technologies Series 1200 single quad ChemStation autosampler system using electrospray ionization (ESI) in positive mode. High-resolution mass spectra (HRMS) were obtained from the Department of Chemistry and Biochemistry, University of Notre Dame Mass Spectrometry Center or the Mass Spectrometry Research Center at Vanderbilt University.

Reagents and Cell Lines

Chemicals-FtsZ inhibitor PC190723 and ampicllin were purchased from Millipore Sigma Aldrich (St. Louis, MO). Chrysophaentin A was obtained from a 2017 collection of the marine alga *C. taylorii* collected in the U.S. Virgin Islands (Permit VIIS-2017-SCI-0034) and isolated as described previously. All bacterial strains used for drug susceptibility testing were obtained from the American Type Culture Collection (Manassas, VA) and included *Escherichia coli* (ATCC 25922), *Enterococcus faecalis* (ATCC 29212), vancomycin-resistant *E. faecalis* (VRE, ATCC 51299), *Staphylococcus aureus* (ATCC 25913), and methicillin-resistant *S. aureus* (MRSA, ATCC 43300). Strains were maintained on agar slants at 4° C. and sub-cultured on fresh agar plates containing ATCC-recommended media. Strains were cultured in liquid media 16 h prior to any antimicrobial screen. BD BBL™ Mueller-Hinton II broth (Fisher Scientific, Hampton NH) was used for MIC determinations.

Minimum Inhibitory Concentration (MIC)

MICs for all compounds were determined using the CLSI guidelines on the test strains. Solutions of each compound were prepared by dissolution in DMSO (Sigma Aldrich, St. Louis MO) at a concentration of 10-20 mg $mL^{-1}$. The final concentration of DMSO in any well was less than 4% and did not affect bacterial growth. Stock solutions were added to Mueller-Hinton II broth and serial two-fold dilutions were prepared in a 96-well microtiter plate (50 μL per well). Fifty microliters (50 μL) of inoculum containing $1 \times 10^6$ CFU $mL^{-1}$ for *E. coli*, *S. aureus*, or MRSA, or $2 \times 10^6$ CFU $mL^{-1}$ for *E. faecalis* or VRE were added to the wells. Plates were covered with a sterile membrane, placed in a plate reader, and agitated for 2 min to mix the contents of the wells. Plates were incubated at 37° C. for 16 h. Wells containing 4% DMSO or gentamycin served as negative and positive controls. MICs correspond to the lowest concentration of antimicrobial agent that completely inhibits growth of the bacteria as detected by eye. Each assay was performed in triplicate and two independent experiments were carried out on separate days.

Cell Lengthening Assay

*Bacillus subtilis* (PY79 WT, lab stock) were inoculated from an overnight plate culture (single colony) to 3 ml LB in 15 ml culture tubes. The cultures were incubated in a 37° C. shaker until $OD_{600}$ reached 0.2. The cultures were then diluted with fresh LB to $OD_{600}$ 0.05, followed by another round of incubation to $OD_{600}$ 0.2. At this point, cells have reached exponentially growing states and were used for experiments. To study the effects of antibiotics on cell length, antibiotics were introduced from stock solutions to 0.3 ml exponentially growing cell cultures to a final concentration of 2×MIC. The cultures were incubated at a 37° C. shaker for 40 minutes, followed by direct addition of 0.7 ml 100% ethanol (70% final ethanol concentration) and then incubation on ice-bath for 1 hour. The fixed cells were imaged using a Nikon Ti-E inverted microscope equipped with a 1.4NA Plan Apo 60X oil objective and Andor iXon EMCCD camera. Cell images were captured under phase-to-contrast channel. Cell length was analyzed using ImageJ and MicrobeJ plug-in.

HADA Incorporation Microscopy Assay

HADA was synthesized according to the reported protocols. Exponentially growing *B. subtilis* (PY79 WT) cells for the experiments were prepared as described above. Antibiotics from stock solutions were introduced to 0.3 ml cell cultures to a final concentration of 10×MIC. After a 5-minute incubation at 37° C., HADA stock solution (100 mM) was directly added to the cultures to a final concentration of 0.5 mM. The cultures were then incubated in a 37° C. shaker for 30 minutes. Cell fixation was then carried out by directly adding 0.7 ml 100% ethanol to the cultures, following 1-hour incubation on ice-bath. The fixed cells were collected using centrifuge (9000 g, 3 minutes), washed with 1×PBS twice, and then resuspended into 1×PBS. The cells were imaged using Nikon Ti-E microscope. HADA signal was detected using DAPI filter set (Excitation 395/25 nm; emission 435/26 nm). HADA intensity was analyzed using ImageJ and MicrobeJ plug-in.

Imaging of FtsZ GFP by SIM

*B. subtilis* strains with fluorescent protein fusion were made (FtsZ-mNeonGreen: bAB185, FtsA-mNeonGreen: bAB167, PBP2B-mNeonGreen: bAB109). Exponentially growing cells for the experiments were prepared as described above. Antibiotic stock solutions were added to 0.3 ml exponentially growing cell cultures to a final concentration of 5×MIC. The cells were incubated at 37° C. for 5 minutes and then immediately imaged using the Ti-E microscope without fixation. mNeonGreen signal was detected using FITC filter set (Excitation 470/24 nm; emission 510/40 nm). Image processing was performed in ImageJ. Images were scaled without interpolation, cropped and rotated. Linear adjustment was performed to optimize contrast and brightness of the images. All the images from the same experiment were processed in the same way in order to ensure fair comparison.

Example 1 Preparation of VU0849855 and VU0849838

A representative synthesis started with O-alkylation of resorcinol 1 (Scheme 1) followed by a Dakin oxidation of the remaining aromatic aldehyde to afford the corresponding phenol. The latter was alkylated with allyl bromide and the resulting allyl aryl ether was subjected to a Claisen rearrangement to afford phenol 2. A solution of phenol 2 and 5-bromo-2-fluoronitrobenzene were subjected to nucleophilic-aromatic substitution reaction conditions to afford biaryl ether 3 in 93% yield. The C-ring aryl bromide 3 was fashioned to corresponding phenol by way of cross-coupling with (BPin) 2 followed by an oxidative work-up. Finally, the C-ring nitro group was reduced the corresponding aniline and chlorinated under Sandmeyer reaction conditions to complete the Northern BC biaryl ether fragment (4).

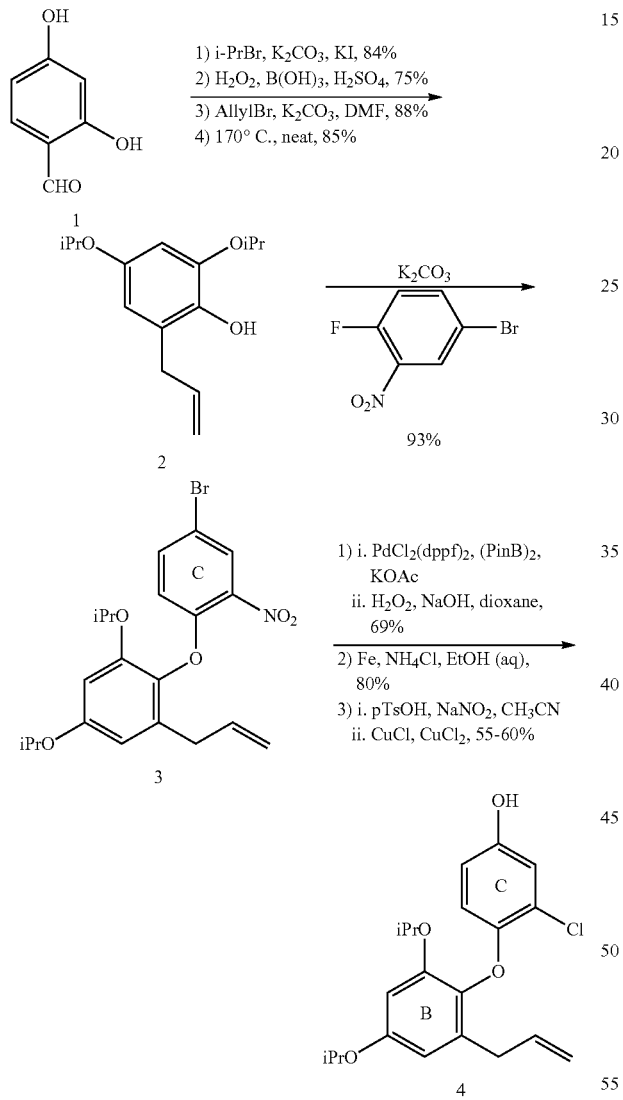

The synthesis of the Southern AD biaryl ether (10), its merger with phenol 5 and completion of 9-dechlorochrysophaentins (VU0849855 and VU0849838) is shown in Scheme 2. First, phenol 5, available in two steps from 4-bromo-3,5-resorcylic acid was coupled with 3-chloro-4-fluorobenzaldehyde by way of a standard SNAr reaction. Baeyer-Villiger oxidation of the A ring aldehyde with the coupled product afforded an intermediate aryl formate that upon treatment with acidic methanol provided phenol 6 in 45-50% (two-steps). Bromination of phenol 6 (NBS, p-TSA) occurred selectively at the C5' carbon and following phenol protection (i-PrBr, $K_2CO_3$), the derived aryl bromide was coupled with allyl pinacol boronate ester to give 7.14 Attention was then turned to D-ring functionalization starting with reduction of the ester group with DIBAL, followed by chlorination (TPP·$Cl_2$) to give an intermediate figures Alkyne 8 was advanced to trisubstituted allyl alcohol 10 starting with homologation to the corresponding alkynoate. Alkynoates derived by direct alkylation of alkyne 8 with chloroformates tended to undergo isomerization to the corresponding allenoate. The undesired isomerization was avoided by proceeding by Fisher esterification of the corresponding alkynoic acid (derived from alkyne 8 by deprotonation followed by carbon dioxide quench). Stannyl cupration[16] of the derived methyl alkynoate proceeded in 60-70% yield to afford enoate 9 as a single geometric isomer. Reduction of enoate 9 to the corresponding allylic alcohol followed by tin-chloride exchange[17] completed assembly of biaryl ether 10. Coupling of phenol 10 and allyl alcohol 16 occurred under Mitsunobu reaction conditions, resulted in smooth merger of the BC and AD fragments. The coupled product underwent cyclization to macrocycle 11 on treatment with Grubbs Z-selective catalyst (C633)[18] in yields of 65 to 70%. Heating a dichloroethane solution of aryl ether 11 and $BF_3 \cdot OEt_2$ afforded a near 1:1 mixture of isomeric products from non-selective O to C3'/C5' alkyl migration. Removal of the iso-propyl protecting groups proceeded smoothly on treatment with boron trichloride at low temperature and afforded a separable mixture of 9-dechlorochrysophaentin A (VU0849855) and iso-9-dechlorochrysophaentin A (VU0849838).

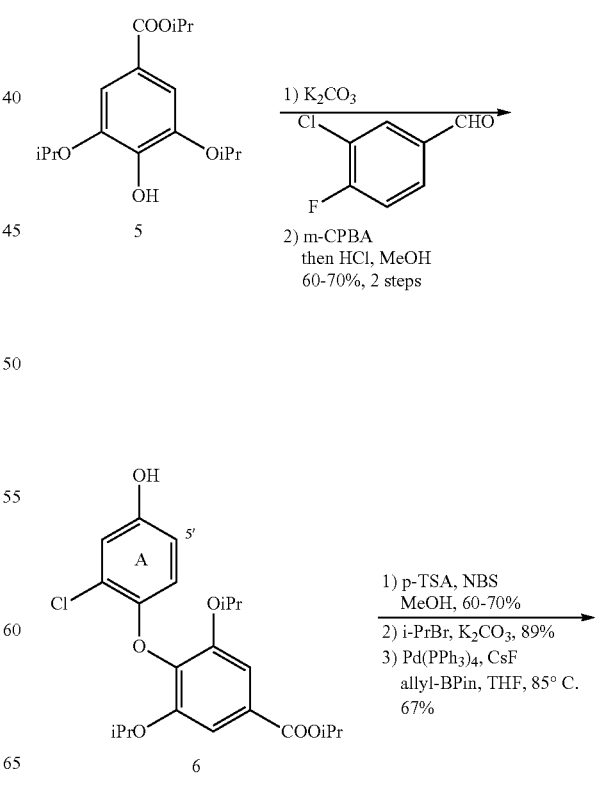

-continued

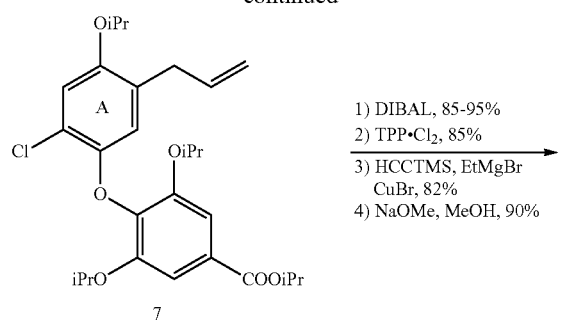

7

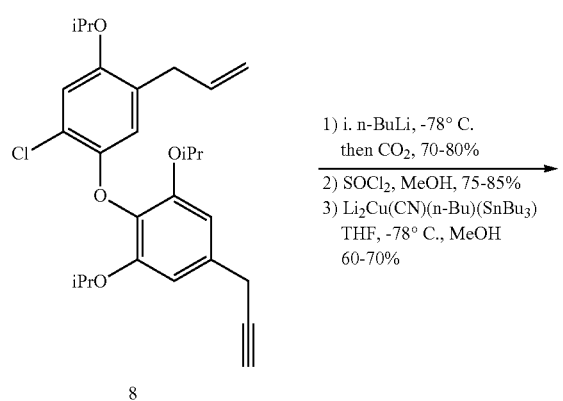

8

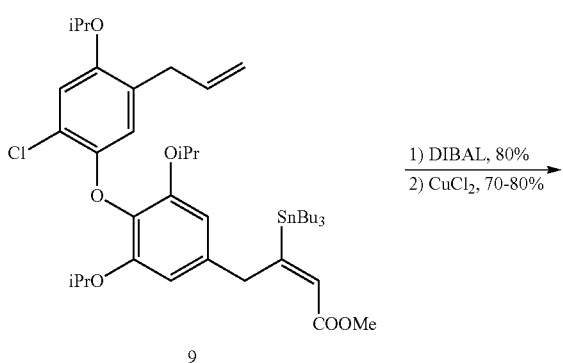

9

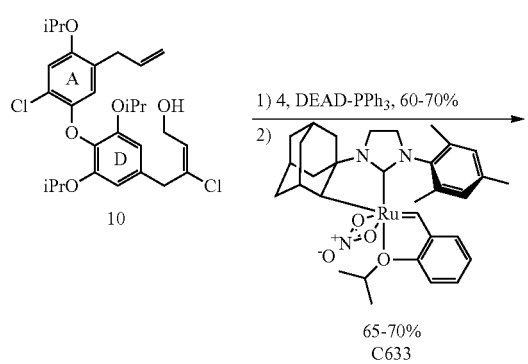

10

-continued

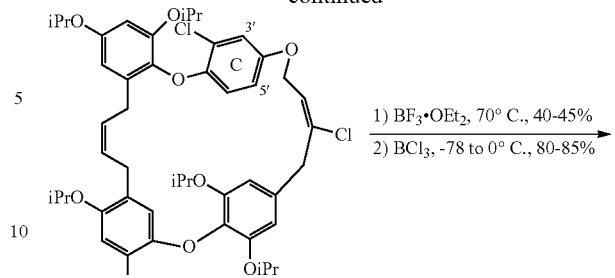

11

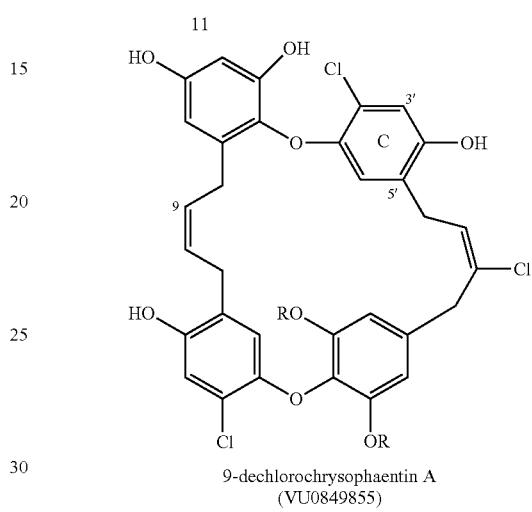

9-dechlorochrysophaentin A
(VU0849855)

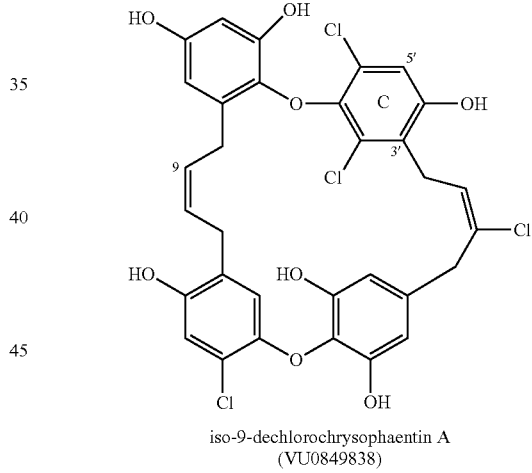

iso-9-dechlorochrysophaentin A
(VU0849838)

S1

To a suspension of 2,4-dihydroxybenzaldehyde (1) (10.0 g, 72.4 mmol), $K_2CO_3$ (30.0 g, 217 mmol, 3.00 equiv), KI (310 g, 217 mmol, 3.00 equiv) in DMF (200 mL) was added 2-bromopropane (270 mL, 289 mmol, 4.00 equiv). The reaction mixture was heated and maintained at 50° C. for 18 h, and then allowed to cool to room temperature. The mixture was diluted with EtOAc (200 mL), washed with water (2×150 mL) and brine (150 mL), dried ($MgSO_4$), filtered and concentrated in vacuo. The residue was purified by flash column chromatography (silica gel, gradient elution, 0-10% EtOAc in hexanes) to afford 15.1 g (94%) of S1 as a yellow-orange oil: $^1$H NMR (400 MHz, CDCl$_3$) δ 10.3 (s, 1H), 7.79 (d, J=8.7 Hz, 1H), 6.50 (dd, J=8.7, 2.0 Hz, 1H), 6.41 (d, J=2.0 Hz, 1H), 4.62 (m, 2H), 1.32 (d, J=6.0 Hz, 6H), 1.29 (d, J=6.0 Hz, 6H); $^{13}$C NMR (100 MHz, CDCl$_3$) δ 188.5, 164.5, 162.3, 130.1, 119.5, 106.9, 101.2, 70.9, 70.2, 21.9.

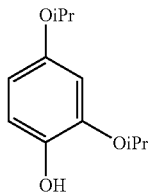

S2

To a suspension of boric acid (103 g, 167 mmol, 5.0 equiv) in THF (100 mL) was added conc. H$_2$SO$_4$ (4.80 mL, 902 mmol, 1.80 equiv) followed by a solution of H$_2$O$_2$ (110 mL, 107 mmol, aqueous 30%, 3.20 equiv). After the mixture was stirred for 30 min, a solution of aldehyde S1 (7.43 g, 33.4 mmol) in THF (100 mL) was added and stirring was continued for 5 h. The suspension was filtered, the filtrate was cooled to 0° C. and neutralized with saturated aq NaHCO$_3$ (100 mL). The mixture was extracted with EtOAc (3×100 mL), and the combined organic extracts were washed with brine (100 mL), dried (MgSO$_4$), filtered and concentrated in vacuo. The residue was purified by flash column chromatography (silica gel, gradient elution, 0-10% EtOAc in hexanes) to afford 7.4 g (86%) of S2 as a yellow oil: $^1$H NMR (400 MHz, CDCl$_3$) δ 6.82 (d, J=8.7 Hz, 1H), 6.50 (d, J=2.5 Hz, 1H), 6.40 (dd, J=8.7, 2.5 Hz, 1H), 5.47 (s, 1H, exchanges with D$_2$O), 4.54-4.51 (m, 1H) 4.41-4.38 (m, 1H), 1.35 (d, J=6.0 Hz, 6H), 1.30 (d, J=6.0 Hz, 6H); $^{13}$C NMR (100 MHz, CDCl$_3$) δ 151.4, 145.0, 140.9, 114.2, 107.9, 104.2, 71.6, 71.0, 22.1.

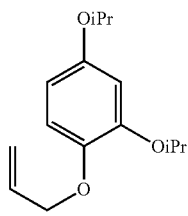

S3

To a solution of phenol S2 (7.99 g, 379 mmol) in DMF (82.0 mL) was added K$_2$CO$_3$ (131 g, 94.9 mmol, 2.50 equiv) followed by allyl bromide (6.57 mL, 75.9 mmol, 2.00 equiv). The suspension was allowed to stir for 18 h, diluted with water (100 mL) and extracted with EtOAc (3×100 mL). The combined organic extracts were washed with water (3×100 mL) and brine (100 mL), dried (MgSO$_4$), filtered, and concentrated in vacuo. The residue was purified by flash column chromatography (silica gel, gradient elution, 0-20% EtOAc in hexanes) to afford 8.65 g (91%) of S3 as a yellow oil: $^1$H NMR (400 MHZ, CDCl$_3$) δ 6.82 (d, J=8.7 Hz, 1H), 6.52 (d, J=2.8 Hz, 1H), 6.41 (dd, J=8.7, 2.8 Hz, 1H), 6.17-6.02 (m, 1H), 5.38 (dd, J=17.2, 1.6 Hz, 1H), 5.23 (dd, J=10.1, 1.5 Hz, 1H) 4.51 (m, 2H) 4.49-4.39 (m, 2H), 1.35 (d, J=6.0 Hz, 6H), 1.31 (d, J=6.0 Hz, 6H); $^{13}$C NMR (100 MHz, CDCl$_3$) δ 153.0, 149.2, 143.9, 134.3, 117.1, 116.9, 107.6, 106.9, 71.8, 71.4, 70.7, 22.3, 22.2.

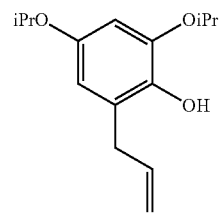

2

Allyl ether S3 (8.65 g, 34.5 mmol) was added to a microwave vial, neat. The vial was sealed, and heated and maintained at 185° C. in a reaction block for 18 h. The vial was then allowed to cool to room temperature, the crude residue was purified by flash column chromatography (silica gel, gradient elution, 0-15% EtOAc in hexanes) to afford 7.65 g (92%) of phenol 2 as a yellow oil: $^1$H NMR (400 MHz, CDCl$_3$) δ 6.40 (d, J=2.7 Hz, 1H), 6.33 (d, J=2.7 Hz, 1H), 6.06-5.97 (m, 1H), 5.48 (s, 1H, exchanges with D$_2$O), 5.14-5.06 (m, 2H), 4.53 (m, 1H), 4.42 (m, 1H), 3.41 (d, J=7.0 Hz, 2H), 1.36 (d, J=6.0 Hz, 6H), 1.32 (d, J=6.0 Hz, 6H); $^{13}$C NMR (100 MHz, CDCl$_3$): 150.7, 144.8, 138.7, 136.7, 125.8, 115.5, 109.0, 101.8, 71.6, 70.8, 34.1, 22.23, 22.20.

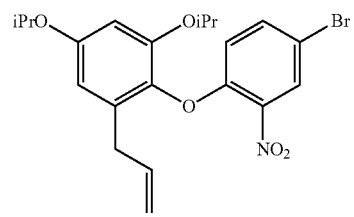

3

To a solution of phenol 2 (9.45 g, 38.7 mmol) in DMF (75.0 mL) was added K$_2$CO$_3$ (105 g, 754 mmol, 2.00 equiv) and 4-bromo-1-fluoro-2-nitrobenzene (8.30 g, 37.7 mmol, 2.00 equiv). The suspension was heated and maintained at 80° C. for 48 h (judged complete by LCMS analysis). The reaction mixture was allowed to cool to room temperature before being diluted with water (150 mL) and the solution was extracted with ether (3×100 mL). The combined organic extracts were washed with saturated aq NH$_4$Cl (200 mL), water (2×200 mL) and brine (250 mL), dried (MgSO$_4$), filtered and concentrated in vacuo. The residue was purified by flash column chromatography (silica gel, gradient elution, 0-0.4-1% EtOAc in hexanes) to afford 164 g (95%) of biaryl ether 3 as an orange oil: R$_f$ 0.54 (9:1 hexanes/EtOAc); IR (thin-film): 3081, 2978, 1601, 1531 cm$^{-1}$; $^1$H NMR (400 MHZ, CDCl$_3$) δ 8.02 (d, J=2.4 Hz, 1H), 7.44 (dd, J=8.9, 2.4 Hz, 1H), 6.61 (d, J=8.9 Hz, 1H), 6.40 (s, 2H), 5.87-5.80 (m, 1H), 5.04-4.96 (m, 2H), 4.51 (m, 1H), 4.38 (m, 1H), 3.31 (d, J=7.0 Hz, 2H), 1.33 (d, J=6.0 Hz, 6H), 1.11 (d, J=6.0 Hz, 6H); $^{13}$C NMR (100 MHZ, CDCl$_3$) δ 156.1, 151.6, 150.4, 139.6, 136.3, 135.7, 134.9, 134.7, 127.9, 118.4, 116.6, 112.4, 108.3, 103.0, 71.6, 70.3, 34.5, 22.1, 21.9; LRMS calculated for C$_{21}$H$_{24}$BrO$_5$$^+$ [M+H]$^+$ m/z 450.0, measured LC/MS (ESI) R$_f$ 1.06 min, m/z 450.0 [M+H]$^+$.

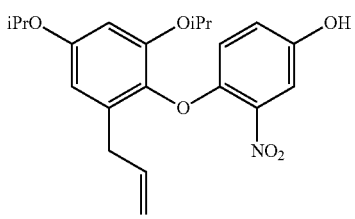

S4

To a degassed (argon purge for 20 min) solution of aryl bromide 3 (164 g, 364 mmol) and bis(pinacolato)diboron (112 g, 43.7 mmol, 1.20 equiv) in 1,4-dioxanes (145 mL) was added potassium acetate (7.10 g, 72.8 mmol, 2.00 equiv) and Pd(dppf)Cl$_2$ (800 mg, 1.09 mmol, 3.00 mol %). The reaction mixture was heated and maintained at 80° C. for 18 h (judged complete by LCMS). The reaction was cooled to 0° C. before a solutions of H$_2$O$_2$ (9.33 mL, 911 mmol, aqueous 30%, 2.50 equiv) and a 1M NaOH (911 mL, 911 mmol, 2.50 equiv) were added. The reaction was allowed to warm to room temperature and stir for 20 min. The crude reaction mixture was acidified with 1 N HCl (105 mL) and extracted with EtOAc (3×200 mL). The combined organic extracts were washed with saturated aq NaHCO$_3$ (150 mL), water (200 mL) and brine (200 mL), dried (MgSO$_4$), filtered, and concentrated in vacuo. The residue was purified by flash column chromatography (silica gel, gradient elution, 0-20% EtOAc in hexanes) to afford 11.2 g (79%) of phenol S4 as an orange oil: R$_f$ 0.37 (2:1 hexanes/EtOAc); IR (thin-film): 3443, 2978, 2930, 1596, 1529, 1478, 1346, 1209, 1116 cm$^{-1}$; $^1$H NMR (400 MHZ, CDCl$_3$) δ 7.39 (d, J=3.0 Hz, 1H), 6.85 (dd, J=9.0, 3.0 Hz, 1H), 6.56 (d, J=8.8 Hz, 1H), 6.41 (s, 2H), 5.86-5.81 (m, 1H), 5.04-4.97 (m, 2H), 4.54-4.48 (m, 1H), 4.40-434 (m, 1H), 3.32 (d, J=7.0 Hz, 2H), 1.34 (d, J=6.0 Hz, 6H), 1.08 (d, J=6.0 Hz, 6H); $^{13}$C NMR (100 MHz, CDCl$_3$): 155.5, 150.6, 149.6, 146.6, 138.8, 136.2, 135.9, 135.0, 121.6, 117.7, 116.6, 111.7, 108.9, 103.6, 71.8, 70.8, 34.4, 22.1, 21.8; LRMS calculated for C$_{21}$H$_{25}$NO$_6^+$ [M+H]$^+$ m/z 388.1, measured LC/MS (ESI) R$_f$ 1.25 min, m/z 388.0 [M+H]$^+$.

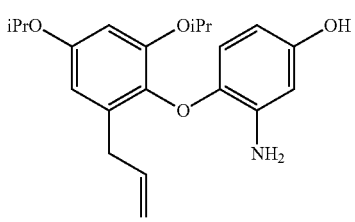

S5

A suspension of iron powder (4.79 g, 86.0 mmol, 3.00 equiv) and ammonium chloride (13.8 g, 258 mmol, 9.00 equiv) in ethanol (136 mL) and water (53.0 mL) was heated to 45° C. for 15 min (rust orange in color), before a solution of S4 (11.1 g, 28.6 mmol) in CH$_3$CN (136 mL) was added. The reaction mixture was heated and maintained at reflux, until judged complete by TLC analysis (ca. 2 h), the reaction was allowed to cool to room temperature and quenched with saturated aq NaHCO$_3$ (100 mL). The quenched reaction mixture was extracted with EtOAc (3×150 mL), washed with saturated aq NH$_4$Cl (2×100 mL) and brine (150 mL), dried (MgSO$_4$), filtered and concentrated in vacuo. The crude residue was purified by flash column chromatography (silica gel, gradient elution, 0-35% EtOAc in hexanes) to afford 8.08 g (80%) of aniline S5 as a red foam: R$_f$ 0.51 (DCM/MeOH: 9:1); $^1$H NMR (400 MHZ, CDCl$_3$) δ 6.41 (d, J=2.8 Hz, 1H), 6.37 (d, J=2.8 Hz, 1H), 6.28 (d, J=2.8 Hz, 1H), 6.22 (d, J=8.6 Hz, 1H), 6.0 (dd, J=8.6, 2.8 Hz, 1H), 5.91-5.84 (m, 1H), 5.05-4.99 (m, 2H), 4.51-4.48 (m, 1H), 4.40-4.37 (m, 1H), 3.29 (d, J=6.6 Hz, 2H), 1.34 (d, J=6.0 Hz, 6H), 1.12 (d, J=6.0 Hz, 6H); $^{13}$C NMR (100 MHz, CDCl$_3$) δ 155.0, 151.2, 150.6, 141.3, 137.6, 137.1, 136.6, 135.0, 116.1, 114.4, 108.3, 104.2, 103.2, 103.1, 71.3, 70.4, 34.5, 22.2, 22.0; LRMS calculated for C$_{21}$H$_{27}$NO$_4^+$ [M+H]$^+$ m/z 358.2, measured LC/MS (ESI) R$_f$ 1.01 min, m/z 358.4 [M+H]$^+$.

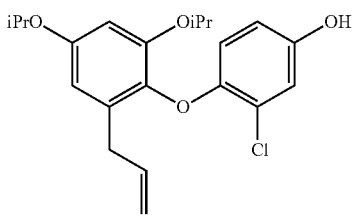

4

To a degassed (argon purge for 20 min), 0° C. solution of S5 (7.87 g, 22.0 mmol) in CH$_3$CN (440 mL) was added p-TSA (12.5 g, 66.0 mmol, 3.00 equiv). The reaction mixture was maintained at 0° C. for 10 min, then NaNO$_2$ (3.03 g, 44.0 mmol, 2.00 equiv) was added as a solution in water (22 mL) dropwise over 45 min. The reaction mixture was maintained at 0° C. for 5 min, then CuCl (43.5 g, 440 mmol, 20.0 equiv) and CuCl$_2$ (88.0 g, 660 mmol, 30.0 equiv) were added. The slurry was allowed to stir at 0° C. for 30 min, then the reaction mixture was allowed to warm to room temperature and continue to stir for 6 h (judged complete by LCMS). Saturated aq NH$_4$Cl (1500 mL) was added and the reaction mixture was extracted with EtOAc (4×500 mL). The combined organic extracts were washed with saturated aq NH$_4$Cl (2×500 mL) and brine (600 mL). The organic extracts were dried (MgSO$_4$), filtered and concentrated in vacuo. The crude residue was purified by flash column chromatography (silica gel, DCM) to afford 4.14 g (50%) of aryl chloride 4 as yellow oil: R$_f$ 0.24 (DCM); $^1$H NMR (400 MHZ, CDCl$_3$) δ 6.91 (d, J=2.9 Hz, 1H), 6.48 (dd, J=8.9, 2.9 Hz, 1H), 6.41 (m, 2H), 6.38 (d, J=8.9 Hz, 1H), 5.92-5.83 (m, 1H), 5.06-4.99 (m, 2H), 4.83 (s, 1H, exchanges with D$_2$O), 4.51-4.48 (m, 1H), 4.42-4.39 (m, 1H), 3.29 (d, J=6.8 Hz, 2H), 1.34 (d, J=6.0 Hz, 6H), 1.13 (d, J=6.0 Hz, 6H); $^{13}$C NMR (100 MHz, CDCl$_3$) δ 155.2, 151.0, 149.9, 148.8, 137.2, 136.3, 135.1, 122.4, 117.1, 116.3, 115.5, 114.1, 108.8, 103.9, 71.8, 70.5, 34.5, 22.2, 22.0; LRMS calculated for C$_{21}$H$_{25}$ClO$_4^+$ [M+H]$^+$ m/z 377.1, measured LC/MS (ESI) R$_f$ 1.29 min, m/z 377.4 [M+H]$^+$.

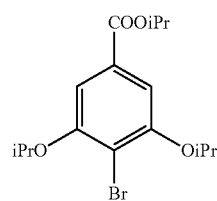

S6

To a solution of 4-bromo-3,5-dihydroxybenzoic acid (40.0 g, 171 mmol) in DMF (600 mL) was added potassium carbonate (94.8 g, 686 mmol, 4.00 equiv), tetrabutylammonium iodide (6.00 g, 17.6 mmol, 10.0 mol %), and 2-bromopropane (75.0 mL, 858 mmol, 5.00 equiv). The suspension was heated and maintained at 50° C. for 72 h. Upon completion, as judged by TLC (ca. 48-72 h), the reaction mixture was allowed to cool to room temperature, diluted with water (600 mL) and extracted with EtOAc (3×400 mL). The combined organic extracts were washed with brine (3×200 mL), dried (MgSO$_4$), filtered and concentrated in vacuo. The crude residue was purified by flash column chromatography (silica gel, gradient elution, 0-20%, EtOAc in hexanes) to afford 57.3 g (92%) of ester S6 as a yellow oil: R$_f$ 0.80 (2:1 hexanes/EtOAc); IR (thin-film): 2975, 1716, 1580 cm$^{-1}$; $^1$H NMR (400 MHZ, CDCl$_3$) δ 7.20 (s, 2H), 5.24-5.18 (m, 1H), 4.65-4.59 (m, 2H), 1.38-1.34 (m, 18H); $^{13}$C NMR (100 MHz, CDCl$_3$) δ 165.6, 155.8, 130.6, 110.7, 108.6, 72.3, 68.8, 22.0, 21.9; LRMS calculated for C$_{16}$H$_{23}$BrO$_4^+$ [M+H]$^+$ m/z 359.0, measured LC/MS (ESI) R$_f$ 0.941 min, m/z 359.4 [M+H]$^+$.

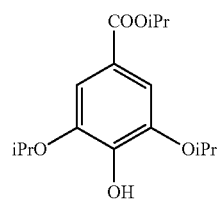

5

To a −90° C. solution of aryl bromide S6 (59.4 g, 165 mmol) in THF (470 mL) was added a solution of n-BuLi (72.0 mL, 173 mmol, 2.4 M in hexanes, 1.05 equiv) dropwise over 1 h. The reaction mixture was maintained at −90° C. for 1 h, then B(OMe)$_3$ (36.9 mL, 331 mmol, 2.00 equiv) was added over 10 min. The reaction mixture was allowed to slowly warm to room temperature and maintained for 18 h. Solutions of H$_2$O$_2$ (55.0 mL, 529 mmol, aqueous 30%, 3.00 equiv) and NaOH (165 mL, 165 mmol, 1 M, 1.00 equiv) were added. The mixture was allowed to stir for 20 min, neutralized with 1M HCl (165 mL) and extracted with ether (3×250 mL). The organic layers were combined, washed with brine (400 mL), dried (MgSO$_4$), filtered and concentrated in vacuo. The crude residue was purified by flash column chromatography (silica gel, gradient elution, 0-10% EtOAc in hexanes) to afford 29.6 g (60%) of 5 as a yellow oil: R$_f$ 0.39 (4:1 hexanes/EtOAc); IR (thin-film): 3414, 1699 cm$^{-1}$; $^1$H NMR (400 MHZ, CDCl$_3$) δ 7.27 (s, 2H), 6.06 (s, 1H, exchanges with D$_2$O), 5.21-5.17 (m, 1H); 4.63-4.58 (m, 2H), 1.34-1.32 (m, 18H); $^{13}$C NMR (150 MHz, CDCl$_3$) δ 165.9, 144.9, 141.8, 121.6, 110.0, 72.1, 68.1, 22.1, 21.9; LRMS calculated for C$_{16}$H$_{24}$O$_5^+$ [M+H]$^+$ m/z 297.1, measured LC/MS (ESI) R$_f$ 0.550 min, m/z 297.5 [M+H]$^+$.

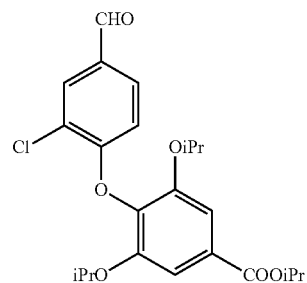

S7

To a solution of 5 (14.5 g, 48.8 mmol) in DMF (122 mL,) was added K$_2$CO$_3$ (13.5 g, 97.6 mmol, 2.00 equiv) followed by 3-chloro-4-fluorobenzaldehyde (7.74 g, 48.8 mmol, 1.00 equiv). The resulting suspension was heated and maintained at 120° C. for 18 h. Upon completion, as judged by LCMS analysis (ca. 16-18 h), the reaction was allowed to cool to room temperature and diluted with water (200 mL). The crude reaction mixture was extracted with EtOAc (3×200 mL). The combined organic extracts were washed with water (2×200 mL) and brine (2×200 mL), dried (MgSO$_4$), filtered, and concentrated in vacuo. The resulting residue was purified by flash column chromatography (silica gel, gradient elution, 0-10% EtOAc in hexanes) to afford 19.8 g (90%) of biaryl ether S7 as a yellow oil: R$_f$ 0.44 (4:1 hexanes/EtOAc); IR (thin-film) 2979, 2933, 1706, 1589, 1479, 1369, 1243 cm$^{-1}$; $^1$H NMR (400 MHZ, CDCl$_3$) δ 9.85 (s, 1H), 7.96 (d, J=2.0 Hz, 1H), 7.58 (dd, J=8.0, 2.0 Hz, 1H), 7.32 (s, 2H), 6.64 (d, J=8.0 Hz, 1H), 5.27-5.21 (m, 1H), 4.58-4.52 (m, 2H), 1.38 (d, J=6.4 Hz, 6H); 1.20 (d, J=6.4 Hz, 12H); $^{13}$C NMR (100 MHz, CDCl$_3$) δ 189.8, 165.5, 158.9, 151.2, 138.5, 131.7, 131.4, 129.4, 128.6, 123.9, 115.5, 110.2, 72.4, 68.9, 22.07, 22.04; LRMS calculated for C$_{23}$H$_{27}$ClO$_6^+$ [M+H]$^+$ m/z 435.1, measured LC/MS (ESI) R$_f$ 0.955 min, m/z 435.0.

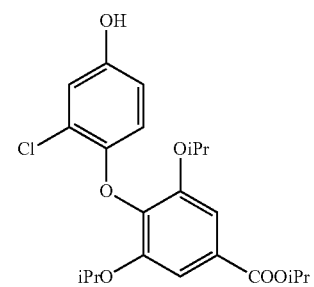

6

To a 0° C. solution of aldehyde S7 (8.34 g, 19.2 mmol) in DCM (100 mL) was added m-CPBA (6.60 g, 38.4 mmol, 2.00 equiv) in three portions over 15 min. The reaction mixture was allowed to warm to room temperature and maintained for 7 h, or as judged complete by LCMS (ca. 7-8 h). The reaction was quenched by the addition of saturated aq sodium thiosulfate (100 mL) and saturated aq NaHCO$_3$ (100 mL). The reaction mixture was extracted with Et$_2$O (3×75 mL) and the combined organic extracts washed with saturated aq NaHCO$_3$ (3×100 mL) and brine (200 mL). The washed extracts were dried (MgSO$_4$), filtered and concentrated in vacuo. The crude formate was dissolved in MeOH (50 mL) and thionyl chloride (251 μL, 3.44 mmol, 15.0 mol %) was added. The solution was maintained at room temperature for 5 h or until judged complete by LCMS analysis. Upon completion, silica gel (~10.0 g) was added and the reaction mixture was concentrated in vacuo. The silica was dry loaded and purified by flash column chromatography (silica gel, gradient elution, 0-20% EtOAc in hexanes) to afford 4.75 g (60%) of 6 as a yellow oil: $R_f$ 0.45 (4:1 EtOAc/hexanes); IR (thin-film): 3397, 2980, 1693, 1593 cm$^{-1}$; $^1$H NMR (400 MHZ, CDCl$_3$) δ 7.31 (s, 2H), 6.92 (d, J=2.8 Hz, 1H), 6.51 (dd, J=8.0, 2.8 Hz, 1H), 6.42 (d, J=8.0 Hz, 1H), 6.16 (s, 1H, exchanges with D$_2$O), 5.29-5.20 (m, 1H), 4.58-4.48 (m, 2H), 1.38 (d, J=6.0 Hz, 6H), 1.19 (d, J=6 Hz, 12H); $^{13}$C NMR (100 MHz, CDCl$_3$) δ 166.4, 151.4, 151.0, 148.1, 140.8, 127.1, 123.3, 117.0, 116.7, 114.1, 110.7, 72.3, 69.2, 22.0; LRMS calculated for $C_{22}H_{27}ClO_6^+$ [M+H]$^+$ m/z 423.1, measured LC/MS (ESI) $R_f$ 0.742 min, m/z 423.6 [M+H]$^+$.

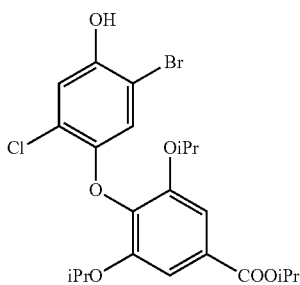

S8

To a solution of phenol 6 (4.00 g, 9.50 mmol) in methanol (24.0 mL) maintained in the dark was added a solution of NBS (1.68 g, 9.50 mmol, 1.01 equiv) in methanol (57.0 mL) over 30 min. After the completion of the addition, the reaction was maintained at room temperature until judged complete by LCMS analysis (ca. 5-10 min), then concentrated in vacuo. The crude residue was purified by column chromatography (silica gel, DCM) to afford 2.80 g (60%) of bromide S8 as a white solid: $R_f$ 0.45 (4:1 hexanes/EtOAc), IR (thin-film): 3376, 2977, 1696, 1590 cm$^{-1}$; $^1$H NMR (400 MHZ, CDCl$_3$) δ 7.32 (s, 2H), 7.10 (s, 1H), 6.67 (s, 1H), 5.34 (s, 1H, exchanges with D$_2$O), 5.28-5.22 (m, 1H), 4.61-4.55 (m, 2H), 1.39 (d, J=6.4 Hz, 6H), 1.24 (d, J=6.0 Hz, 12H); $^{13}$C NMR (100 MHZ, CDCl$_3$) δ 165.8, 151.3, 148.4, 147.5, 139.9, 127.9, 123.5, 118.8, 117.0, 110.3, 107.4, 72.2, 68.9, 22.0; LRMS calculated for $C_{22}H_{26}BrClO_6^+$ [M+H]$^+$ m/z 501.0, measured LC/MS (ESI) $R_f$ 0.869 min, m/z 501.5 [M+H]$^+$.

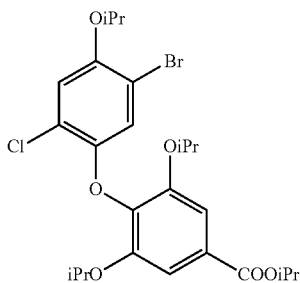

S9

To a solution of phenol S8 (3.50 g, 7.00 mmol) in DMF (2.50 mL) was added potassium carbonate (1.90 g, 14.0 mmol, 2.00 equiv), Bu$_4$NI (510 mg, 1.40 mmol, 10.0 mol %) and 2-bromopropane (1.30 mL, 14.0 mmol, 2.00 equiv). The reaction was maintained at room temperature for 18 h, before dilution with water (15.0 mL). The reaction mixture was extracted with ether (3×15 mL), washed with saturated aq NH$_4$Cl (15 mL) and brine (15 mL), dried (MgSO$_4$), filtered and concentrated in vacuo. The crude residue was purified by column chromatography (silica gel, gradient elution, 0-10% EtOAc in hexanes) to afford 3.30 g (87%) of S9 as a white solid: $R_f$ 0.45 (4:1 hexanes/EtOAc); IR (thin-film): 2979, 1714, 1591, 1474 cm$^{-1}$; $^1$H NMR (400 MHZ, CDCl$_3$) δ 7.31 (s, 2H), 7.00 (s, 1H), 6.75 (s, 1H), 5.28-5.21 (m, 1H), 4.61-4.55 (m, 2H), 4.47-4.41 (m, 1H), 1.38 (d, J=6.4 Hz, 6H), 1.36 (d, J=6.0 Hz, 6H), 1.23 (d, J=6.0 Hz, 12H); $^{13}$C NMR (100 MHZ, CDCl$_3$) δ 165.7, 151.2, 149.7, 148.8, 139.7, 127.9, 122.2, 120.4, 118.4, 112.1, 110.2, 73.8, 72.0, 68.8, 22.1, 22.0; LRMS calculated for $C_{25}H_{32}BrClO_6^+$ [M+H]$^+$ m/z 543.1, measured LC/MS (ESI) $R_f$ 1.18 min, m/z 543.6 [M+H]$^+$.

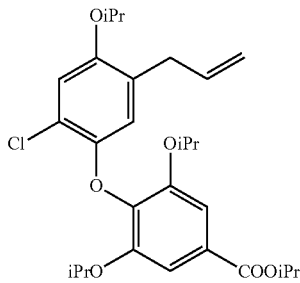

7

To a degassed solution of bromide S9 (2.57 g, 4.72 mmol), cesium fluoride (2.86 g, 18.8 mmol, 4.00 equiv) and allyl-Bpin (1.42 mL, 7.55 mmol, 1.60 equiv) in THF (20.0 mL) was added Pd (Ph$_3$P)$_4$ (382 mg, 0.330 mmol, 7.00 mol %). The reaction mixture was heated and maintained at 85° C. for 7 h, then allowed to cooled to room temperature. The reaction mixture was diluted with ether (20 mL) followed by water (30 mL), and extracted with ether (3×10 mL). The extracts were combined, washed with saturated aq NH$_4$Cl (2×10 mL) and brine (15 mL), dried (MgSO$_4$), filtered and concentrated in vacuo. The crude residue was purified by column chromatography (silica gel, gradient elution, 0-5% EtOAc in hexanes) to afford 2.15 g (86%) of 7 as a clear oil: $R_f$ 0.46 (9:1 hexanes/EtOAc); IR (neat) 2977, 2253, 1722, 1588 cm$^{-1}$; $^1$H NMR (400 MHZ, CDCl$_3$) & 7.30 (s, 2H), 6.90 (s, 1H), 6.38 (s, 1H), 5.81-5.74 (m, 1H), 5.24 (m, 1H), 4.93-4.89 (m, 2H), 4.59-4.53 (m, 2H), 4.44-4.41 (m, 1H), 3.17 (d, J=6.8 Hz, 2H), 1.38 (d, J=6.0 Hz, 6H), 1.30 (d, J=6.0 Hz, 6H), 1.20 (d, J=6.0 Hz, 12H); $^{13}$C NMR (100 MHz, CDCl$_3$) δ 165.8, 151.4, 150.5, 148.0, 140.7, 136.4, 129.2, 127.3, 120.5, 117.6, 115.7, 115.5, 110.5, 72.0, 71.4, 68.7, 34.1, 22.1, 22.0; LRMS calculated for $C_{28}H_{37}ClO_6^+$ [M+H]$^+$ m/z 505.2, measured LC/MS (ESI) $R_f$ 1.23 min, m/z 505.6 [M+H]$^+$.

S10

[Structure: aryl ether with OiPr, Cl, allyl, OiPr, iPrO, CH₂OH substituents]

To a solution of ester 7 (1.52 g, 3.00 mmol) in DCM (15.0 mL) at −78° C. was added DIBALH (7.52 mL, 7.52 mmol, 1 M in hexanes, 2.50 equiv) dropwise. The reaction was maintained at −78° C. for 1 h, allowed to warm to −10° C. and stir for an additional 20 min, then slowly quenched by the addition of saturated aq Rochelle's salt (20.0 mL). The biphasic solution was allowed to stir at room temperature for 18 h. The reaction was extracted with DCM (3×25 mL). The combined organic extracts were washed with brine (40 mL), dried (MgSO₄), filtered and concentrated in vacuo. The crude residue was purified by flash column chromatography (silica gel, gradient elution, 0-20% EtOAc in hexanes) to afford 1.08 g (80%) of S10 as a clear oil: $R_f$ 0.25 (2:1 hexanes/EtOAc); IR (thin-film) 3403, 3077, 2363, 1640, 1593 cm$^{-1}$; $^1$H NMR δ 6.89 (s, 1H), 6.59 (s, 2H), 6.39 (s, 1H), 5.80-5.73 (m, 1H), 4.90-4.86 (m, 2H), 4.56 (s, 2H), 4.49-4.38 (m, 4H), 3.15 (d, J=6.4 Hz, 2H), 2.82 (s, 1H, exchanges with D₂O), 1.26 (d, J=6.0 Hz, 6H), 1.15 (d, J=6.0 Hz, 12H); $^{13}$C NMR (100 MHz, CDCl₃) δ 151.5, 150.0, 148.2, 138.0, 136.4, 135.6, 128.9, 120.0, 117.2, 115.6, 115.3, 107.8, 71.7, 71.3, 64.9, 34.1, 22.04, 22.02; LRMS calculated for $C_{25}H_{33}ClO_5^+$ [M+H]$^+$ m/z 449.2, measured LC/MS (ESI) $R_f$ 0.895 min, m/z 449.0 [M+H]$^+$.

S11

[Structure: aryl ether with OiPr, Cl, allyl, OiPr, iPrO, CH₂Cl substituents]

To a solution of alcohol S10 (2.57 g, 6.54 mmol) in acetonitrile (32.0 mL) was added diisopropylethylamine (1.13 mL, 19.6 mmol, 3.00 equiv). The solution was cooled to 0° C., maintained for 10 min before triphenylphosphine dichloride (7.62 g, 22.8 mmol, 3.50 equiv) was added in one portion. The reaction mixture was maintained at 0° C. for 30 min, at which time it was judged complete by TLC (20-30 min). The reaction mixture was loaded directly on to a silica gel column for purification (gradient elution, 0-20%, EtOAc in hexanes) to afford 2.40 g (90%) of chloride S11 as a white solid: $R_f$ 0.64 (9:1 hexanes/EtOAc); IR (thin-film): 2977, 1594, 1487 cm$^{-1}$; $^1$H NMR (400 MHZ, CDCl₃) δ 6.92 (s, 1H), 6.66 (s, 2H), 6.43 (s, 1H), 5.81-5.76 (m, 1H), 4.94-4.90 (m, 2H), 4.52 (s, 2H), 4.51-4.47 (m, 2H), 4.41-4.39 (m, 1H), 3.20 (d, J=6.4 Hz, 2H), 1.28 (d, J=6.0 Hz, 6H), 1.17 (d, J=6.0 Hz, 12H); $^{13}$C NMR (150 MHz, CDCl₃) δ 151.5, 150.0, 148.0, 136.3, 136.2, 134.0, 128.8, 120.0, 117.2, 115.3, 115.2, 109.3, 71.5, 71.1, 46.4, 33.9, 21.9, 21.8; LRMS calculated for $C_{25}H_{32}Cl_2O_4^+$ [M+H]$^+$ m/z 467.1, measured LC/MS (ESI) $R_f$ 1.13 min, m/z 467.0 [M+H]$^+$.

S12

[Structure: aryl ether with OiPr, Cl, allyl, OiPr, iPrO, CH₂-C≡C-TMS substituents]

To freshly distilled ethynyltrimethylsilane (1.94 mL, 13.9 mmol, 5.00 equiv) in THF (5.00 mL) at 0° C. was added ethylmagnesium chloride (5.56 mL, 11.1 mmol, 2 M in THF, 4.00 equiv) dropwise. The reaction was allowed to warm to room temperature and maintained for 1 h and CuBr (596 mg, 4.17 mmol, 1.50 equiv) was then added. The suspension was maintained at room temperature for an additional hour, before the addition of chloride S11 (1.30 g, 2.78 mmol) as a solution in THF (10 mL). The reaction mixture was heated and maintained at 65° C. for 24 h. Upon completion of the reaction as judged by TLC (ca. 24 h) the reaction was allowed to cool to room temperature and quenched by the addition of saturated aq NH₄Cl (15 mL). The reaction mixture was extracted with ether (3×25 mL). The combined organic extracts were washed with saturated aq NH₄Cl (2×25 mL), brine (25 mL), dried (MgSO₄), filtered and concentrated in vacuo. The crude residue was purified by flash column chromatography (silica gel, gradient elution, 0-2% EtOAc in hexanes) to afford 1.35 g (92%) of alkyne S12 as a yellow oil: $R_f$ 0.72 (9:1 hexanes/EtOAc); IR (thin-film): 2177, 1594, 1486 cm$^{-1}$; $^1$H NMR (400 MHZ, CDCl₃) δ 6.90 (s, 1H), 6.64 (s, 2H), 6.41 (s, 1H), 5.85-5.75 (m, 1H), 4.94-4.90 (m, 2H), 4.51-4.40 (m, 3H), 3.62 (s, 2H), 3.19 (d, J=6.4 Hz, 2H), 1.30 (d, J=6.0 Hz, 6H), 1.20 (d, J=6.0 Hz, 12H), 0.21 (s, 9H); $^{13}$C NMR (100 MHZ, CDCl₃) δ 151.5, 150.0, 148.3, 136.5, 135.1, 132.9, 129.0, 120.0, 117.2, 115.6, 115.3, 109.0, 104.3, 87.4, 71.7, 71.3, 34.2, 26.2, 22.15, 22.12, 0.12; LRMS calculated for $C_{30}H_{41}ClO_4Si^+$ [M+H]$^+$ m/z 529.2, measured LC/MS (ESI) $R_f$ 1.39 min, m/z 529.0 [M+H]$^+$.

8

[Structure: aryl ether with iPrO, Cl, allyl, OiPr, iPrO, CH₂-C≡CH substituents]

To a solution of alkynylsilane S12 (1.35 g, 2.55 mmol) in MeOH (7.00 mL) and THF (0.700 mL) was added a solution of NaOMe (0.165 mL, 0.142 mmol, 0.86 M in MeOH, 5.00 mol %). The reaction was allowed to stir at room temperature until judge complete by TLC (ca. 5 h), then concentrated in vacuo. The crude residue was purified by flash column chromatography (silica gel, gradient elution, 0-4% EtOAc in hexanes) to afford 1.03 g (88%) of 8 as a yellow oil: $R_f$ 0.58 (9:1 hexanes/EtOAc); IR (neat) 3297, 1593, 1484 cm$^{-1}$; $^1$H NMR (400 MHZ, CDCl$_3$) δ 6.90 (s, 1H), 6.62 (s, 2H), 6.40 (s, 1H), 5.83-5.74 (m, 1H), 4.93-4.90 (m, 2H), 4.52-4.46 (m, 2H), 4.43-4.40 (m, 1H), 3.57 (d, J=2.4 Hz, 2H), 3.18 (d, J=6.4 Hz, 2H), 2.22 (t, J=2.8 Hz, 1H), 1.30 (d, J=6.0 Hz, 6H), 1.19 (d, J=6.0 Hz, 12H); $^{13}$C NMR (100 MH, CDCl$_3$) δ 151.7, 150.2, 148.4, 136.7, 135.5, 132.7, 129.1, 120.1, 117.3, 115.7, 115.4, 109.3, 81.9, 72.0, 71.5, 70.8, 34.2, 25.0, 22.26, 22.21; LRMS calculated for $C_{27}H_{33}ClO_4^+$ [M+H]$^+$ m/z 457.2, measured LC/MS (ESI) $R_f$ 1.12 min, m/z 457.0 [M+H]$^+$.

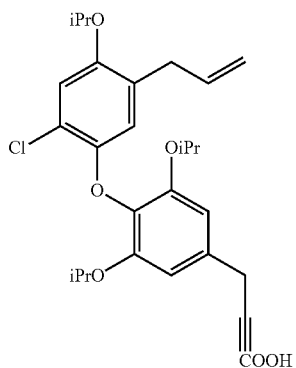

S13

A solution of alkyne 8 (1.01 g, 2.21 mmol) in THF (30.0 mL) was cooled to −78° C. and a solution of n-BuLi (0.930 mL, 2.23 mmol, 2.4 M in hexanes, 1.01 equiv) added dropwise over 10 min. The reaction mixture was allowed to stir at −78° C. for 5 min, then carbon dioxide was bubbled through the solution while it was allowed to slowly warm to room temperature over 2 h. The reaction was maintained at room temperature until judge complete by LCMS (ca. 1 h), followed by acidification with 1M HCl (3 mL, 1 M). The acidified reaction mixture was extracted with EtOAc (4×20 mL), the organic extracts were combined, dried (MgSO$_4$), filtered and concentrated in vacuo. The crude residue was purified by flash column chromatography (silica gel, gradient elution, 0-30% MeOH in DCM) to afford 0.962 g (87%) of carboxylic acid S13 as a off-white foam: $R_f$ 0.46 (4:1 DCM/Methanol); IR (thin-film): 3411-3074, 2985, 2243, 1710, 1061 cm$^{-1}$; $^1$H NMR (400 MHz, CDCl$_3$) δ 9.83 (br s, 1H, exchanges with D$_2$O), 6.90 (s, 1H), 6.57 (s, 2H), 6.38 (s, 1H), 5.82-5.75 (m, 1H), 4.91-489 (m, 2H), 4.52-4.40 (m, 3H), 3.71 (s, 2H), 3.18 (d, J=6.4 Hz, 2H), 1.30 (d, J=6.0 Hz, 6H), 1.18 (d, J=6.0 Hz, 12H); $^{13}$C NMR (100 MHZ, CDCl$_3$) δ 151.9, 150.2, 148.3, 136.6, 135.8, 130.5, 129.2, 120.1, 117.3, 115.8, 115.5, 109.4, 72.1, 71.5, 34.2, 25.3, 22.2, 22.1; LRMS calculated for $C_{28}H_{33}ClO_6^+$ [M+H]$^+$ m/z 501.2, measured LC/MS (ESI) $R_f$ 0.895 min, m/z 501.5 [M+H]$^+$.

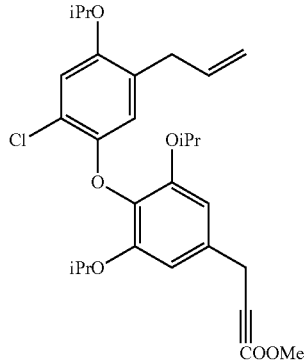

S14

To a solution of carboxylic acid S13 (953 mg, 1.90 mmol, 1.00 equiv) in MeOH (5.00 mL) was added thionyl chloride (69.0 μL, 0.951 mmol, 0.500 equiv). The reaction was allowed to stir at room temperature for 4 h, then concentrated in vacuo. The crude residue was purified by flash column chromatography (silica gel, gradient elution, 0-20% EtOAc in hexanes) to afford 0.891 g (91%) of methyl ester S14 as a white foam: $R_f$ 0.5 (4:1 hexanes/EtOAc); IR (thin-film): 3072, 2977, 2240, 1716, 1594 cm$^{-1}$; $^1$H NMR (400 MHZ, CDCl$_3$) δ 6.89 (s, 1H), 6.57 (s, 2H), 6.38 (s, 1H), 5.82-5.75 (m, 1H), 4.50-4.40 (m, 3H), 3.79 (s, 3H), 3.70 (s, 2H), 3.18 (d, J=6.88 Hz, 2H), 1.30 (d, J=6.0 Hz, 6H), 1.19 (d, J=6.0 Hz, 12H); $^{13}$C NMR (100 MHZ, CDCl$_3$) δ 154.2, 151.9, 150.2, 148.3, 136.6, 135.8, 130.7, 129.2, 120.1, 117.3, 115.7, 115.4, 109.4, 86.7, 74.8, 72.0, 71.5, 52.8, 34.2, 25.2, 22.2, 22.1; LRMS calculated for $C_{29}H_{35}ClO_6^+$ [M+H]$^+$ m/z 515.2, measured LC/MS (ESI) $R_f$ 1.10 min, m/z 515.6 [M+H]$^+$.

9

To suspension of CuCN (200 mg, 2.24 mmol, 1.20 equiv) in THF (7.50 mL) at −78° C. was added a solution of n-BuLi (1.87 mL, 4.49 mmol, 2.4 M in hexanes, 2.40 equiv) dropwise. The mixture was warmed to −40° C., maintained for 10 min and then cooled to −78° C. The warming and cooling process is repeated until a homogenous solution is obtained (ca. 3 cycles), to the −78° C. solution, neat Bu$_3$SnH (1.20 mL, 4.49 mmol, 2.40 equiv) was then added dropwise and the reaction was maintained at −78° C. for 35 minutes (bright yellow solution). A solution of alkynoate S14 (890 mg, 1.72 mmol, 1.00 equiv) in MeOH (7.40 mL, 4.79 mmol, 0.65 M in THF, 2.79 equiv) was then added dropwise over 10 min. The reaction mixture was maintained at −78° C. until judged complete by TLC (ca. 1.5 h), then quenched at −78° C. with saturated aq NH$_4$Cl (10 mL). The reaction mixture was allowed to warm to room temperature and stirred until the aqueous layer achieved a deep blue color (ca. 2 h). The reaction was extracted with ether (3×25 mL), the combined organic extracts were washed with saturated aq NH₄Cl (2×15 mL) and brine (10 mL). The washed extracts were dried (MgSO₄), filtered and concentrated in vacuo. The crude residue was purified by flash column chromatography (Silica gel/K₂CO₃ (10:1); gradient elution, 0-3% EtOAc in hexanes) to afford 1.10 g (77%) of 9 as a clear oil: R$_f$ 0.73 (4:1 hexanes/EtOAc); IR (thin-film): 3073, 2926, 1715, 1593, 1488 cm$^{-1}$; $^1$H NMR (400 MHZ, CDCl₃) δ 6.89 (s, 1H), 6.42 (s, 2H), 6.39 (s, 1H), 6.11 (s, J$_{Sn-H}$=30 Hz, 1H), 5.84-5.74 (m, 1H), 4.93-4.89 (m, 2H), 4.46-4.39 (m, 3H), 4.20 (s, J$_{Sn-H}$=27 Hz, 2H), 3.75 (s, 3H), 3.17 (d, J=6.4 Hz, 2H), 1.404-137 (m, 6H), 1.37 (d, J=6.0 Hz, 6H), 1.28-1.22 (m, 7H), 1.17 (d, J=6.0 Hz, 12H), 0.88-0.84 (app t, J=7.2 Hz, 9H), 0.81-0.77 (m, 5H); $^{13}$C NMR (100 MHz, CDCl₃) δ 170.9, 165.0, 151.7, 150.1, 148.5, 136.7, 136.0, 135.3, 129.1, 128.0, 120.1, 117.4, 115.8, 115.3, 110.5, 71.8, 71.5, 51.1, 41.1, 34.4, 29.0, 27.4, 22.2, 13.7, 10.3; HRMS (ESI-orbitrap MS) calculated for C₄₁H₆₃ClO₆Sn⁺ [M+H]⁺ m/z=807.3408, measured 807.3431.

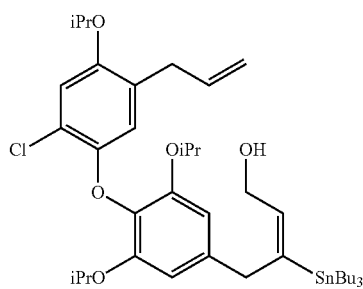

S15

To −78° C. solution of enoate 9 (1.05 g, 1.30 mmol) in DCM (26.0 mL) was added a solution of DIBAL (3.25 mL, 3.25 mmol, 1M in hexanes, 2.50 equiv). The reaction mixture was maintained at −78° C. for 1 h, then an additional equivalent of DIBAL (1.30 mL, 1.30 mmol, 1M in hexanes, 1.00 equiv) was added. The reaction was maintained at −78° C. for 10 min, then allowed to warm to −10° C. for 20 min. The reaction was quenched slowly by the addition of saturated aq Rochelle's salt (15 mL) and the biphasic solution was allowed to stir for 18 h. The reaction mixture was extracted with DCM (3×25 mL) and the combined organic extracts were washed with brine (30 mL). The washed extracts were dried (MgSO₄), filtered and concentrated in vacuo. The crude residue was purified by flash column chromatography (silica gel (2% Et₃N buffered); gradient elution, 0-30% EtOAc in hexanes) to afford 0.838 g (82%) of alcohol S15 as a clear oil: R$_f$ 0.20 (9:1 hexane/EtOAc); IR (thin-film): 3419, 3070, 2925, 1590, 1474 cm$^{-1}$; $^1$H NMR (400 MHZ, CDCl₃) δ 6.89 (s, 1H), 6.39 (s, 3H), 5.95 (t, J=6.1 Hz, J$_{Sn-H}$=33 Hz, 1H), 5.84-5.74 (m, 1H), 4.93-4.88 (m, 2H), 4.47-4.40 (m, 3H), 4.35 (app t, J=5.1 Hz, 2H), 3.60 (s, J$_{Sn-H}$=27 Hz, 2H), 3.17 (d, J=6.4 Hz, 2H), 1.45-1.37 (m, 7H), 1.30 (d, J=6.0 Hz, 6H), 1.29-1.21 (m, 6H), 1.18 (d, J=6.0 Hz, 12H), 0.86 (t, J=7.2 Hz, 9H), 0.79-0.74 (m, 5H); $^{13}$C NMR (100 MHz, CDCl₃) δ 151.6, 150.1, 148.4, 146.3, 140.1, 136.9, 136.7, 135.1, 129.1, 120.1, 117.3, 115.8, 115.3, 110.5, 110.2, 71.9, 71.5, 59.3, 39.5, 34.3, 29.2, 27.5, 13.8, 9.9; HRMS (ESI-orbitrap MS) calculated for C₄₀H₆₃ClO₅Sn⁺ [M+H]⁺ 779.3459, measured 761.3375 [M-H₂O]⁺.

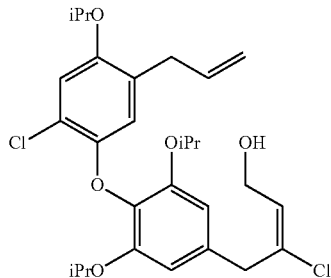

10

To a 0° C. solution of stannane S15 (779 mg, 1.00 mmol) in THF (20.0 mL) was added CuCl₂ (2.69 g, 20.0 mmol, 20.0 equiv). The reaction mixture was allowed to warm to room temperature and maintained for 18 h, or until judged complete by TLC analysis (ca. 18-24 h). The suspension was quenched with saturated aq NH₄Cl (25 mL) and extracted with ether (3×25 mL). The combined organic extracts were washed with saturated aq NH₄Cl (2×20 mL) and brine (20 mL). The washed extracts were dried (Na₂SO₄), filtered, and concentrated in vacuo. The crude residue was purified by flash column chromatography (Silica gel/K₂CO₃ (10:1), gradient elution, 0-30% EtOAc in hexanes) to afford 0.458 g (85%) of chloride 10 as a clear oil: R$_f$ 0.25 (4:1 hexanes/EtOAc); IR (thin-film): 3417, 2977, 2358, 1644, 1594 cm$^{-1}$; $^1$H NMR (400 MHZ, CDCl₃) δ 6.90 (s, 1H), 6.50 (s, 2H), 6.39 (s, 1H), 6.0 (t, J=7.2 Hz, 1H), 5.81-5.74 (m, 1H), 4.93-4.89 (m, 2H), 4.50-4.40 (m, 3H), 4.26 (d, J=7.2 Hz, 2H), 3.67 (s, 2H), 3.18 (d, J=6.4 Hz, 2H), 1.30 (d, J=6.0 Hz, 6H), 1.18 (d, J=6.0 Hz, 12H); $^{13}$C NMR (100 MHZ, CDCl₃) δ 151.6, 150.2, 148.3, 136.7, 136.6, 135.7, 133.6, 129.1, 127.9, 120.1, 117.3, 115.8, 115.5, 110.3, 72.0, 71.5, 59.1, 40.4, 34.1, 22.2, 22.1; LRMS calculated for C₂₈H₃₆Cl₂O₅ [M+Na] m/z 545.2, measured LC/MS (ESI) R$_f$ 1.01 min, m/z 545.6 [M+Na].

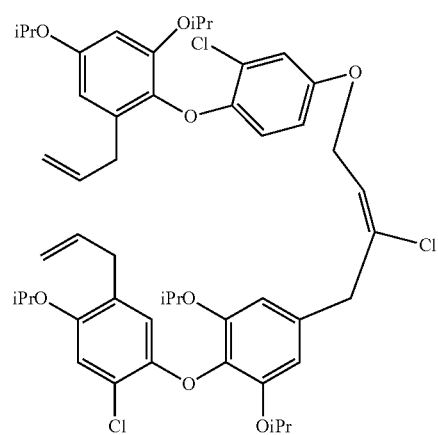

S16

To a 0° C. solution of alcohol 10 (368 mg, 0.704 mmol), phenol 4 (395 mg, 1.05 mmol, 1.50 equiv) and Ph₃P (277 mg, 1.05 mmol, 1.50 equiv) in DCM (3.50 mL) at was added a solution of diethyl azodicarboxylate (478 µL, 1.05 mmol, 40 wt. % in toluene, 1.50 equiv) at a rate of ca. 1 drop every 2 min. Following the addition, the reaction mixture was maintained at 0° C. for 30 min, allowed to warm to room temperature and maintained until judged complete by TLC (ca. 15-30 min). The reaction mixture was loaded directly onto a silica gel column and purified (gradient elution, 0-10% EtOAc in hexanes) to afford 430 mg (69%) of ether S16 as a yellow oil: $R_f$ 0.56 (4:1 hexanes/EtOAc); IR (thin-film): 3073, 2976, 2927, 1739, 1640, 1594 cm$^{-1}$; $^1$H NMR (400 MHZ, CDCl$_3$) δ 6.99 (d, J=2.8 Hz, 1H), 6.90 (s, 1H), 6.61 (dd, J=9.0, 2.8 Hz, 1H), 6.51 (s, 2H), 6.46 (d, J=9.0 Hz, 1H), 6.40 (m, 3H), 6.09 (t, J=7.0 Hz, 1H), 5.91-5.72 (m, 2H), 5.06-5.02 (m, 2H), 4.93-4.88 (m, 2H), 4.55 (d, J=7.0 Hz, 2H), 4.51-4.37 (m, 5H), 3.71 (s, 2H), 3.29 (d, J=6.6 Hz, 2H), 3.18 (d, J=6.6 Hz, 2H), 1.34 (d, J=6.0 Hz, 6H), 1.30 (d, J=6.0 Hz, 6H), 1.17 (d, J=6.0 Hz, 12H), 1.14 (d, J=6.0 Hz, 6H); $^{13}$C NMR (100 MHz, CDCl$_3$) δ 155.4, 152.7, 151.7, 151.0, 150.2, 149.2, 148.4, 138.7, 136.9, 136.6, 136.3, 135.8, 135.0, 133.1, 129.2, 123.9, 122.5, 120.1, 117.3, 116.5, 116.3, 115.8, 115.58, 115.52, 113.6, 110.3, 108.6, 103.7, 72.0, 71.7, 71.5, 70.3, 64.8, 40.7, 34.5, 34.2, 29.8, 22.26, 22.22, 22.1, 22.0; LRMS calculated for $C_{49}H_{59}Cl_3O_8^+$ [M+H]$^+$ m/z 881.3, measured LC/MS (ESI) $R_f$ 1.38 min, m/z 881.5 [M+H]$^+$.

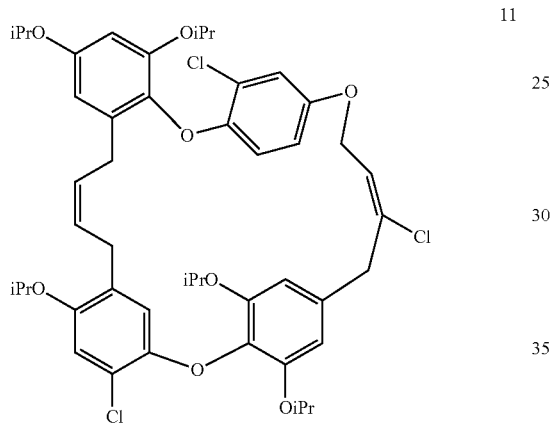

11

To a degassed solution of diene S16 (76.0 mg, 0.086 mmol) in DCE (21.0 mL) was added a solution of Grubbs C633 catalyst (9.00 mg, 0.0140 mmol, 16 mol %) in DCE (1.00 mL). The solution was frozen and placed under vacuum (ca. 0.01 torr) for ca. 10 min, the reaction vessel was sealed under vacuum and allowed to slowly warm to room temperature. Once the flask was at room temperature, the reaction was heated and maintained at 60° C. for 24 h. The reaction was allowed to cool to room temperature and quenched by the addition of ethyl vinyl ether (100 µL). The solution was concentrated in vacuo and purified by flash column chromatography (silica gel, gradient elution, 0-10% EtOAc in hexanes) to afford 43.0 mg (59%) of macrocycle 11 as a white foam: $R_f$ 0.4 (4:1 hexanes/EtOAc); IR (thin-film): 3051, 2976, 2927, 1734, 1647, 1594 cm$^{-1}$; $^1$H NMR (400 MHZ, CDCl$_3$) δ 6.89 (d, J=2.7 Hz, 1H), 6.86 (s, 1H), 6.53 (dd, J=9.0, 2.7 Hz, 1H), 6.55-6.36 (m, 5H), 6.13-6.11 (m, 2H), 5.41-5.33 (m, 2H), 4.48 (d, J=6.8 Hz, 2H), 4.46-4.34 (m, 5H), 3.74 (s, 2H), 3.28 (d, J=6.6 Hz, 2H), 2.98 (d, J=6.0 Hz, 2H), 1.32 (app dd, J=6.0, 2.17 Hz, 12H), 1.24 (d, J=6.0 Hz, 6H), 1.14 (d, J=6.0 Hz, 6H), 1.07 (d, J=6.0 Hz, 6H); $^{13}$C NMR (100 MHZ, CDCl$_3$) δ 155.5, 152.5, 151.8, 151.1, 150.2, 149.4, 148.0, 136.9, 136.3, 135.6, 135.4, 133.0, 129.8, 129.3, 127.1, 125.6, 122.3, 119.6, 117.6, 116.9, 115.5, 115.3, 113.9, 109.8, 108.6, 103.9, 72.1, 71.9, 71.3, 70.3, 65.7, 41.0, 28.9, 27.8, 22.3, 22.24, 22.21, 22.1; LRMS calculated for $C_{47}H_{55}Cl_3O_8^+$ [M+H]$^+$ m/z 854.3, measured LC/MS (ESI) $R_f$ 1.48 min, m/z 854.6 [M+H]$^+$.

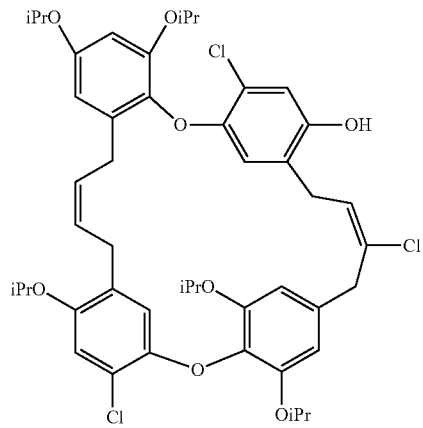

S17

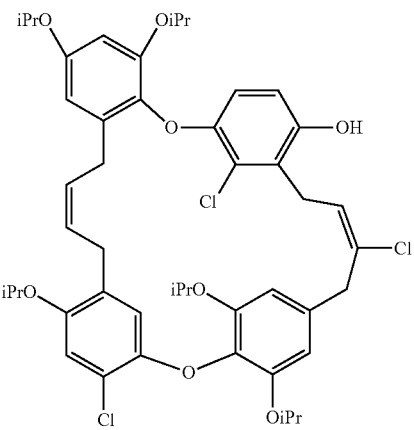

S18

To a solution of ether 11 (41.0 mg, 0.048 mmol, 1.00 equiv) in DCE (3.20 mL) was added BF$_3$·Et$_2$O (0.383 µL, 0.191 mmol, 0.5 M in DCE, 3.00 equiv) dropwise. The reaction was heated and maintained at 70° C. for 2 h, the reaction was allowed to cool to room temperature and quenched with brine (5 mL). The reaction was extracted with EtOAc (3×5 mL), washed with brine (10 mL), dried (MgSO$_4$), filtered and concentrated in vacuo. The crude residue ~19 mg (45%) of an inseparable mixture of phenols S17 and S18 was used in the subsequent step as is: $R_f$ 0.27 (4:1 hexanes/EtOAc); LRMS calculated for $C_{47}H_{55}Cl_3O_8^+$ [M+H]$^+$ m/z 853.3, measured LC/MS (ESI) $R_f$ 1.40 min, m/z 853.0 [M+H]$^+$.

VU0849855

-continued

VU0849838

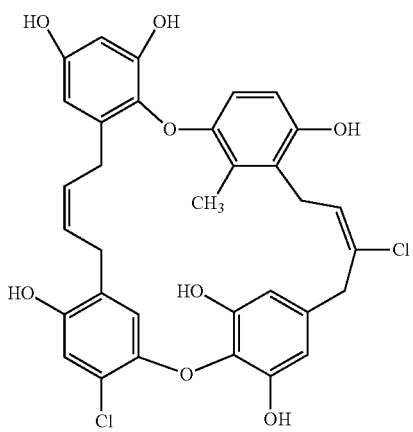

To a −78° C. solution of phenols S17 and S18 (24.0 mg, 0.028 mmol) in DCM (2.80 mL) was added a solution of BCl$_3$ (0.244 mL, 0.244 mmol, 1 M in DCM, 7.00 equiv) dropwise. The reaction mixture was allowed to warm to room temperature over 1 h, and maintained, until judged complete by TLC (ca. 2-4 h). The reaction was diluted with brine (2 mL) and extracted with EtOAc (4×5 mL). The combined organic extracts were washed with brine (5.00 mL), dried (Na$_2$SO$_4$), filtered and concentrated in vacuo. The crude residue (~16 mg) was purified by Gilson preparative HPLC (30-455% CH$_3$CN in H$_2$O, over 8 min) to afford 5.00 mg (27%) of VU0849855 and 6.00 mg (33%) of VU0849838.

VU0849855: R$_f$ 0.55 (5:1 DCM/methanol); $^1$H NMR (600 MHZ, CD$_3$OD) δ 6.85 (s, 1H), 6.78 (s, 1H), 6.29 (s, 1H), 6.25 (d, J=3 Hz, 2H), 6.10-6.05 (m, 4H), 5.60-5.56 (m, 1H), 5.49-5.46 (m, 1H), 3.52 (s, 2H), 3.28 (d, J=6.7 Hz, 2H), 3.22 (d, J=8.0 Hz, 2H), 3.01 (d, J=7.2 Hz, 2H); $^{13}$C NMR (150 MHz, CD$_3$OD) δ 155.8, 151.5, 151.3, 150.6, 150.3, 148.8, 148.3, 136.7, 136.3, 135.0, 134.8, 130.2, 130.0, 128.1, 128.0, 127.8, 127.4, 120.8, 119.4, 117.3, 117.0, 116.6, 116.4, 109.2, 108.0, 103.1, 40.3, 30.3, 28.6, 28.0; LCMS (ESI) R$_f$ 1.39 min, 1.04 min, m/z=643.0 [M+H]$^+$; HRMS (ESI-orbitrap MS) calculated for C$_{32}$H$_{25}$Cl$_3$O$_8$$^+$ [M+H]$^+$ m/z 643.0688, measured 643.0713.

VU0849838: R$_f$ 0.47 (5:1 DCM/methanol); $^1$H NMR (600 MHZ, CD$_3$OD) δ 6.80 (s, 1H), 6.55 (d, J=9.0 Hz, 1H), 6.46 (s, 1H), 6.29-6.28 (m, 3H), 6.26 (d, J=2.6 Hz, 1H), 6.17-6.14 (m, 2H), 5.77-5.73 (m, 1H), 5.46-5.41 (m, 1H), 3.78 (s, 2H), 3.64 (d, J=7.7 Hz, 2H), 3.25 (d, J=7.7 Hz, 2H), 2.96 (d, J=7.6 Hz, 2H); $^{13}$C NMR (150 MHz, CD$_3$OD) δ 156.3, 151.9, 151.5, 150.5, 148.6, 148.1, 137.0, 136.6, 136.5, 134.5, 133.8, 130.3, 130.0, 128.5, 128.2, 127.3, 126.9, 123.2, 119.7, 116.9, 116.4, 113.9, 113.4, 109.2, 108.4, 102.6, 40.9, 28.9, 28.2, 28.1; LCMS (ESI) R$_f$ 1.09 min, m/z=643.0 [M+H]$^+$; HRMS (ESI-orbitrap MS) calculated for C$_{32}$H$_{25}$Cl$_3$O$_8$$^+$ [M+H]$^+$ m/z 643.0688, measured 643.0711.

Example 2 Preparation of VU0848355 and VU0848354

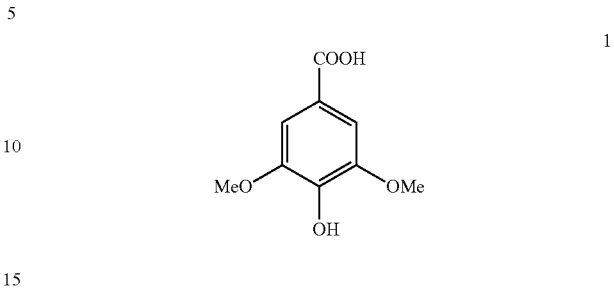

1

To a suspension of 4-hydroxy-3,5-dimethoxybenzoic acid (5.0 g, 25.2 mmol) in methanol (51 mL) was added thionyl chloride (1.38 mL, 18.9 mmol, 0.75 equiv) dropwise. The reaction mixture was heated and maintained at 50° C. for 18 h. The reaction mixture was allowed to cool to room temperature before the addition of silica gel (ca. 10 g). The slurry was concentrated in vacuo and loaded onto a silica gel column and purified by column chromatography (gradient, 20 to 50% EtOAc in hexanes) to afford 5.11 g (96%) of 1 as a white solid: $^1$H NMR (400 MHZ, CDCl$_3$) δ 7.32 (s, 2H), 5.93 (s, 1H), 3.94 (s, 6H), 3.90 (s, 3H); $^{13}$C NMR (100 MHz, CDCl$_3$): 166.9, 146.8, 139.3, 121.2, 106.7, 56.5, 52.2.

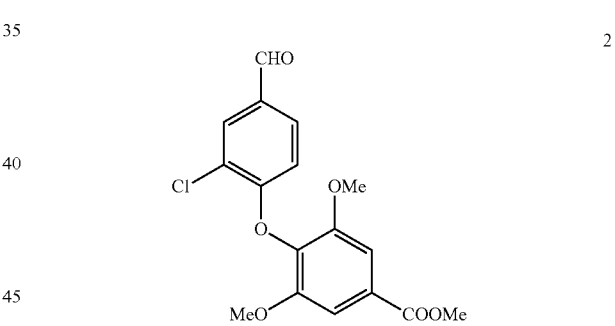

2

To a solution of phenol 1 (4.97 g, 23.4 mmol) in DMF (78 mL) was added K$_2$CO$_3$ (6.47 g, 46.8 mmol, 2 equiv) followed by 3-chloro-4-fluorobenzaldehyde (3.71 g, 23.4 mmol, 1 equiv). The reaction mixture was heated and maintained at 120° C. for 24 h. The suspension was allowed to cool to room temperature and diluted with water (200 mL). The reaction mixture was extracted with EtOAc (3×25 mL), washed with saturated aq NH$_4$Cl (2×50 mL) and brine (30 mL). The organic layers were dried (MgSO$_4$), filtered and concentrated in vacuo. The crude solid was recrystallized from hot methanol/water to afford 6.1 g (75%) of 2 as a white solid: R$_f$ 0.25 (4:1 hexanes/EtOAc); IR (thin-film): 2951, 2842, 1708, 1596, 1239 cm$^{-1}$; $^1$H NMR (400 MHZ, CDCl$_3$) δ 9.87 (s, 1H), 7.97 (d, J=2.0 Hz, 1H), 7.60 (dd, J=8.5 Hz, 2.0 Hz, 1H), 7.39 (s, 2H), 6.62 (d, J=8.5 Hz, 1H), 3.96 (s, 3H), 3.84 (s, 6H); $^{13}$C NMR (100 MHz, CDCl$_3$): 189.8, 166.4, 158.5, 152.8, 135.0, 132.0, 131.7, 129.7, 128.4, 123.7, 114.6, 106.9, 56.6, 52.6; LRMS calculated for C$_{17}$H$_{16}$ClO$_6$$^+$ [M+H]$^+$ m/z 351.0, measured LC/MS (ESI) R$_f$ 0.332 min, m/z 351.4 [M+H]$^+$.

3

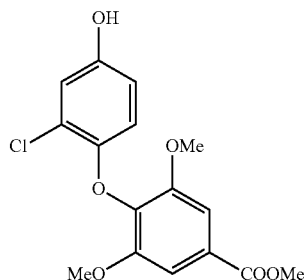

To a 0° C. solution of aldehyde 2 (7.65 g, 21.8 mmol) in DCM (110 mL) was added mCPBA (10.7 g, 46.9 mmol, 2 equiv) in three portions over 15 minutes, after which the reaction was allowed to warm to room temperature and stir for 7 h. The reaction was quenched by the addition of saturated aq $Na_2S_2O_3$ (100 mL) and saturated aq $NaHCO_3$ (100 mL), followed by extraction with $Et_2O$ (3×100 mL). The combined organic extracts were washed with saturated aq $NaHCO_3$ (2×100 mL), water (100 mL) and brine (100 mL), dried ($MgSO_4$), filtered, and concentrated in vacuo. The crude formate was dissolved in MeOH (40 mL, 0.5 M) and THF (10 mL), then thionyl chloride (1.31 mL, 16.1 mmol, 0.75 equiv) was added dropwise. The solution was maintained at room temperature for 7 h, before the addition of silica gel (ca. 10 g). The mixture was concentrated in vacuo and purified by column chromatography (DCM) to afford 6.03 g (82%) of 3 as a white solid: $R_f$: 0.23 (2:1 hexanes/EtOAc); IR (thin-film): 3327, 2944, 1672, 1596 cm$^{-1}$; $^1$H NMR (400 MHZ, $(CD_3)_2CO$) δ 8.30 (s, 1H, exchanges with $D_2O$), 7.39 (s, 2H), 6.93 (d, J=2.8 Hz, 1H), 6.60 (dd, J=8.8, 2.8 Hz, 1H), 6.40 (d, J=9.2 Hz, 1H), 3.90 (s, 3H), 3.82 (s, 6H); $^{13}$C (100 MHZ, $(CD_3)_2CO$) δ 166.7, 154.1, 153.2, 147.9, 137.3, 128.2, 122.6, 117.5, 116.0, 115.1, 107.6, 56.7, 52.5; LRMS calculated for $C_{16}H_{16}ClO_6^+$ [M+H]$^+$ m/z 339.0, measured LC/MS (ESI) $R_f$ 0.973 min, m/z 339.3 [M+H]$^+$.

4

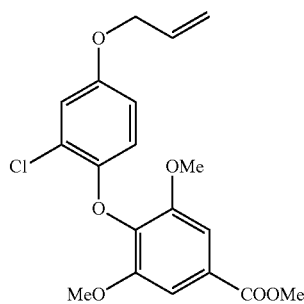

To a solution of phenol 3 (4.02 g, 11.8 mmol) in DMF (47 mL) was added $Cs_2CO_3$ (5.80 g, 17.8 mmol, 1.5 equiv) and $Bu_4NI$ (0.438 g, 1.18 mmol, 0.1 equiv). The suspension was allowed to stir for 10 min before allyl bromide (1.34 mL, 15.4 mmol, 1.5 equiv) was added. The reaction mixture was maintained at room temperature for 18 h, before dilution with water (100 mL) and extraction with EtOAc (3×50 mL). The combined organic layers were washed with water (2×100 mL) and brine (100 mL), dried ($MgSO_4$), filtered and concentrated in vacuo. The crude residue was purified by column chromatography (gradient, 0 to 15%, EtOAc in hexanes) to afford 4.13 g (92%) of 4 as a white solid: $R_f$: 0.28 (4:1 hexanes/EtOAc); IR (thin film): 1720; $^1$H NMR (400 MHZ, CDCl$_3$) § 7.36 (s, 2H), 6.9 (d, J=2.9 Hz, 1H), 6.62 (dd, J=9.0, 2.9 Hz, 1H), 6.45 (d, J=9.0 Hz, 1H), 6.02 (m, 1H), 5.40 (dd, J=16 Hz, 1.5 Hz, 1H), 5.28 (dd, J=, 1H), 4.46 (d, J=3.8 Hz, 2H), 3.94 (s, 3H), 3.83 (s, 6H); $^{13}$C NMR (100 MHz, CDCl$_3$) δ 166.6, 153.7, 153.1, 148.1, 136.9, 133.1, 127.2, 122.8, 117.9, 116.7, 115.3, 113.9, 107.0, 69.6, 56.6, 52.5; LRMS calculated for $C_{19}H_{20}ClO_6^+$ [M+H]$^+$ m/z 379.0, measured LC/MS (ESI) $R_f$ 1.18 min, m/z 379.3 [M+H]$^+$.

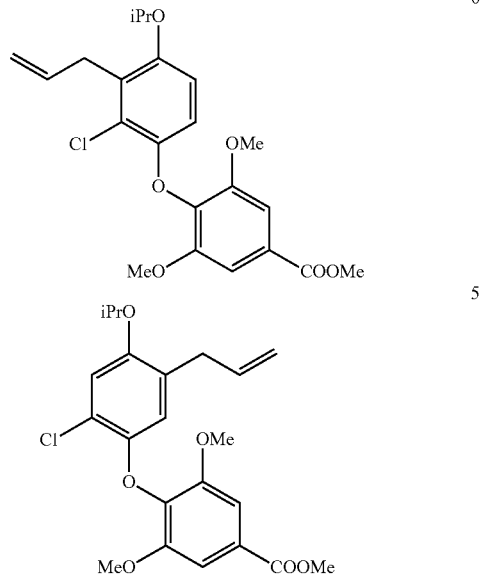

To a −78° C. solution of allyl ether 4 (3.5 g, 9.24 mmol) in DCM (92 mL) was added BCl$_3$ (15 mL, 15 mmol, 1 M in DCM, 1.6 equiv) dropwise over 5 min. The reaction mixture was maintained at −78° C. for 1 h, then warmed to 0° C. for one hour. Upon completion of reaction as determined by TLC (ca. 2 h), the reaction was quenched by the addition of saturated aq NaHCO$_3$ (100 mL). The solution was extracted with DCM (3×50 mL) and the combined organic layers were washed with brine (50 mL), dried (MgSO$_4$), filtered and concentrated in vacuo. The crude mixture of regioisomers were dissolved in DMF (27 mL), followed by the addition of cesium carbonate (6.00 g, 18.3 mmol, 2 equiv), Bu$_4$NI (0.663 g, 1.84 mmol, 0.2 equiv) and 2-bromopropane (3.45 mL, 36.7 mmol, 4 equiv). The reaction mixture was maintained at room temperature for 18 h, before dilution with water (100 mL) and extraction with diethyl ether (3×50 mL). The combined extracts were washed with saturated aq NH$_4$Cl (75 mL) and brine (75 mL), dried (MgSO$_4$), filtered and concentrated in vacuo. The crude residue was purified by Teledyne ISCO column chromatography (column: 80 g, gradient, 0 to 10% EtOAc in hexanes) to afford 882 mg (30%) of 6 and 1.92 g (60%) of 5 as white amorphous solids.

6 $R_f$ 0.30 (4:1 hexanes/EtOAc); IR (thin-film): 2974, 1721, 1595, 1464, 1341 cm$^{-1}$; $^1$HNMR (400 MHZ, CDCl$_3$) δ 7.37 (s, 2H), 6.59 (d, J=9.0 Hz, 1H), 6.33 (d, J=9.0 Hz, 1H), 5.96-5.87 (m, 1H), 5.10 (dd, J=17 Hz, 1.8 Hz, 1H), 5.02 (dd, J=10 Hz, 1.8 Hz, 1H), 4.41 (m, 1H), 3.94 (s, 3H), 3.82 (s, 6H), 3.61 (d, J=6.0 Hz, 2H), 1.29 (d, J=6.0 Hz, 6H); $^{13}$C NMR (100 MHz, CDCl$_3$): 153.5, 150.8, 148.4, 138.6, 135.3, 132.1, 129.3, 123.4, 115.4, 112.0, 111.7, 104.1, 71.2, 65.4, 56.4, 31.9, 22.3; LRMS calculated for $C_{22}H_{26}ClO_6^+$ [M+H]$^+$ m/z 421.1, measured LC/MS (ESI) $R_f$ 0.871 min, m/z 421.6 [M+H]$^+$.

5 $R_f$: 0.42 (4:1 hexanes/EtOAc); IR (thin-film): 2965, 1719, 1597, 1477 cm$^{-1}$; $^1$H NMR (400 MHZ, CDCl$_3$) δ 7.35 (s, 2H), 6.90 (s, 1H), 6.32 (s, 1H), 5.83-5.73 (m, 1H), 4.92-4.87 (m, 2H), 4.43-4.40 (m, 1H), 3.92 (s, 3H), 3.81 (s, 6H), 3.18 (d, J=6.4 Hz, 2H), 1.30 (d, J=6.0 Hz, 6H); $^{13}$C NMR (100 MHZ, CDCl$_3$) δ 166.6, 153.0, 150.5, 147.3, 136.9, 136.5, 129.1, 127.0, 119.8, 116.2, 115.6, 115.5, 107.0, 71.3, 56.5, 52.3, 34.0, 22.1; LRMS calculated for $C_{22}H_{26}ClO_6^+$ [M+H]$^+$ m/z 421.1, measured LC/MS (ESI) $R_f$ 0.845 min, m/z 421.6 [M+H]$^+$.

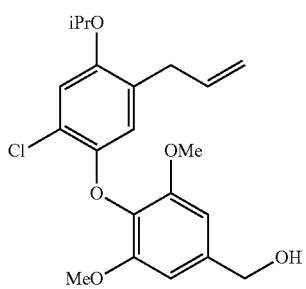

7

To a three-neck round bottom with a condenser, addition funnel and septum was added LAH (77 mg, 2.03 mmol, 1 equiv) in THF (8 mL). The suspension was heated to reflux for 15 minutes, then allowed to cool to room temperature before the dropwise addition of ester 5 (857 mg, 2.03 mmol, 1 equiv) as a solution in THF (8 mL, 0.25 M). The reaction mixture was maintained at room temperature for 1 h, before being cooled to 0° C. and diluted with Et$_2$O (8 mL). Water (77 μL), NaOH (15%, 77 μL) and then water (230 μL) were added in that order, slowly. The solution was allowed to warm to room temperature and stir for 15 minutes before the addition of MgSO$_4$ (ca. 250 mg). The mixture was stirred for 15 minutes, then filtered and concentrated in vacuo. The crude residue was purified by column chromatography (gradient, 0 to 30% EtOAc in hexanes) to afford 660 mg (83%) of 7 as a white solid: $R_f$: 0.15 (2:1 hexanes/EtOAc); IR (thin-film): 3398, 2967, 1599, 1480 cm$^{-1}$; $^1$H NMR (400 MHZ, CDCl$_3$) δ 6.90 (s, 1H), 6.63 (s, 2H), 6.33 (s, 1H), 5.83-5.76 (m, 1H), 4.92-4.87 (m, 2H), 4.64 (s, 2H), 4.39 (m, 1H), 3.74 (s, 6H), 3.17 (d, J=6.0 Hz, 2H), 1.29 (d, J=6.0 Hz, 6H); $^{13}$C NMR (100 MHz, CDCl$_3$): 153.2, 150.2, 147.7, 138.6, 136.7, 131.8, 129.1, 119.4, 116.0, 115.7, 115.3, 104.0, 71.4, 65.2, 56.3, 34.12; LRMS calculated for $C_{21}H_{26}ClO_5^+$ [M+H]$^+$ m/z 393.1, measured LC/MS (ESI) $R_f$ 0.550 min, m/z 393.4 [M+H]$^+$.

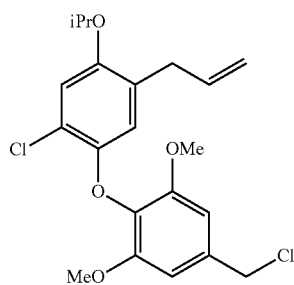

8

To a solution of alcohol 7 (1.7 g, 4.32 mmol) in CH$_3$CN (27 mL) was added iPr$_2$NEt (1.2 mL, 6.92 mmol, 1.6 equiv). The reaction mixture was cooled to 0° C. before the addition of triphenylphosphine dichloride (2.16 g, 6.49 mmol, 1.5 equiv). The mixture was maintained at 0° C. for 40 min or until judged complete by TLC (ca. 25 to 40 min). Upon completion the reaction mixture was loaded directly onto a silica gel packed column and purified (gradient, 0 to 10%, EtOAc in hexanes) to afford 1.7 g (96%) of 8 as a white solid: $R_f$: 0.71 (2:1 hexanes/EtOAc); IR (thin-film): 2968, 1598, 1482 cm$^{-1}$; $^1$H NMR (400 MHZ, CDCl$_3$) δ 6.91 (s, 1H), 6.68 (s, 2H), 6.35 (s, 1H), 5.89-5.78 (m, 1H), 4.94-4.89 (m, 2H), 4.59 (s, 2H), 4.42 (m, 1H), 3.78 (s, 6H), 3.19 (d, J=6.0 Hz), 1.31 (d, J=6.0 Hz, 6H); $^{13}$C NMR (100 MHZ, CDCl$_3$): 153.4, 150.5, 147.6, 136.8, 134.8, 132.9, 129.1, 119.7, 116.2, 115.7, 115.4, 106.1, 71.4, 56.5, 46.8, 34.2, 22.3; LRMS calculated for $C_{21}H_{25}Cl_2O_4^+$ [M+H]$^+$ m/z 411.1, measured LC/MS (ESI) $R_f$ 0.871 min, m/z 411.4 [M+H]$^+$.

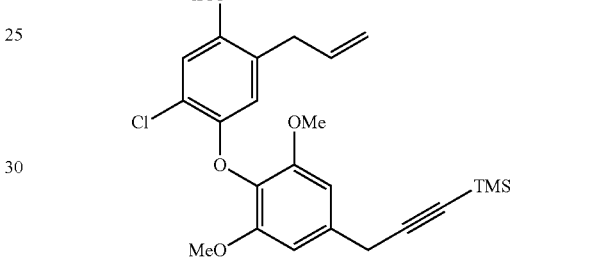

9

To a 0° C. solution of freshly distilled TMS-acetylene (3.50 mL, 25.4 mmol, 5 equiv) in THF (31.0 mL) was added EtMgBr (11.2 mL, 20.2 mmol, 1.80 M in THF, 4 equiv) dropwise. The solution was allowed to warm to room temperature and maintained for 1 h. Then Cu(I)Br (0.868 g, 6.07 mmol, 1.2 equiv) was added. The resulting suspension was maintained at room temperature for 1 h, before the addition of chloride 8 (2.08 g, 5.06 mmol) in THF (20 mL). The reaction mixture was heated and maintained at 65° C. for 24 h. The reaction mixture was allowed to cool to room temperature, before the addition of saturated aq NH$_4$Cl (20 mL) and extraction with Et$_2$O (3×30 mL). The combined organic extracts were washed with saturated aq NH$_4$Cl (2×40 mL) and brine (45 mL). The washed extracts were dried (MgSO$_4$), filtered and concentrated in vacuo. The residue was purified by flash column chromatography (gradient, 0 to 2%, EtOAc in hexanes) to afford 1.89 g (80%) of 9 as a white solid: $R_f$: 0.42 (9:1 hexanes/EtOAc); IR (thin-film): 2967, 2176, 1598, 1488 cm$^{-1}$; $^1$H NMR (400 MHZ, CDCl$_3$) δ 6.91 (s, 1H), 6.67 (s, 2H), 6.36 (s, 1H), 5.86-5.79 (m, 1H), 4.94-4.89 (m, 1H), 4.41 (m, 1H), 3.78 (s, 6H), 3.67 (s, 2H), 3.2 (d, J=6 Hz, 2H), 1.30 (d, J=6.0 Hz, 6H), 0.23 (s, 9H); $^{13}$C NMR (100 MHz, CDCl$_3$) δ 153.1, 150.2, 147.8, 136.7, 133.7, 133.1.2, 128.9, 119.5, 116.0, 115.6, 115.3, 105.2, 104.1, 87.7, 71.3, 56.2, 34.1, 26.4, 22.2, 0.11; LRMS calculated for $C_{26}H_{34}ClO_4Si^+$ [M+H]$^+$ m/z 473.1, measured LC/MS (ESI) $R_f$ 1.21 min, m/z 473.6 [M+H]$^+$.

10

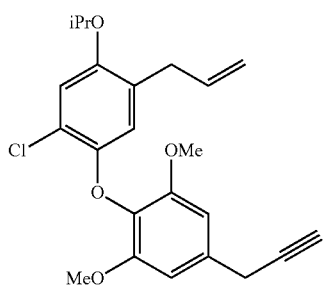

To a solution of alkyne 9 (435 mg, 0.919 mmol) in MeOH (9 mL) and THF (0.919 mL) was added NaOMe (90 μL, 0.138 mmol, 1.52 M in MeOH, 0.15 equiv) dropwise. The solution was maintained at room temperature for 4 h before being concentrated in vacuo. The crude residue was purified by flash column chromatography (gradient, 0 to 3%, EtOAc in hexanes) to afford 350 mg (95%) of 10 as a white solid: $R_f$: 0.41 (9:1 hexanes/EtOAc); IR (thin-film) 3292, 2973, 2251, 2118, 1597 cm$^{-1}$; $^1$H NMR (400 MHZ, CDCl$_3$) δ 6.91 (s, 1H) 6.65 (s, 2H), 6.35 (s, 1H), 6.87-5.77 (m, 1H), 4.91 (m, 2H), 4.41 (m, 1H), 3.78 (s, 6H), 3.62 (d, J=2.6 Hz, 2H), 3.19 (d, J=6 Hz, 2H), 2.25 (t, J=2.6 Hz, 1H), 1.31 (d, J=6.0 Hz, 6H), 0.23 (s, 9H); $^{13}$C NMR (100 MHz, CDCl$_3$) δ 153.3, 150.3, 147.8, 136.8, 133.5, 131.5, 129.1, 119.5, 116.1, 115.7, 115.3, 105.4, 81.8, 71.4, 71.0, 56.4, 34.2, 25.2, 22.3; LRMS calculated for $C_{23}H_{26}ClO_4^+$ [M+H]$^+$ m/z 401.1, measured LC/MS (ESI) $R_f$ 0.880 min, m/z 401.6 [M+H]$^+$.

11

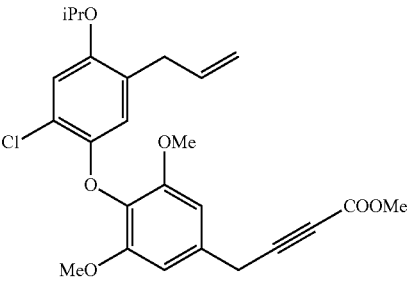

To a −78° C. solution of 10 (0.669 g, 1.66 mmol) in THF (20 m) was added n-BuLi (0.842 mL, 1.68 mmol, 1.05 equiv) dropwise over 5 min. The reaction mixture was maintained at −78° C. for 5 min, then CO$_2$ (g) was bubbled through the mixture for 10 min. The reaction was allowed to slowly warm to room temperature over 2 h, while under an atmosphere of CO$_2$ (g). Upon completion as judged by LCMS (ca. 2.5 h), the reaction was quenched with 1 N HCl (15 mL) and extracted with Et$_{20}$ (3×20 mL), the organic extracts were combined, washed with brine (25 mL), dried (MgSO$_4$), and concentrated in vacuo. The crude oil as purified by column chromatography (gradient, 0 to 20% MeOH in DCM) to afford 0.590 g (80%) of 11 as a yellow foam: $R_f$ 0.48 (4:1 DCM/MeOH); IR (thin-film): 3424, 2970, 2237, 1687, 1613, 1482 cm$^{-1}$; $^1$H NMR (400 MHZ, CDCl$_3$) δ 9.61 (bs, 1H), 6.90 (s, 1H), 6.59 (s, 2H), 6.33 (s, 1H), 5.84-5.78 (m, 1H), 4.94-4.89 (m, 2H), 4.41 (m, 1H), 3.77 (s, 8H), 3.29 (d, J=6.4 Hz, 2H), 1.30 (d, J=6.0 Hz, 6H); $^{13}$C NMR (100 MHz, CDCl$_3$): 157.6, 153.5, 150.4, 147.7, 136.7, 132.0, 131.1, 129.2, 119.6, 116.1, 115.8, 115.4, 105.6, 89.1, 71.5, 56.5, 34.2, 25.5, 22.3; LRMS calculated for $C_{23}H_{26}ClO_4^+$ [M+H]$^+$ m/z 445.1, measured LC/MS (ESI) $R_f$ 0.705 min, m/z 445.6 [M+H]$^+$.

12

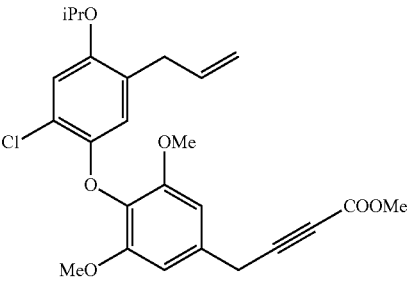

To a solution of acid 11 (0.550 mg, 1.24 mmol, 1 equiv) in MeOH (3.00 mL) was added SOCl$_2$ (50.0 μL, 0.620 mmol, 0.5 equiv). The reaction mixture was maintained at room temperature, until judged complete by TLC (ca. 5 h), before concentration in vacuo. The crude residue was purified by column chromatography (gradient, 0 to 20%, EtOAc in hexanes) to afford 0.460 g (80%) of 12 as a yellow foam: $R_f$ 0.27 (4:1 hexanes/EtOAc); IR (thin-film): 2963, 2240, 1714, 1598, 1482 cm$^{-1}$; $^1$H NMR (400 MHZ, CDCl$_3$) δ 6.90 (s, 1H), 6.59 (s, 2H), 6.32 (s, 1H), 5.86-5.76 (m, 1H), 4.92 (m, 2H), 4.41 (m, 1H), 3.80 (s, 3H), 3.77 (s, 6H), 3.75 (s, 2H), 3.19 (d, J=6.8 Hz, 2H), 1.30 (d, J=6.0 Hz, 6H); $^{13}$C NMR (100 MHz, CDCl$_3$): 154.2, 153.5, 150.4, 147.7, 136.8, 132.0, 131.4, 129.1, 119.6, 116.1, 115.7, 115.4, 105.6, 86.5, 74.9, 71.4, 56.5, 52.8, 34.2, 25.4, 22.3; LRMS calculated for $C_{25}H_{28}ClO_6^+$ [M+H]$^+$ m/z 459.1, measured LC/MS (ESI) $R_f$ 0.870 min, m/z 459.6 [M+H]$^+$.

13

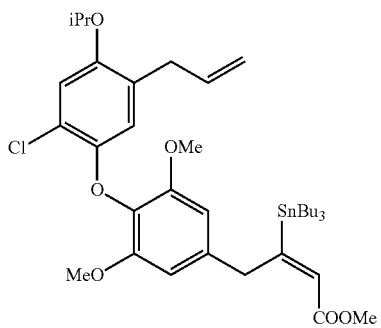

To a suspension of Cu(I)CN (0.112 g, 1.26 mmol, 1.2 equiv) in THF (5.0 mL) at −78° C. was added n-BuLi (1.26 mL, 2.53 mmol, 2.4 equiv, 2 M in hexanes) dropwise. The suspension was warmed to −40° C. for ten minutes and then cooled to −78° C., this warming and cooling process was repeated until the reaction solution is homogenous (ca. 3 cycles). Once homogenous, Bu$_3$SnH (0.680 mL, 2.53 mmol, 2.4 equiv) was added dropwise over 5 min and the reaction was stirred at −78° C. for 25 minutes (bright yellow solution). Once the solution is bright yellow, 12 (0.485 g, 1.05 mmol) was added as a solution in MeOH (4.6 mL, 2.74 mmol, 2.6 equiv, 0.65 M in THF) over ten minutes. The reaction mixture was maintained at −78° C. until judged complete by TLC (ca. 2 h), and quenched at −78° C. with saturated aq NH$_4$Cl (6 mL). The reaction mixture was allowed to slowly warm to room temperature and maintained until the aqueous layer is deep blue in color. The reaction was extracted with Et$_2$O (3×15 mL) and the organic extracts were combined and washed with saturated aq NH$_4$Cl (2×20 mL) and brine (20 mL). The washed extracts were dried (MgSO$_4$), filtered and concentrated in vacuo. The crude residue was purified by flash column chromatography (10:1 Silica gel/K$_2$CO$_3$ packing material: gradient, 0 to 3% EtOAc in hexanes) to afford 0.480 g (61%) of 13 as a clear oil: R$_f$: 0.41 (4:1 hexanes/EtOAc); IR (thin-film): 2926, 1711, 1593, 1490 cm$^{-1}$; $^1$H NMR (400 MHZ, CDCl$_3$) δ 6.90 (s, 1H), 6.46 (s, 2H), 6.34 (s, 1H), 6.12 (s, 1H), 5.84-5.76 (m, 1H), 4.90 (m, 2H), 4.41 (m, 1H), 4.27 (s, 2H), 3.76 (s, 3H), 3.74 (s, 6H), 3.17 (d, J=6.4 Hz, 2H), 1.40-1.30 (m, 6H), 1.30 (d, J=6.0 Hz, 6H), 1.28-1.22 (m, 7H), 0.86 (t, J=7.4 Hz, 9H), 0.80-0.77 (m, 5H); $^{13}$C NMR (100 MHZ, CDCl$_3$) δ 170.9, 165.0, 153.2, 150.2, 147.9, 136.9, 136.8, 131.4, 129.0, 128.1, 119.5, 116.1, 115.7, 115.2, 106.7, 71.3, 56.3, 51.1, 41.3, 34.3, 29.0, 27.4, 22.3, 13.7, 10.4; LRMS calculated for C$_{37}$H$_{56}$ClO$_6$Sn$^+$ [M+H]$^+$ m/z 751.2, measured LC/MS (ESI) R$_f$ 1.40 min, m/z 751.2 [M+H]$^+$.

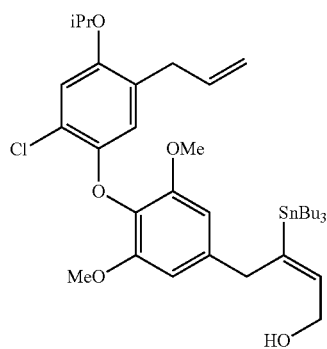

14

To a −78° C. solution of 13 (0.267 mg, 0.331 mmol) in DCM (7 mL) was added DIABL (0.828 mL, 0.828 mmol, 2.5 equiv, 1 M in hexanes), the solution was maintained at −78° C. for 1 h, then DIBAL (0.331 mL, 0.331 mmol, 1 equiv, 1 M in hexanes) was added. The solution was warmed and maintained at −15° C. for 20 minutes, before addition of saturated aq Rochelle's salt (10 mL). The biphasic solution was maintained at room temperature overnight with vigorous stirring. The layers were separated and the aqueous layer was extracted with DCM (3×15 mL). The combined organic was washed with brine (30 mL), dried (Na$_2$SO$_4$), filtered and concentrated in vacuo. The crude residue was purified by column chromatography (gradient, EtOAc in hexanes:

0-30%) to afford 191 mg (80%) of 14 as a yellow oil: R$_f$: 0.2 (4:1 hexanes/EtOAc); IR (thin-film): 3376, 2930, 1592, 1481 cm$^{-1}$; $^1$H NMR (400 MHZ, CDCl$_3$) δ 6.89 (s, 1H), 6.42 (s, 2H), 6.34 (s, 1H), 5.96 (t, J=6.1 Hz, 1H), 5.84-5.77 (m, 1H), 4.90 (m, 2H), 4.41 (m, 3H), 3.75 (s, 3H), 3.65 (s, 2H), 3.18 (d, J=6 Hz, 2H), 1.43-1.23 (m, 19H), 0.88-0.77 (m, 14H); $^{13}$C NMR (100 MHz, CDCl$_3$) δ 153.2, 150.3, 147.9, 146.3, 137.8, 136.8, 131.3, 129.1, 119.6, 116.2, 115.8, 115.3, 106.3, 71.4, 59.3, 56.4, 39.7, 34.4, 29.2, 27.5, 22.3, 13.8, 10.0; LRMS calculated for C$_{26}$H$_{56}$ClO$_5$Sn$^+$ [M+H]$^+$ m/z 723.2, measured LC/MS (ESI) R$_f$ 1.43 min, m/z 705.6 [M−H$_2$O]$^+$.

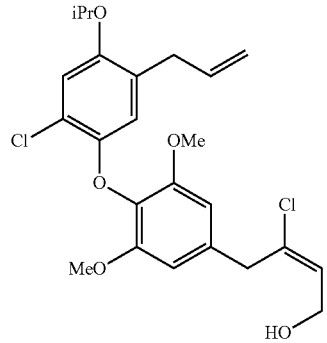

15

To a 0° C. solution of 14 (317 mg, 0.439 mmol, 1 equiv) in THF (9.0 mL) was added CuCl$_2$ (1.18 g, 8.78 mmol, 20 equiv). The reaction mixture was allowed to slowly warm to room temperature and maintained until completion, as judged by TLC (ca. 18 h). The reaction was quenched by the addition of saturated aq NH$_4$Cl (20 mL). The solution was extracted with diethyl ether (3×30 mL), washed with saturated aq NH$_4$Cl (2×30 mL) and brine (40 mL), dried (Na$_2$SO$_4$), filtered and concentrated in vacuo. The crude residue was purified by flash column chromatography (gradient, 0 to 30% EtOAc in hexanes) to afford 154 mg (75%) of 15 as a clear oil: R$_f$ 0.2 (3:1 hexanes/EtOAc,); IR (thin-film): 3404, 2972, 1597, 1488 cm$^{-1}$; $^1$H NMR (400 MHZ, CDCl$_3$) § 6.90 (s, 1H), 6.53 (s, 2H), 6.34 (s, 1H), 6.05 (t, J=7.3 Hz, 1H), 5.81-5.77 (m, 1H), 4.93-4.89 (m, 2H), 4.41 (m, 1H), 4.30 (d, J=7.3 Hz, 2H), 3.76 (s, 6H), 3.73 (s, 2H), 3.19 (d J=6.4 Hz, 2H), 1.30 (d, J=6.0 Hz, 6H); $^{13}$C NMR (100 MHz, CDCl$_3$) δ 153.3, 150.3, 147.8, 136.78, 136.70, 134.2, 131.9, 129.1, 128.0, 119.6, 116.2, 115.8, 115.4, 106.2, 71.44, 59.1, 56.5, 40.6, 34.2, 22.3; LRMS calculated for C$_{24}$H$_{29}$Cl$_2$O$_5$$^+$ [M+H]$^+$ m/z 467.1, measured LC/MS (ESI) R$_f$ 0.752 min, m/z 449.6 [M−H$_2$O]$^+$.

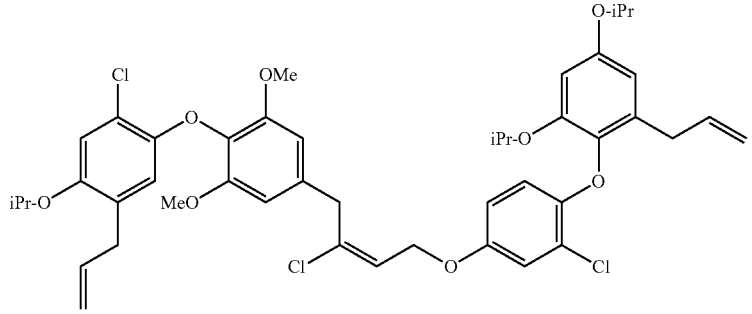

17

To a 0° C. solution of alcohol 15 (175 mg, 0.374 mmol), phenol 4 (211 mg, 0.561 mmol, 1.50 equiv) and Ph$_3$P (147 mg, 0.561 mmol, 1.50 equiv) in DCM (2.00 mL) was added a solution of diethyl azodicarboxylate (0.478 mL, 1.05 mmol, 40 wt. % in toluene, 1.50 equiv) at a rate of ca. 1 drop every 2 min. Following the addition, the reaction mixture was maintained at 0° C. for 30 min, then was allowed to warm to room temperature and maintained until judged complete by TLC (ca. 15-30 min). The reaction mixture was loaded directly onto a silica gel column and purified (silica gel, gradient elution, 0-10% EtOAc in hexanes) to afford 233 mg (75%) of ether 17 as a white foam: $R_f$ 0.56 (3:1 hexanes/EtOAc); IR (thin-film): 3068, 2971, 1595, 1478 cm$^{-1}$; $^1$H NMR (400 MHZ, CDCl$_3$) δ 7.01 (d, J=2.9 Hz, 1H), 6.91 (s, 1H), 6.62 (dd, J=9.0, 2.9 Hz, 1H), 6.54 (s, 2H), 6.48 (d, J=9.0 Hz, 1H), 6.42 (m, 2H), 6.36 (s, 1H), 6.12 (t, J=7.0 Hz, 1H), 5.91-5.77 (m, 2H), 5.07-5.00 (m, 2H), 4.93-4.89 (m, 2H), 4.58 (d, J=7.0 Hz, 2H), 4.54-4.47 (m, 1H), 4.44-4.38 (m, 2H), 3.77 (s, 2H), 3.74 (s, 6H), 3.30 (d, J=6.7 Hz, 2H), 3.20 (d, J=6.4 Hz, 2H), 1.34 (d, J=6.0 Hz, 6H), 1.31 (d, J=6.0 Hz, 6H) 1.14 (d, J=6.0 Hz, 6H); $^{13}$C NMR (100 MHZ, CDCl$_3$) δ 155.4, 153.3, 152.6, 151.0, 150.2, 149.2, 147.7, 138.4, 136.8, 136.6, 136.2, 134.9, 133.8, 131.8, 129.0, 124.1, 122.5, 119.5, 116.4, 116.3, 116.1, 115.7, 115.6, 115.4, 113.7, 108.5, 106.2, 103.6, 71.6, 71.3, 70.3, 64.7, 56.4, 40.8, 34.4, 34.1, 22.2, 22.1, 22.0; LRMS calculated for C$_{45}$H$_{51}$Cl$_3$O$_8{}^+$ [M+H]$^+$ m/z 825.2, measured LC/MS (ESI) $R_f$ 1.22 min, m/z 825.6 [M+H]$^+$.

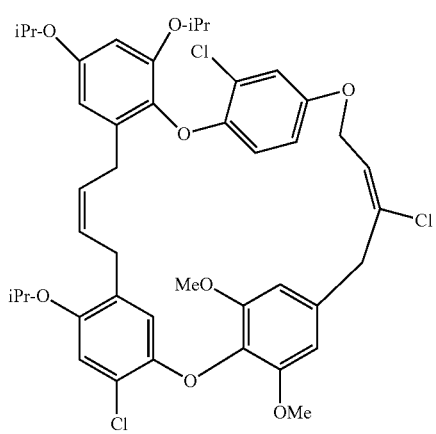

18

To a degassed solution of diene 17 (55.0 mg, 0.066 mmol) in DCE (21.0 mL) was added a solution of Grubbs C633 catalyst (ca. 9 mg, 0.014 mmol, 16.0 mol %) in DCE (1.00 mL). The solution was frozen and placed under vacuum (ca. 0.01 torr) for ca. 10 min, the reaction vessel was sealed under vacuum and allowed to slowly warm to room temperature. Once the flask was at room temperature, the reaction was heated and maintained at 60° C. for 24 h. The reaction was allowed to cool to room temperature and quenched by the addition of ethyl vinyl ether (100 μL). The solution was concentrated in vacuo and purified by flash column chromatography (silica gel, gradient elution, 0-10% EtOAc in hexanes) to afford 39.0 mg (74%) of macrocycle 18 as a white foam: $R_f$ 0.48 (3:1 hexanes/EtOAc); IR (thin-film): 2975, 2930, 1594, 1483, 1382 cm$^{-1}$; $^1$H NMR (400 MHZ, CDCl$_3$) δ 6.96 (d, J=2.8 Hz, 1H), 6.87 (s, 1H), 6.59 (dd, J=9.0, 2.9 Hz, 1H), 6.38 (m, 2H), 6.36 (s, 2H), 6.32 (d, J=2.7 Hz, 2H), 6.14 (s, 1H), 6.10 (t, J=6.7 Hz, 1H), 5.55-5.51 (m, 1H), 5.40-5.33 (m, 1H), 4.56 (d, J=6.8 Hz, 2H), 4.45-4.38 (m, 3H), 3.77 (s, 2H), 3.67 (s, 6H), 3.26 (d, J=7.2 Hz, 2H), 3.08 (d, J=7.2 Hz, 2H), 1.34 (d, J=6.0 Hz, 6H), 1.31 (d, J=6.0 Hz, 6H), 1.14 (d, J=6.0 Hz, 6H); $^{13}$C NMR (100 MHz, CDCl$_3$) δ 155.6, 153.4, 152.5, 151.0, 150.3, 149.5, 147.5, 137.0, 136.3, 135.5, 133.6, 131.5, 129.7, 129.1, 127.5, 125.8, 122.5, 119.2, 118.2, 115.6, 115.37, 115.31, 114.2, 108.5, 105.7, 104.0, 71.9, 71.1, 70.4, 66.0, 56.4, 40.8, 28.9, 27.5, 22.3, 22.2, 22.1; LRMS calculated for C$_{43}$H$_{47}$Cl$_3$O$_8{}^+$ [M+H]$^+$ m/z 797.2, measured LC/MS (ESI) $R_f$ 1.10 min, m/z 797.6 [M+H]$^+$.

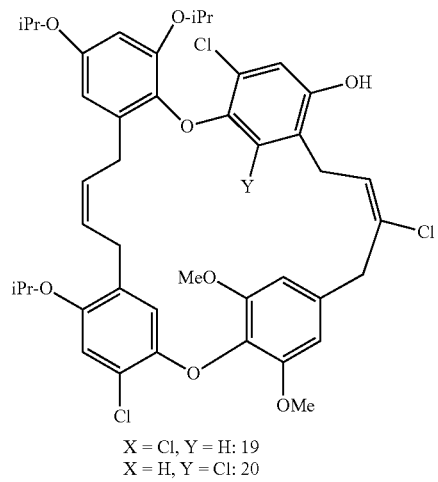

X = Cl, Y = H: 19
X = H, Y = Cl: 20

To a solution of ether 18 (67.0 mg, 0.084 mmol) in DCE (16.0 mL) was added BF$_3$·Et$_2$O (502 μL, 0.251 mmol, 0.5 M in DCE, 3.00 equiv) dropwise. The reaction was heated and maintained at 70° C. for 2 h. The reaction was allowed to cool to room temperature and quenched by the addition of brine (10 mL). The reaction mixture was extracted with EtOAc (3×10 mL), and the combined organic extracts washed with brine (15 mL). The washed organic extracts were dried (MgSO$_4$), filtered and concentrated in vacuo to afford the ~27.0 mg (40%) of an inseparable mixture of phenols 19 and 20, which were used, as is, in the subsequent step: $R_f$ 0.41 (3:1 hexanes/EtOAc); LRMS calculated for C$_{43}$H$_{47}$Cl$_3$O$_8{}^+$ [M+H]$^+$ m/z 797.2, measured LC/MS (ESI) $R_f$ 1.00 min, m/z 796.2 [M+H]$^+$.

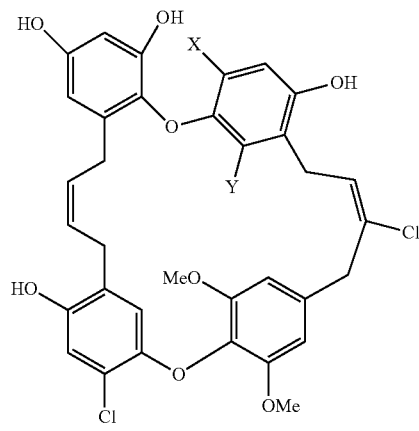

X = Cl, Y = H: VU0848355
X = H, Y = Cl: VU0848354

To a −78° C. solution of phenols 19 and 20 (24.0 mg, 0.030 mmol) in DCM (1.00 mL) was added a solution of BCl$_3$ (120 μL, 0.120 mmol, 1 M in DCM, 4.00 equiv) dropwise. The reaction mixture was allowed to warm to room temperature slowly over 1 h and maintained at room temperature until judged complete by TLC (ca. 2-4 h). The reaction was diluted with brine (2 mL) and extracted with EtOAc (4×10 mL). The combined organic extracts were washed with brine (5 mL), dried (Na$_2$SO$_4$), filtered and concentrated in vacuo. The crude residue (~17 mg) was purified by Gilson preparative HPLC (13-80% CH$_3$CN in H$_2$O, over 6 min) to afford 7.00 mg (35%) of VU0848355 and 8 mg (40%) of VU0848354.

VU0848355: R$_f$ 0.31 (10% methanol/DCM); $^1$H NMR (400 MHZ, CD$_3$OD) δ 6.86 (s, 1H), 6.76 (s, 1H), 6.35 (s, 1H), 6.25 (d, J=2.8 Hz, 1H), 6.18 (t, J=8.6 Hz, 1H), 6.10 (d, J=2.8 Hz, 1H), 6.08 (s, 1H), 5.56-5.55 (m, 2H), 3.62 (s, 2H), 3.53-3.50 (m, 8H), 3.19 (d, J=6.8 Hz, 2H) 2.91 (apt d, J=4.4 Hz, 2H); $^{13}$C NMR (150 MHz, CD$_3$OD) 156.1, 154.3, 151.4, 150.7, 150.2, 148.7, 148.6, 136.7, 136.4, 135.8, 134.6, 132.3, 129.9, 128.39, 128.34, 127.8, 127.4, 120.6, 119.1, 117.4, 116.9, 116.2, 116.0, 107.7, 103.2, 56.4, 56.2, 40.8, 29.9, 28.7, 27.5; LRMS calculated for C$_{34}$H$_{29}$Cl$_3$O$_8$$^+$ [M+H]$^+$ m/z 671.1, measured LC/MS (ESI) R$_f$ 1.16 min, m/z 671.4 [M+H]$^+$.

VU0848354: R$_f$ 0.24 (10% methanol/DCM); $^1$H NMR (600 MHZ, CD$_3$OD) δ 6.78 (s, 1H), 6.56 (d, J=9.0 Hz, 1H), 6.37 (m, 3H), 6.26-6.25 (m, 2H), 6.23 (s, 1H), 6.13 (d, J=3.0 Hz, 1H), 5.73-5.70 (m, 1H), 5.47-5.43 (m, 1H), 3.86 (s, 2H), 3.70 (d, J=7.8 Hz, 2H), 3.56 (s, 6H), 3.25 (d, J=7.8 Hz, 2H), 2.86 (d, J=7.2 Hz, 2H); $^{13}$C NMR (150 MHz,) δ 154.9, 152.8, 150.4, 150.2, 148.9, 147.2, 146.9, 135.4, 135.1, 133.2, 132.6, 130.3, 129.5, 127.3, 126.0, 125.4, 121.4, 118.0, 115.3, 114.2, 112.5, 111.3, 106.9, 105.3, 101.5, 55.1, 41.0, 27.9, 26.7, 26.0; LRMS calculated for C$_{34}$H$_{29}$Cl$_3$O$_8$$^+$ [M+H]$^+$ m/z 671.1, measured LC/MS (ESI) R$_f$ 1.23 min, m/z 671.4 [M+H]$^+$.

Example 3 Antimicrobial Susceptibility Studies

The bacterial growth inhibition of synthetic 9-dechlorochrysophaentins compared favorably to chrysophaentin A when evaluated across a panel of Gram-positive pathogens (Table 1). While the MICs of 9-dechlorochrysophaentin A (VU0849855) against S. aureus, MRSA and E. faecalis was similar to natural chrysophaentin A, iso-9-dechlorochrysophaentin (VU0849838) showed approximately two-fold superior growth inhibition against these pathogens.

TABLE 1

Antimicrobial activities of chrysophaentins MIC$_{50}$ (μg/mL)

|  | S. Aureus | MRSA | E. Faecalis | VRE | B. Subtifis |
|---|---|---|---|---|---|
| chrysophaentin A | 2 | 2 | 2 | 2 | n/a |
| VU0849855 | 2.5 | 2.5 | 2.5 | 5 | 4 |
| VU0849838 | 1.1 | 1.1 | 0.3 | 2.2 | 2 |

Chrysophaentin A has been proposed to act as an inhibitor of the cytoskeletal protein FtsZ. FtsZ is a GTPase dependent protein shown to play a critical role in bacterial cell division. Fluorescently labeled FtsZ has been shown to localize to the midline of the cell during the course of cell division to form a contractile structure referred to as the Z-ring, by way of a dynamic GTP-dependent polymerization. As a central player in cell division, the inhibition of FtsZ function has been considered as an untapped approach to the development of novel antimicrobial agents. Chrysophaentin A was shown to inhibit FtsZ mediated polymerization and was shown to bind recombinant FtsZ at the GTP binding site by Saturation Transfer Difference (STD) NMR.

Only recently has the central role of FtsZ and other proteins in the orchestration of cell division been fully appreciated. High-resolution microscopy enabled single-molecule tracking and real-time, temporal mapping of cell wall synthesis and revealed FtsZ's dynamic role in guiding the multi-protein complex called the divisome. It has been long known that FtsZ polymerizes at the bacterial plane of cell division leading to the so-called Z-ring structure, which has readily been visualized by microscopy using fluorescently labeled FtsZ protein. Super-resolution techniques have revealed FtsZ filaments display a rotational, inward movement coinciding with peptidoglycan synthesis. In this process FtsZ motion is powered by its own GTPase activity, anchored by FtsA and in concert with PBP orchestrates cell wall biosynthesis. The entire dynamic process, termed "tread-milling", can be visualized in real-time using high-resolution microscopy and orthogonally labeled proteins and fluorescent D-amino acids (FDAAs).

Figure 3A:
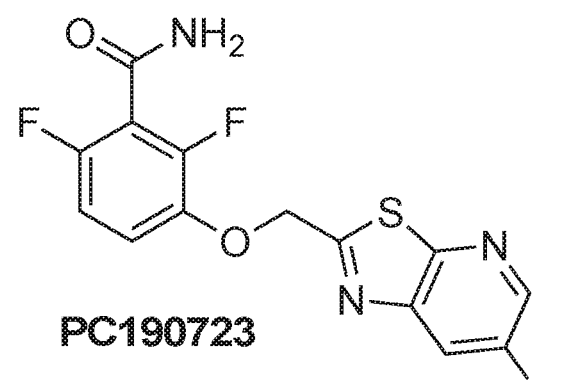
FIGS. 3A and 3B show *subtilis* phenotype in response to antimicrobials.
Figure 3B:
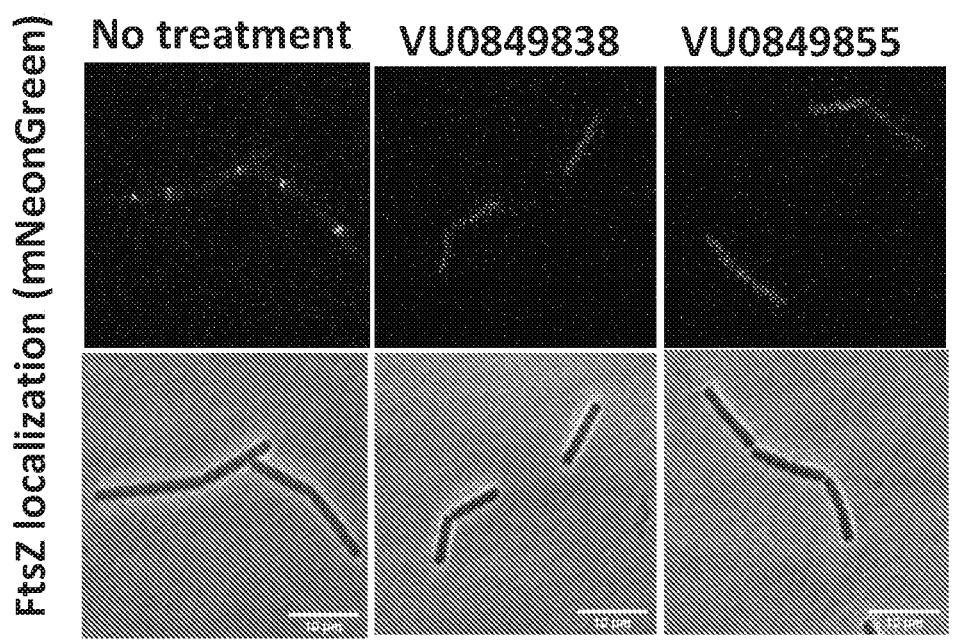
Figure 4A:
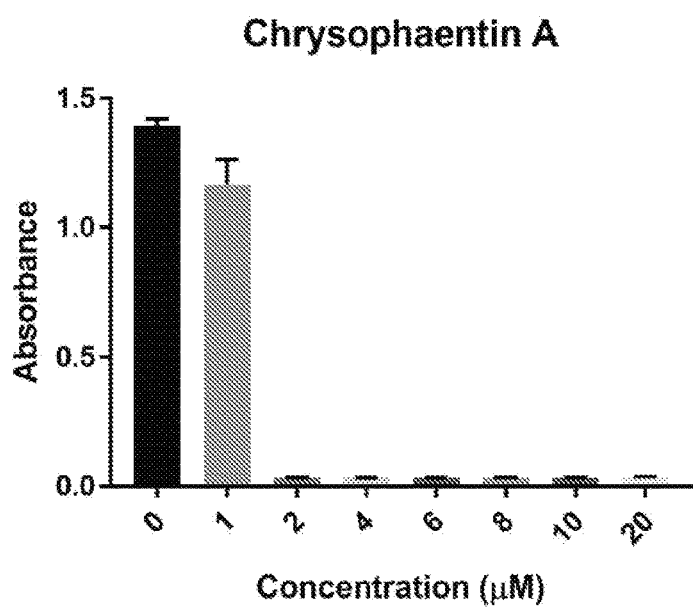
FIGS. 4A and 4B show the antimicrobial and induced phenotype of chrysophaentin A.
Figure 4B:
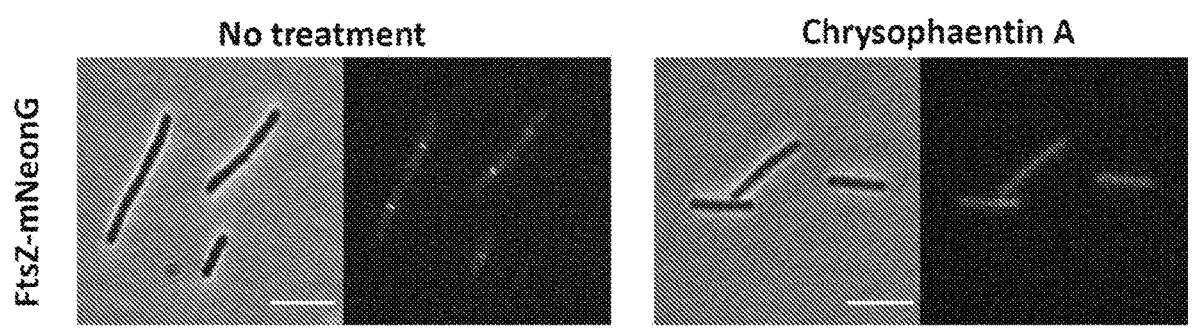

The compounds disclosed herein, 9-dechlorochrysophaentins VU0849855 and VU0849838, were compared to the well-studied FtsZ inhibitor PC1907723 (FIG. 3A). Inhibition of FtsZ by PC1907723 is known to produce an elongated phenotype of rod like bacteria such as B. Subtilis. Cell lengthening was observed when B. Subtilis was treated with PC190723 at a concentration of 5 μg/mL (10×MIC). In contrast, concentrations of VU0849855 and VU0849838 up to 20 μM (10×MIC) did not affect cell lengthening. Next, the affect of PC190723 and 9-dechlorochrysophaentins on cell wall biosynthesis was examined using fluorescent D-amino acids (FDAAs). Surprisingly, VU0849855 and VU0849838 inhibited incorporation of FDAAs at 10 μM (5×MIC), comparable to the well-known peptidoglycan inhibitor ampicillin (10×MIC). In contrast, the FtsZ inhibitor PC190723 showed minimal inhibition of FDAAs incorporation up to 10×MIC as reported earlier. The effect of 9-dechlorochrysophaentins on localization of FtsZ was then examined using fluorescently labeled FtsZ (mNeonG). Using concentrations of 10 μM (5×MIC) VU0849855 and VU0849838 lead to complete disassociation of FtsZ as observed by high-resolution microscopy (FIG. 3B). In contrast, PC190723 leads to dislocation but retention of FtsZ as reported earlier, and in agreement with continued cell wall synthesis as observed using FDAA. Furthermore, natural chrysophaentin A replicated the FtsZ dispersion phenotype in B. Subtilis (FIGS. 4A and 4B).

Figure 5A:
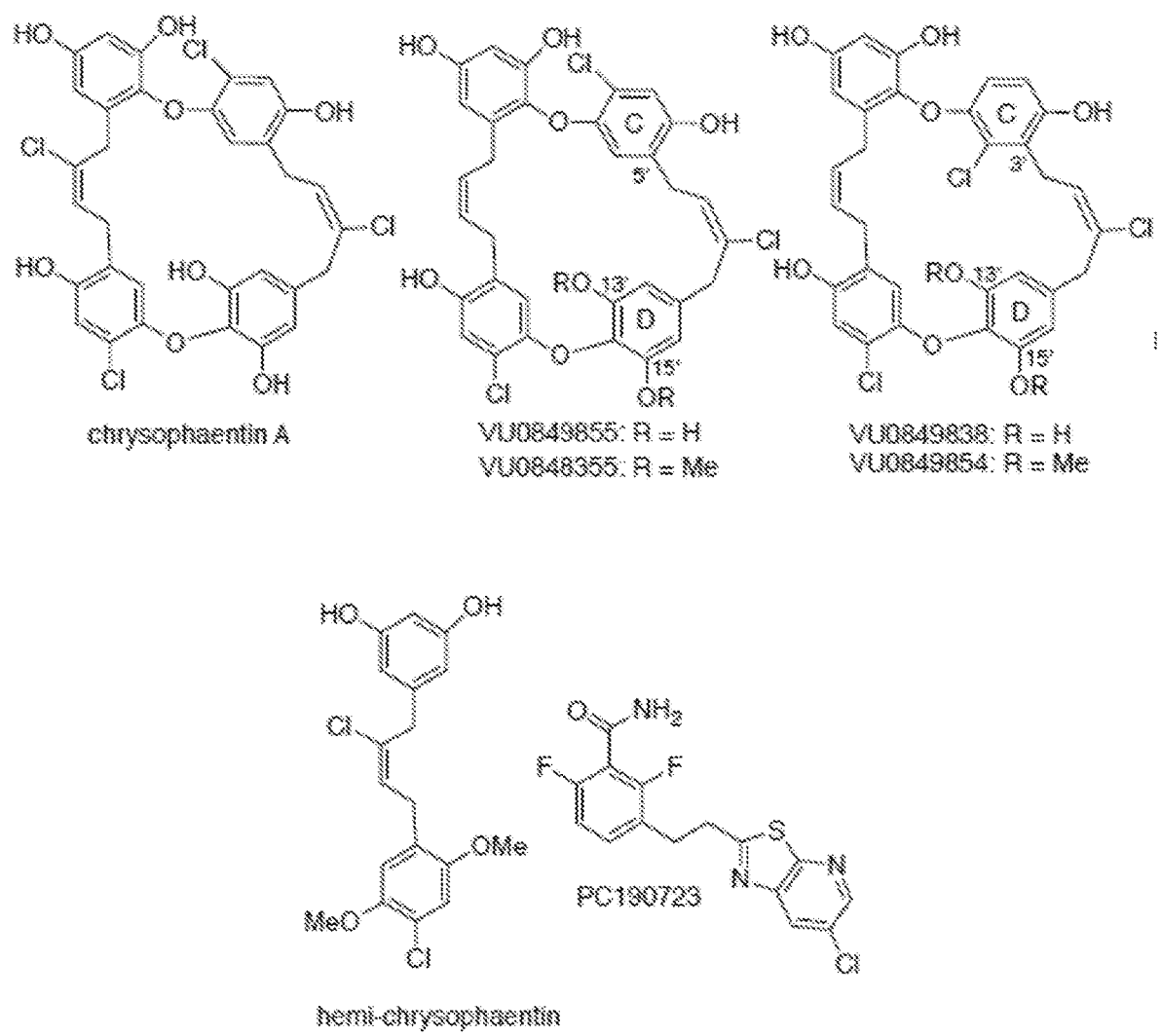

Comparison of the activities of chrysophaentin A and various compounds are shown in FIGS. 5A-5C. Remarkably, these results show that the synthetic analog compounds disclosed herein have antimicrobial activities that are comparable to or higher than the natural product chrysophaentin A. Even more remarkably, the unnatural C-ring isomers VU0849838 and VU0848354 are approximately two-fold more potent than the natural C-ring isomers VU0849855 and VU0848355 in inhibiting bacterial growth.

Example 4 Studies of VU0848355 and VU0848354

VU0848355 and VU0848354 were evaluated for growth inhibition against S. aureus and inhibition of GTPase activity against S. aureus FtsZ using a biochemical assay (FIGS.

Figure 6A:
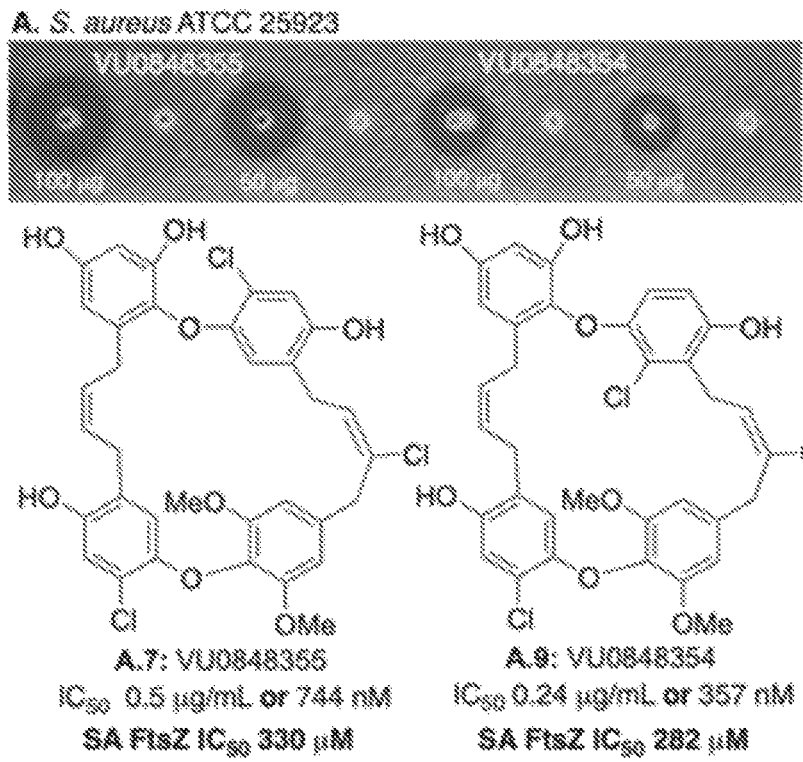
FIGS. 6A-6C show the activity data for VU0848355 and VU0848354.
Figure 6B:
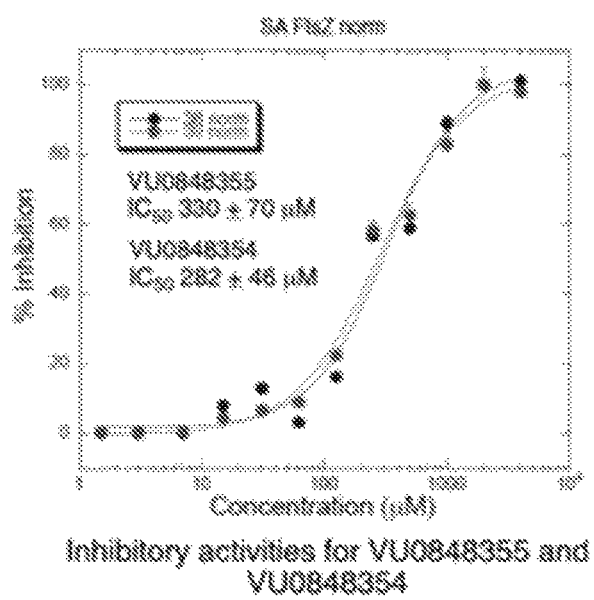
Figure 6C:
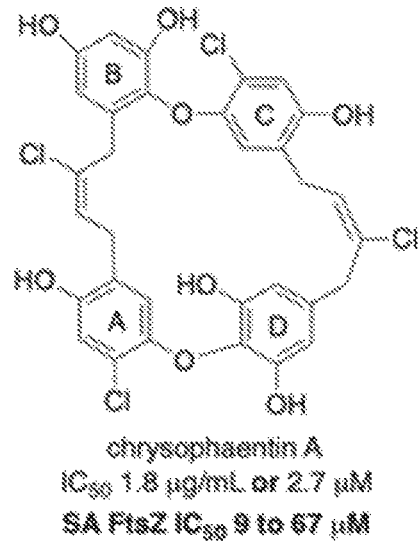

6A-6C). These chrysophaentin analogs inhibited growth of *S. aureus* ATCC 25293 (FIG. 6A, agar diffusion and microbroth dilution ($IC_{50}$<1 µM) assays) comparable or superior to chrysophaentin A itself. Surprisingly, these compounds showed low potency in the FtsZ biochemical assay ($IC_{50}$>250 µM) (FIG. 6B). For comparison, the same data is provided for chrysophaentin A (FIG. 6C), which demonstrated similar growth inhibition activity against *S. aureus* but significantly higher potency in GTPase-FtsZ inhibition (9 to 67 µM compared to >250 µM for VU0848355 and VU0848354). Overall, these results indicated activity in the GTPase-FtsZ assay and observed growth inhibition do not correlate and suggested that inhibition of FtsZ by the chrysophaentins may be more complicated.

Application of fluorescently labeled proteins and fluorescent D-amino acids (FDAAs) may be used to study bacterial cell division by monitoring peptidoglycan synthesis. Previous studies found a complex machinery formed by FtsZ, FtsA and peptidoglycan synthases orchestrate cell wall biosynthesis by way of a "treadmilling process."

Figure 7A:
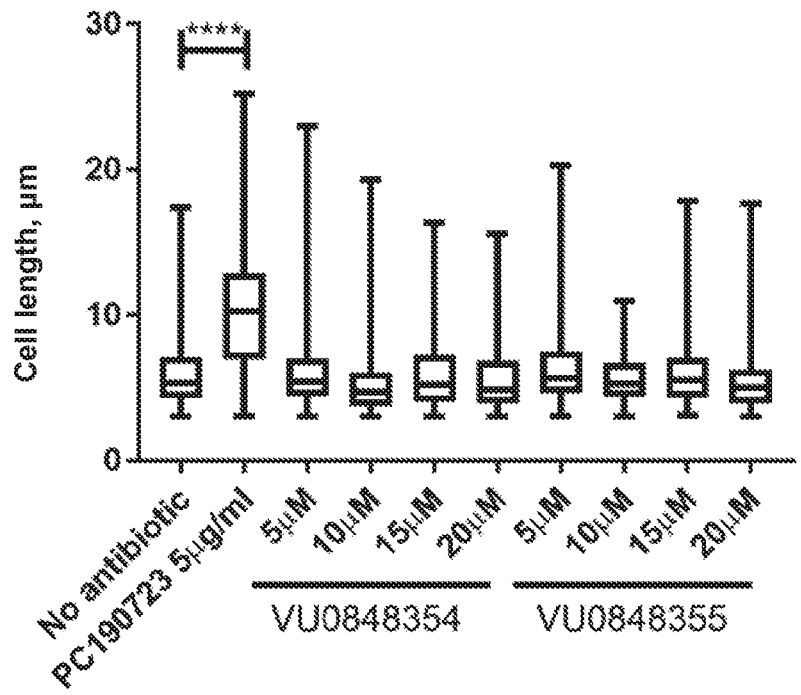
FIGS. 7A-7D show that chrysophaentins have a unique mode of inhibiting cell wall biosynthesis in *B. subtilis*. Fluorescently labeled proteins (FtsZ/A) and PBP2B allow visualization of peptidoglycan (PG) synthesis.
Figure 7B:
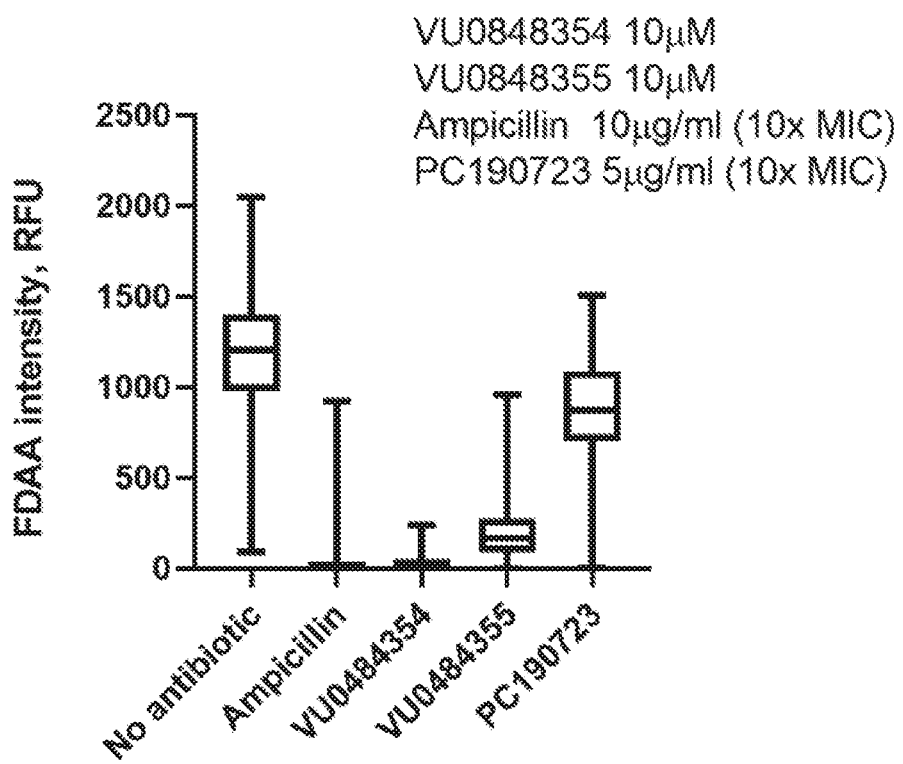
Figure 7C:
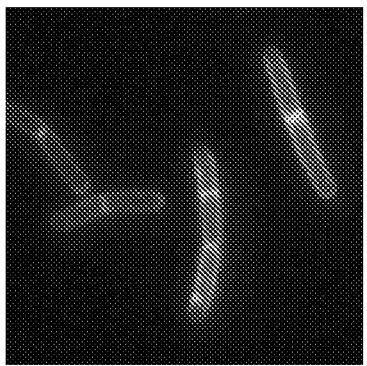
Figure 7C:
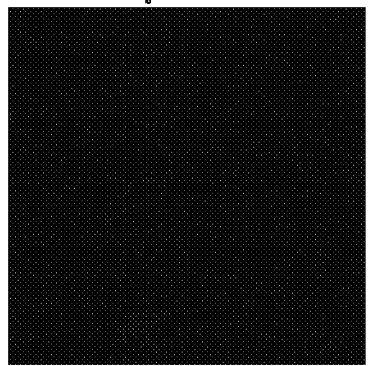
Figure 7C:
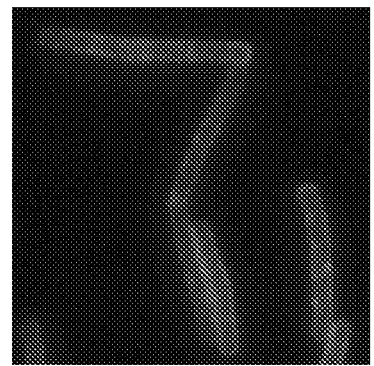
Figure 7C:
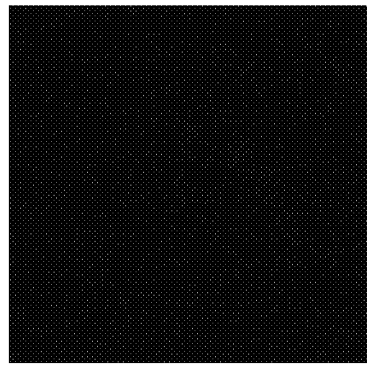
Figure 7C:
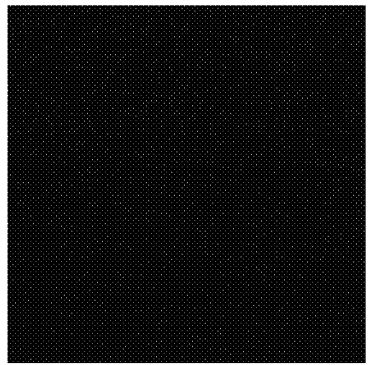
Figure 7D:
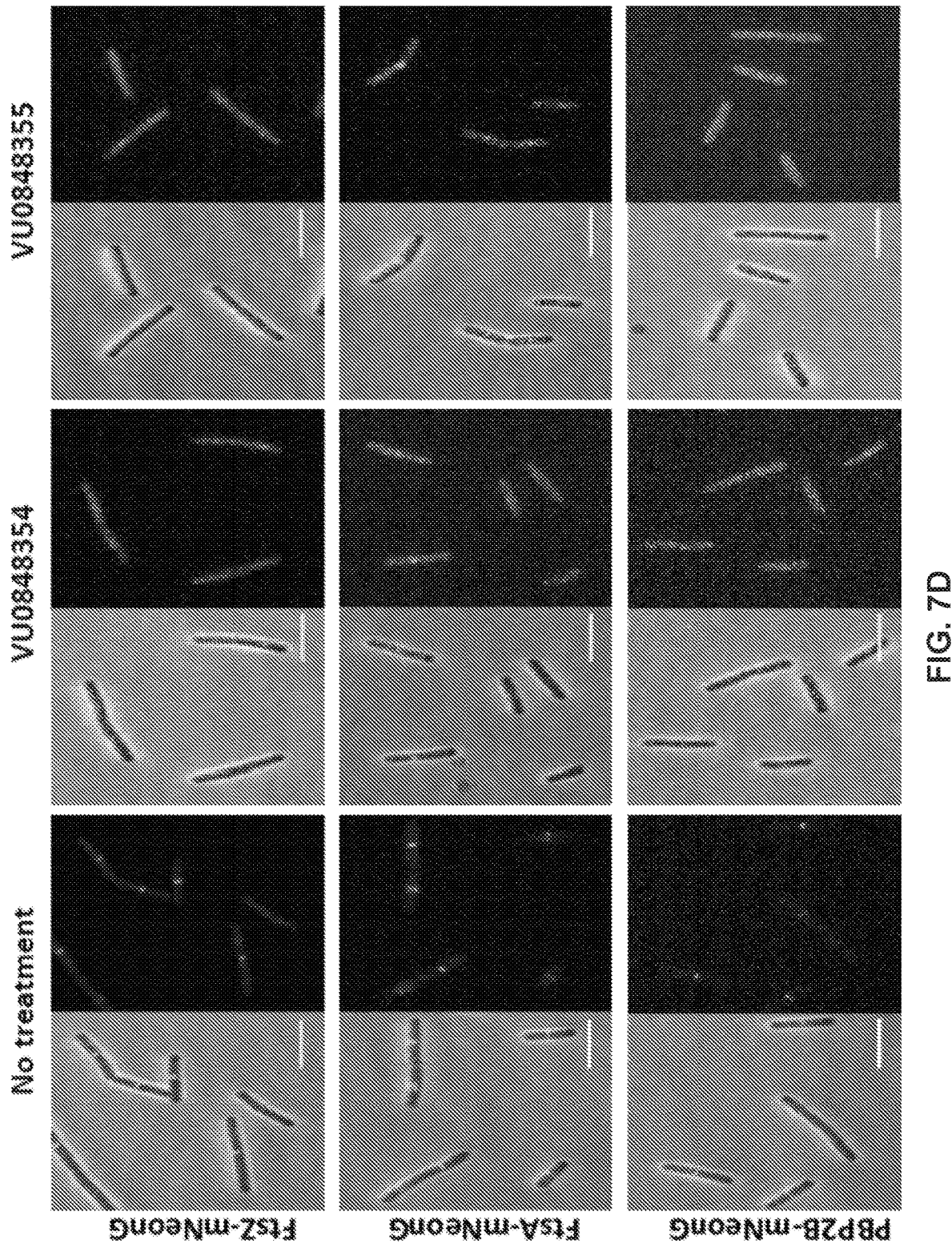

It was observed that VU0848355 and VU0848354 treatment in *B. subtilis* led to the unique dispersion of FtsZ, FtsA and PBP2B (FIG. 7D). It was also shown that the well-characterized FtsZ inhibitor PC1907723 (FIG. 3A) leads to expected cell lengthening, while, surprisingly, neither VU0848355 and VU0848354 replicates the cell lengthening phenotype (FIG. 7A). Instead, like the well-known peptidoglycan inhibitor ampicillin, VU0848355 and VU0848354 inhibited both lateral and septal peptidoglycan synthesis as demonstrated by inhibition of FDAA incorporation (FIGS. 7B and 7C). These results imply that an unprecedented mechanism is adopted by the chrysophaentins for inhibition of cell wall biosynthesis. Natural chrysophaentin A replicates this phenotype as it also led to dispersion of the septal peptidoglycan synthesis machinery.

Time-lapse microscopy was employed to monitor the dynamics of FtsZ motion before and after treatment by these compounds. FtsZ movement drives the septal peptidoglycan synthesis machinery in *B. subtilis*. The movement is carried out by a "treadmilling process" where FtsZ monomer polymerizes at one end and disassembles at the other. FtsZ polymerization is triggered by binding to GTP while its disassembly is catalyzed by GTP hydrolysis to GDP. It was observed that the cells treated with VU0848354 (5×MIC) did not elongate as observed with the well characterized FtsZ inhibitor PC1907723. These results demonstrates that the 9-dechlorochrysophaentins express their antimicrobial activity different from PC1907723 and inhibit peptidoglycan synthesis by a novel mechanism different from the beta lactam ampicillin.

Inspection of the $^1$H and $^{13}$C NMR's indicate that VU0845355, which possesses the natural C ring substitution pattern, shows signal broadening at room and higher temperatures suggestive of restricted bond rotation. In contrast, isomeric VU0848354 displays sharp 1H and $^{13}$C NMR signals indicative of rapid bond rotation. For example, the methyl ether signals ($^{13}$C NMR) for VU0848354 resonate as a sharp singlet at δ 55.5 while the corresponding signals in VU0845355 are broadened to the extent of not being observed. Likewise, in the proton NMR of VU0848354, $H_{14'}$ and $H_{16'}$ sharply resonate at δ 6.37, and in VU0845355 only seven of nine expected signals in the aromatic region are observed with $H_{14'}$ and $H_{16'}$ presumably broadened to the extent of not being observed. Variable temperature (high and low temperature) NMR did not lead to sharpening of NMR signals. This difference in rate of interconversion may be associated with the greater potency of the unnatural C ring isomers.

For reasons of completeness, various aspects of the invention are set out in the following numbered clauses:

Clause 1. A compound of formula (I), or a pharmaceutically acceptable salt thereof,

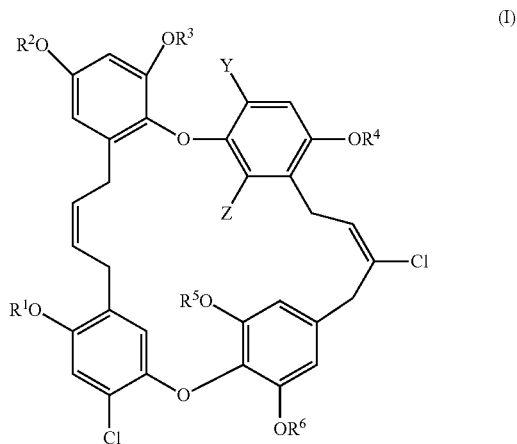

(I)

wherein
$R^1$, $R^2$, $R^3$, $R^4$, $R^5$, and $R^6$ are independently H, $C_{1-4}$alkyl, $C_{3-6}$cycloalkyl, —$CH_2C_{3-6}$cyclalkyl, —C(O) H, —C(O)$C_{1-4}$alkyl, —C(O)$C_{3-6}$cycloalkyl, or —C(O)$CH_2C_{3-6}$cyclalkyl; and
Y is halogen and Z is H; or Y is H and Z is halogen.

Clause 2. The compound of clause 1, or a pharmaceutically acceptable salt thereof, having a structure of formula (I-a).

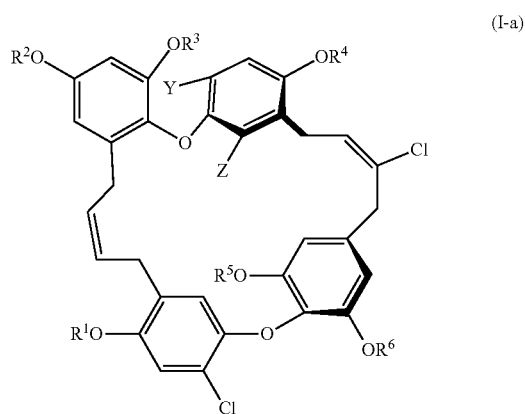

(I-a)

Clause 3. The compound of any one of clauses 1-2, or a pharmaceutically acceptable salt thereof, wherein Y is halogen and Z is H.

Clause 4. The compound of any one of clauses 1-2, or a pharmaceutically acceptable salt thereof, wherein Y is H and Z is halogen.

Clause 5. The compound of any one of clauses 1-4, or a pharmaceutically acceptable salt thereof, wherein $R^1$, $R^2$, $R^3$, $R^4$, $R^5$, and $R^6$ are independently H or $C_{1-4}$alkyl.

Clause 6. The compound of any one of clauses 1-5, or a pharmaceutically acceptable salt thereof, wherein $R^1$, $R^2$, $R^3$, $R^4$, $R^5$, and $R^6$ are independently H, methyl, or isopropyl.

Clause 7. The compound of any one of clauses 1-6, or a pharmaceutically acceptable salt thereof, wherein $R^1$, $R^2$, and $R^3$ are H; and $R^4$, $R^5$, and $R^6$ are independently H, methyl, or isopropyl.

Clause 8. The compound of any one of clauses 1-6, or a pharmaceutically acceptable salt thereof, wherein $R^1$, $R^2$, $R^3$ and $R^4$ are H; and $R^5$ and $R^6$ are independently H, methyl, or isopropyl.

Clause 9. The compound of any one of clauses 1-8, or a pharmaceutically acceptable salt thereof, wherein $R^1$, $R^2$, $R^3$ $R^4$, $R^5$, and $R^6$ are H, Y is halogen, Z is H;

$R^1$, $R^2$, $R^3$ $R^4$, $R^5$, and $R^6$ are H, Y is H, Z is halogen;

$R^1$, $R^2$, $R^3$ and $R^4$ are H; $R^5$ and $R^6$ are methyl, Y is halogen, Z is H; or $R^1$, $R^2$, $R^3$ and $R^4$ are H; $R^5$ and $R^6$ are methyl, Y is H, Z is halogen.

Clause 10. The compound of clause 9, or a pharmaceutically acceptable salt thereof, wherein $R^1$, $R^2$, $R^3$ $R^4$, $R^5$, and $R^6$ are H, Y is Cl, and Z is H.

Clause 11. The compound of clause 9, or a pharmaceutically acceptable salt thereof, wherein $R^1$, $R^2$, $R^3$ $R^4$, $R^5$, and $R^6$ are H, Y is H, and Z is Cl.

Clause 12. The compound of clause 9, or a pharmaceutically acceptable salt thereof, wherein $R^1$, $R^2$, $R^3$ and $R^4$ are H; $R^5$ and $R^6$ are methyl, Y is Cl, and Z is H.

Clause 13. The compound of clause 9, or a pharmaceutically acceptable salt thereof, wherein $R^1$, $R^2$, $R^3$ and $R^4$ are H; $R^5$ and $R^6$ are methyl, Y is H, and Z is Cl.

Clause 14. A pharmaceutical composition comprising a compound of any one of clauses 1-13, or a pharmaceutically acceptable salt thereof, and a pharmaceutically acceptable carrier.

Clause 15. A method of inhibiting the growth of a bacterium, comprising contacting the bacterium with an effective amount of a compound of any one of clauses 1-13, or a pharmaceutically acceptable salt thereof.

Clause 16. The method of clause 15, wherein the bacterium is a Gram-positive bacterium or a Gram-negative bacterium.

Clause 17. The method of any one of clauses 15-16, wherein the bacterium is a Gram-positive bacterium.

Clause 18. The method of any one of clauses 15-17, wherein the bacterium is *S. aureus* or *E. faecium*.

Clause 19. The method of any one of clauses 15-18, wherein the bacterium is an antibiotic-resistant bacterium.

Clause 20. The method of any one of clauses 15-19, wherein the bacterium is methicillin resistant *S. aureus* (MRSA) or vancomycin resistant *E. faecium* (VREF).

Clause 21. A method of treating a bacterial infection in a subject in need thereof, comprising administering to the subject an effective amount of a compound of any one of clauses 1-13, or a pharmaceutically acceptable salt thereof.

What is claimed is:

1. A compound of formula (I), or a pharmaceutically acceptable salt thereof,

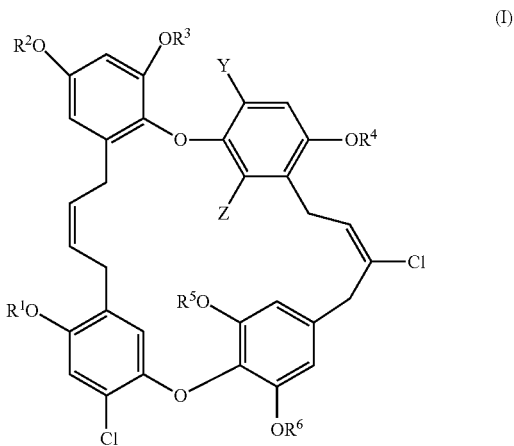

wherein $R^1$, $R^2$, $R^3$, $R^4$, $R^5$, and $R^6$ are independently H, $C_{1-4}$alkyl, $C_{3-6}$cycloalkyl, —$CH_2C_{3-6}$cyclalkyl, —C(O)H, —C(O)$C_{1-4}$alkyl, —C(O)$C_{3-6}$cycloalkyl, or —C(O)$CH_2C_{3-6}$cyclalkyl; and Y is halogen and Z is H; or Y is H and Z is halogen.

2. The compound of claim 1, or a pharmaceutically acceptable salt thereof, having a structure of formula (I-a).

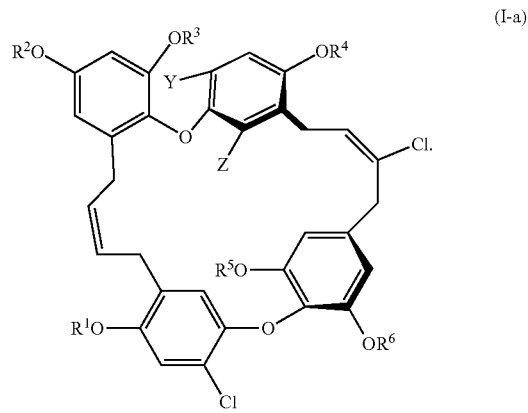

3. The compound of claim 1, or a pharmaceutically acceptable salt thereof, wherein Y is halogen and Z is H.

4. The compound of claim 1, or a pharmaceutically acceptable salt thereof, wherein Y is H and Z is halogen.

5. The compound of claim 1, or a pharmaceutically acceptable salt thereof, wherein $R^1$, $R^2$, $R^3$, $R^4$, $R^5$, and $R^6$ are independently H or $C_{1-4}$alkyl.

6. The compound of claim 1, or a pharmaceutically acceptable salt thereof, wherein $R^1$, $R^2$, $R^3$, $R^4$, $R^5$, and $R^6$ are independently H, methyl, or isopropyl.

7. The compound of claim 1, or a pharmaceutically acceptable salt thereof, wherein $R^1$, $R^2$, and $R^3$ are H; and $R^4$, $R^5$, and $R^6$ are independently H, methyl, or isopropyl.

8. The compound of claim 1, or a pharmaceutically acceptable salt thereof, wherein $R^1$, $R^2$, $R^3$ and $R^4$ are H; and $R^5$ and $R^6$ are independently H, methyl, or isopropyl.

9. The compound of claim 1, or a pharmaceutically acceptable salt thereof, wherein
$R^1$, $R^2$, $R^3$ $R^4$, $R^5$, and $R^6$ are H, Y is halogen, Z is H;
$R^1$, $R^2$, $R^3$ $R^4$, $R^5$, and $R^6$ are H, Y is H, Z is halogen;
$R^1$, $R^2$, $R^3$ and $R^4$ are H; $R^5$ and $R^6$ are methyl, Y is halogen, Z is H; or
$R^1$, $R^2$, $R^3$ and $R^4$ are H; $R^5$ and $R^6$ are methyl, Y is H, Z is halogen.

10. The compound of claim 9, or a pharmaceutically acceptable salt thereof, wherein $R^1$, $R^2$, $R^3$ $R^4$, $R^5$, and $R^6$ are H, Y is Cl, and Z is H.

11. The compound of claim 9, or a pharmaceutically acceptable salt thereof, wherein $R^1$, $R^2$, $R^3$ $R^4$, $R^5$, and $R^6$ are H, Y is H, and Z is Cl.

12. The compound of claim 9, or a pharmaceutically acceptable salt thereof, wherein $R^1$, $R^2$, $R^3$ and $R^4$ are H; $R^5$ and $R^6$ are methyl, Y is Cl, and Z is H.

13. The compound of claim 9, or a pharmaceutically acceptable salt thereof, wherein $R^1$, $R^2$, $R^3$ and $R^4$ are H; $R^5$ and $R^6$ are methyl, Y is H, and Z is Cl.

14. A pharmaceutical composition comprising a compound of claim 1, or a pharmaceutically acceptable salt thereof, and a pharmaceutically acceptable carrier.

15. A method of inhibiting the growth of a bacterium, comprising contacting the bacterium with an effective amount of a compound of claim 1, or a pharmaceutically acceptable salt thereof.

16. The method of claim 15, wherein the bacterium is a Gram-positive bacterium or a Gram-negative bacterium.

17. The method of claim 15, wherein the bacterium is *S. aureus* or *E. faecium*.

18. The method of claim 15, wherein the bacterium is an antibiotic-resistant bacterium.

19. The method of claim 15, wherein the bacterium is methicillin resistant *S. aureus* (MRSA) or vancomycin resistant *E. faecium* (VREF).

20. A method of treating a bacterial infection in a subject in need thereof, comprising administering to the subject an effective amount of a compound of claim 1, or a pharmaceutically acceptable salt thereof.

\* \* \* \* \*